(12) United States Patent
Lin et al.

(10) Patent No.: US 10,538,592 B2
(45) Date of Patent: Jan. 21, 2020

(54) ANTIBODIES, BINDING FRAGMENTS, AND METHODS OF USE

(71) Applicant: CHO PHARMA INC., Taipei (TW)

(72) Inventors: Nan-Horng Lin, Vernon Hills, IL (US); Chiu-Chen Huang, Taipei (TW); Chien-Yu Chen, Taipei (TW); Kuo-Ching Chu, Taipei (TW); Chi-Huey Wong, Rancho Santa Fe, CA (US); Han-Chung Wu, Taipei (TW)

(73) Assignee: CHO PHARMA, INC., Taipei (TW)

( * ) Notice: Subject to any disclaimer, the term of this patent is extended or adjusted under 35 U.S.C. 154(b) by 0 days.

(21) Appl. No.: 15/683,685

(22) Filed: Aug. 22, 2017

(65) Prior Publication Data

US 2018/0291109 A1    Oct. 11, 2018

Related U.S. Application Data

(60) Provisional application No. 62/378,102, filed on Aug. 22, 2016.

(51) Int. Cl.
| | | |
|---|---|---|
| *A61K 39/395* | (2006.01) | |
| *C07K 16/30* | (2006.01) | |
| *A61P 35/00* | (2006.01) | |
| *A61K 45/06* | (2006.01) | |
| *A61K 39/00* | (2006.01) | |

(52) U.S. Cl.
CPC .... *C07K 16/3076* (2013.01); *A61K 39/39558* (2013.01); *A61K 45/06* (2013.01); *A61P 35/00* (2018.01); *A61K 2039/505* (2013.01); *C07K 2317/24* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |

(Continued)

FOREIGN PATENT DOCUMENTS

| | | |
|---|---|---|
| CN | 101855339 A | 10/2010 |
| CN | 101868534 A | 10/2010 |

(Continued)

OTHER PUBLICATIONS

Rudikoff et al. (Proc Natl Acad Sci USA 1982 vol. 79 p. 1979) (Year: 1979).*
MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
Greene, Theodora et al., Protective Groups in Organic Synthesis, pp. 42-51 and 96-103, 1991.

(Continued)

*Primary Examiner* — Meera Natarajan
(74) *Attorney, Agent, or Firm* — Duane Morris LLP

(57) ABSTRACT

The present disclosure relates to anti-SSEA4 antibodies and bindings fragments thereof comprising specific complementarity determining regions capable of high affinity binding to SSEA4 molecules and SSEA4-associated expressing tumor cells, such as breast cancer, pancreatic cancer, and renal cancer cells. The anti-SSEA4 antibodies and binding fragments induce ADCC or CDC effects in the targeted tumor cells and inhibit and/or reduce the cancer/tumor proliferation. The present disclosure also provides anti-SSEA4 antibodies and binding fragments thereof as a pharmaceutical composition for treating cancer. In addition, the anti-SSEA4 antibodies and binding fragments are useful in the diagnosis of cancers.

**26 Claims, 37 Drawing Sheets
(10 of 37 Drawing Sheet(s) Filed in Color)
Specification includes a Sequence Listing.**

(56) References Cited

U.S. PATENT DOCUMENTS

| | | |
|---|---|---|
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,592,004 B2 | 9/2009 | Kaisheva et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,163,290 B2 | 4/2012 | Tsuji et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,715,963 B2 | 5/2014 | Sethuraman |
| 8,716,465 B2 | 5/2014 | Rossi et al. |
| 8,765,390 B2 | 7/2014 | Ailles et al. |
| 8,802,438 B2 | 8/2014 | Rossi et al. |
| 8,815,941 B2 | 8/2014 | Withers |
| 8,883,506 B2 | 11/2014 | Rossi et al. |

(56) References Cited

U.S. PATENT DOCUMENTS

| | | |
|---|---|---|
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,547,009 B2 | 1/2017 | Wong et al. |
| 9,759,726 B2 | 9/2017 | Wong et al. |
| 9,782,476 B2 | 10/2017 | Wong et al. |
| 9,803,177 B2 | 10/2017 | Rossi et al. |
| 9,874,562 B2 | 1/2018 | Wong et al. |
| 9,879,042 B2 | 1/2018 | Wong et al. |
| 9,914,956 B2 | 3/2018 | Wong et al. |
| 9,975,965 B2 | 5/2018 | Wong et al. |
| 9,981,030 B2 | 5/2018 | Wong et al. |
| 9,982,041 B2 | 5/2018 | Wong et al. |
| 10,005,847 B2 | 6/2018 | Wong |
| 10,023,892 B2 | 7/2018 | Wong |
| 10,086,054 B2 | 10/2018 | Wong et al. |
| 10,087,236 B2 | 10/2018 | Wong et al. |
| 10,111,951 B2 | 10/2018 | Wong et al. |
| 10,118,969 B2 | 11/2018 | Wong |
| 10,119,972 B2 | 11/2018 | Wong et al. |
| 10,130,714 B2 | 11/2018 | Wong et al. |
| 10,150,818 B2 | 12/2018 | Wong et al. |
| 10,214,765 B2 | 2/2019 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0213297 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0145838 A1 | 6/2008 | Suda et al. |
| 2008/0175870 A1 | 7/2008 | Mather et al. |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0060921 A1 | 3/2009 | Dickey et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0081150 A1 | 4/2010 | Liu et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2010/0275280 A1 | 10/2010 | Clevers et al. |
| 2011/0086408 A1 | 4/2011 | Powers |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0262358 A1 | 10/2011 | Torigoe et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0071390 A1 | 3/2013 | Stadheim et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0227290 A1 | 8/2014 | Sethuraman |
| 2014/0302028 A1 | 10/2014 | Zha |
| 2014/0308746 A1 | 10/2014 | Rossi et al. |
| 2015/0087814 A1 | 3/2015 | Wang |
| 2015/0094237 A1 | 4/2015 | Liang et al. |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0017390 A1 | 1/2016 | Wong et al. |
| 2016/0102151 A1 | 4/2016 | Wong et al. |
| 2016/0213763 A1 | 7/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0038378 A1 | 2/2017 | Wong et al. |
| 2017/0275389 A1 | 9/2017 | Wong et al. |
| 2017/0283488 A1 | 10/2017 | Yu et al. |
| 2017/0283878 A1 | 10/2017 | Wong et al. |
| 2017/0362265 A1 | 12/2017 | Wong et al. |
| 2017/0362330 A1 | 12/2017 | Liu |
| 2018/0106780 A1 | 4/2018 | Wong et al. |
| 2018/0155761 A1 | 6/2018 | Wong et al. |
| 2018/0193481 A1 | 7/2018 | Chang et al. |
| 2018/0265590 A1 | 9/2018 | Wong et al. |
| 2018/0291109 A1 | 10/2018 | Lin et al. |
| 2018/0362662 A1 | 12/2018 | Wong et al. |

FOREIGN PATENT DOCUMENTS

| | | |
|---|---|---|
| CN | 102203290 A | 9/2011 |
| CN | 103436627 A | 12/2013 |
| CN | 104225616 A | 12/2014 |
| EP | 0404097 A2 | 12/1990 |

(56) References Cited

FOREIGN PATENT DOCUMENTS

| | | |
|---|---|---|
| EP | 0341735 B1 | 9/1992 |
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | H06-217769 A | 8/1994 |
| JP | 11-343295 A | 12/1999 |
| JP | 2005-06008 | 5/2000 |
| JP | 2002-371087 A | 12/2002 |
| JP | 2008-025989 A | 2/2008 |
| JP | 2008-526812 A | 7/2008 |
| JP | 2009-515979 A | 4/2009 |
| JP | 2012-503656 A | 2/2012 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/072624 A2 | 7/2006 |
| WO | WO 2006/106959 | 10/2006 |
| WO | WO 2006/126069 A2 | 11/2006 |
| WO | WO 2006/130458 A2 | 12/2006 |
| WO | WO 2007/053648 A2 | 5/2007 |
| WO | WO 2007/059188 A1 | 5/2007 |
| WO | WO 2007/078873 A1 | 7/2007 |
| WO | WO 2007/0133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2009/126735 A1 | 10/2009 |
| WO | WO 2010/006315 A2 | 1/2010 |
| WO | WO 2010/009271 A1 | 1/2010 |
| WO | WO 2010/011703 | 1/2010 |
| WO | WO2010/029302 A2 | 3/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2012/162277 A1 | 11/2012 |
| WO | WO 2013/011347 A1 | 1/2013 |
| WO | WO 2013/024895 A1 | 2/2013 |
| WO | WO 2013/066761 A1 | 5/2013 |
| WO | WO 2013/088395 A1 | 6/2013 |
| WO | WO 2013/106937 A1 | 7/2013 |
| WO | WO 2013/120066 A1 | 8/2013 |
| WO | WO2013/126993 A1 | 9/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |
| WO | WO 2014/031762 A1 | 2/2017 |

OTHER PUBLICATIONS

Herter et al "Glycoengineering of therapeutic antibodies enhances monocyte/macrophage-mediated phagocytosis and cytotoxicity" J Immunol. Mar. 1, 2014, vol. 192 No. 5, pp. 2252-2260.

Jez et al "Significant Impact of Single N-Glycan Residues on the Biological Activity of Fc-based Antibody-like Fragments" Journal of Biological Chemistry Jul. 13, 2012, vol. 287 No. 29, pp. 24313-24319.

Junttila et al "Superior in vivo efficacy of afucosylated trastuzumab in the treatment of HER2-amplified breast cancer" Cancer Res. 2010, vol. 70 No. 11, pp. 4481-4489.

Komarova et al "Plant-Made Trastuzumab (Herceptin) Inhibits HER2/Neu+ Cell Proliferation and Retards Tumor Growth" PLOS One 2011,vol. 6 No. 3, p. e17541.

McConville, Malcolm J., and M. A. Ferguson. "The structure, biosynthesis and function of glycosylated phosphatidylinositols in the parasitic protozoa and higher eukaryotes." Biochemical Journal 294.Pt 2 (1993): 305.

Ochiai et al "Expeditious Chemoenzymatic Synthesis of Homogeneous N-Glycoproteins Carrying Defined Oligosaccharide Ligands" J. Am. Chem. Soc. 2008, vol. 130 No. 41, pp. 13790-13803.

Office Action dated Aug. 29, 2017, from corresponding Japanese Patent Application No. 2016-169045, 5 total pages.

Schelhaas, Michael et al., Protecting Group Strategies in Organic Synthesis, Angew. Chem. Int. Ed. Engl. 1996, 35, 2056-2083.

Tebbey et al "Importance of manufacturing consistency of the glycosylated monoclonal antibody adalimumab (Humira®) and potential impact on the clinical use of biosimilars" Gabi Journal 2016, vol. 5 Issue 2, pp. 70-73.

(56) References Cited

OTHER PUBLICATIONS

Unverzagt, Carlo et al., A Double Regio- and Stereoselective Glycosylation Strategy for the Synthesis of N-Glycans, Chem. Eur. J., 2008, 14, 1304-1311.
Wiseman, Gregory A., et al. "Radiation dosimetry results and safety correlations from (90) Y-ibritumomab tiuxetan radioimmunotherapy for relapsed or refractory non-Hodgkin's lymphoma: Combined data from 4 clinical trials" The Journal of Nuclear Medicine 44.3 (2003): 465-474.
Zhang et al "Glycoengineered Pichia produced anti-HER2 is comparable to trastuzumab in preclinical study" mAbs May-Jun. 2011, vol. 3 No. 3, pp. 289-298.
Hodoniczky J, Zheng YZ, James DC. "Control of recombinant monoclonal antibody effector functions by Fc N-glycan remodeling in vitro" Biotechnology Progress. 2005;21(6):1644-1652.
Komarova TV, et al. "Trastuzumab and pertuzumab plant biosimilars: Modification of Asn297-linked glycan of the mAbs produced in a plant with fucosyltransferase and xylosyltransferase gene knockouts" Biochemistry (Moscow). Apr. 1, 2017;82(4):510-520.
Liu L. "Antibody glycosylation and its impact on the pharmacokinetics and pharmacodynamics of monoclonal antibodies and Fc-fusion proteins" Journal of Pharmaceutical Sciences. Jun. 2015;104(6):1866-1884.
Raju TS. "Terminal sugars of Fc glycans influence antibody effector functions of IgGs" Current Opinion in Immunology. Aug. 1, 2008;20(4):471-478.
Zhou Q, et al. "Site-specific antibody-drug conjugation through glycoengineering" Bioconjugate Chemistry. Feb. 28, 2014;25(3):510-520.
U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Abrahmsén et al, "Analysis of signals for secretion in the staphylococcal protein A gene," EMBO J., Dec. 30, 1985, 4(13B):3901-3906.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Altschul SF et al., "Basic local alignment search tool", J Mol Biol. Oct. 5, 1990;215(3):403-10.
Altschul SF, et al., "Gapped BLAST and PSI-BLAST: a new generation of protein database search programs", Nucleic Acids Res. Sep. 1, 1997;25(17):3389-402.
Amin, M. N. et al. Synthetic glycopeptides reveal the glycan specificity of HIV-neutralizing antibodies. Nat. Chem. Biol. 9, 521-526, (2013).
Anderson et al., "Stimulation of Natural Killer T Cells by Glycolipids", Molecules, May 2013, 18(12), 15662-15688.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.

Anthony, Robert et al., Recapitulation of IVIG Anti-Inflammatory Activity with a Recombinant lgG Fc, Science Apr. 18, 2008. 320:373-376.
Arase et al., "NK1.1$^+$ CD4$^+$ CD8$^-$ thymocytes with specific lymphokine secretion," Eur. J. Immunol., Jan. 1993, 23(1):307-310.
Arié et al., "Chaperone function of FkpA, a heat shock prolyl isomerase, in the periplasm of Escherichia coli," Mol. Microbiol., Jan. 2001, 39(1):199-210.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bachmann, Cellular and Molecular Biology, vol. 2, Chapter 72: Derivations and Genotypes of Some Mutant Derivatives of Escherichia coli K-12, Neidhardt et al., eds., 1987, pp. 1190-1219, American Society for Microbiology, Washington, D.C.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," Lancet, Mar. 15, 1986, 327(8481):603-605.
Banchereau et al., "Dendritic cells and the control of immunity," Nature, Mar. 19, 1998, 392(6673):245-252.
Barbas et al., "Assembly of combinatorial antibody libraries on phage surfaces: the gene III site," Proc. Natl. Acad. Sci. U.S.A., Sep. 15, 1991, 88(18):7978-7982.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barbas et al., "Semisynthetic combinatorial antibody libraries: a chemical solution to the diversity problem," Proc. Natl. Acad. Sci. U.S.A., May 15, 1992, 89(10):4457-4461.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barnes et al., "Methods for growth of cultured cells in serum-free medium," Anal. Biochem., Mar. 1, 1980, 102(2):255-270.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", J Clin Oncol. Mar. 1996;14(3):737-44.
Baskin, J.M.; Amacher, S. L.; Bertozzi, C.R."In vivo imaging of membraneassociated glycans in developing zebrafish." Science 2008, 320, 664-667.
Bass et al., "Hormone phage: an enrichment method for variant proteins with altered binding properties," Proteins, 1990, 8(4):309-314.

(56) References Cited

OTHER PUBLICATIONS

Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" *MAbs*. Mar.-Apr. 2011;3(2):107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by The Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berg, Jan-Olof et al., Purification of Glycoside Hydrolases From Bacteroides Fragilis, Applied and Environmental Microbiology, vol. 40, No. 1, Jul. 1980, p. 40-47.
Berge, Steven et al. J. Pharmaceutical Sciences (1977) 66: 1-19.
Berra et al., "Correlation between ganglioside distribution and histological grading of human astrocytomas," *Int. J. Cancer*, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Birklé et al., "Role of tumor-associated gangliosides in cancer progression," *Biochimie*, Mar.-Apr. 2003, 85(3-4):455-463.
Blixt, O. et al. Printed covalent glycan array for ligand profiling of diverse glycan binding proteins. Proc. Natl. Acad. Sci. U.S. A. 101, 17033-17038, (2004.
Bobo et al., "Convection-enhanced delivery of macromolecules in the brain," *Proc. Natl. Acad. Sci. U.S.A.*, Mar. 15, 1994, 91(6) 2076-2080.
Boens, N. et al. "Fluorescent indicators based on BODIPY." Chem. Soc. Rev. 2012, 41, 1130-1172.
Boerner et al., "Production of antigen-specific human monoclonal antibodies from in vitro-primed human splenocytes," *J. Immunol.*, Jul. 1, 1991, 147(1):86-95.
Borg et al., "CD1d-lipid-antigen recognition by the semi-invariant NKT T-cell receptor," *Nature*, Jul. 5, 2007, 448(7149):44-49.
Bosmann et al., "Enzyme activity in invasive tumors of human breast and colon," *Proc. Natl. Acad. Sci. USA*, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Brennan et al., "Preparation of bispecific antibodies by chemical recombination of monoclonal immunoglobulin G$_1$ fragments," *Science*, Jul. 5, 1985, 229(4708):81-83.

Bricard et al., "Enrichment of human CD4$^+$ Vα24/Vβ11 invariant NKT cells in intrahepatic malignant tumors," *J. Immunol.*, Apr. 15, 2009, 182(8):5140-5151.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüggemann et al., "Designer mice: the production of human antibody repertoires in transgenic animals," *Year in Immunol.*, 1993, 7:33-40.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Capel PJ et al., "Heterogeneity of human IgG Fc receptors" *Immunomethods*. Feb. 1994;4(1):25-34.
Carlsson, Jan et al., Protein Thiolation and Reversible Protein-Protein Conjugation, Biochem J 173: 723-737 (1978).
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol*. May 2006;6(5):343-357.
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, Aug. 2007 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Natl. Acad. Sci. USA*, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjugates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Chen et al., "Chaperone activity of DsbC," *J. Bio. Chem.*, Jul. 9, 1999, 274(28):19601-19605.

(56) References Cited

OTHER PUBLICATIONS

Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Cheng, Peter et al., Oseltamivir-and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat. Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Canonical structures for the hypervariable regions of immunoglobulins," *J. Mol. Biol.*, Aug. 20, 1987, 196(4):901-917.
Chothia et al., "Domain association in immunoglobulin molecules. The packing of variable domains," *J. Mol. Biol.*, Dec. 5, 1985, 186(3):651-663.
Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res.* 1989;52:81-149.
Clynes R, et al., "Fc receptors are required in passive and active immunity to melanoma" *Proc Natl Acad Sci U S A.* Jan. 20, 1998;95(2):652-6.
Codelli, J. A. et al., Second-Generation Difluorinated Cycloctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2.6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013.
Crispin et al., "Carbohydrate and domain architecture of an immature antibody glycoform exhibiting enhanced effector functions," J. Mol. Biol., Apr. 17, 2009, 387(5):1061-1066.
Cunningham et al., "High-resolution epitope mapping of hGH-receptor interactions by alanine-scanning mutagenesis," *Science*, Jun. 2, 1989, 244(4908):1081-1085.
Cyranoski, Threat of Pandemic Brings Flu Drug Back to Life, Nat. Med. Sep. 2005, 11(9): 909.
Daëron, "Fc receptor biology," *Annu. Rev. Immunol.*, 1997, 15:203-234.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine $\alpha\beta$ T cells expressing invariant TCR alpha-chains," *J. Immunol.*, Jun. 15, 1997, 158(12):5603-5611.
De Almeida et al., "Thiacycloalkynes for copper-free click chemistry," *Angew. Chem. Int. Ed. Engl.*, Mar. 5, 2012, 51(10):2443-2447.
Debets, M. F. et al., Bioconjugation with Strained Alkenes and Alkynes, Acc. Chem. Res. 2011, 44, 805-815.
De Haas et al., "Fc$\gamma$ receptors of phagocytes," *J. Lab. Clin. Med.*, Oct. 1995, 126(4):330-341.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant V$\alpha$24-J$\alpha$Q/V$\beta$11 T cell receptor is expressed in all individuals by clonally expanded CD4$^-$8$^-$ T cells," *J. Exp. Med.*, Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "$\alpha$-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," *J. Exp. Med.*, Jun. 16, 2003, 197(12):1667-1676.
Dicker, Martina et al., Using Glyco-Engineering to Produce Therapeutic Proteins, Expert Opinion on Biological Therapy, vol. 15, Jan. 1, 2015, pp. 1501-1516.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).

(56) References Cited

OTHER PUBLICATIONS

Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Durrant et al., "Immunology in the clinic review series; focus on cancer: glycolipids as targets for tumour immunotherapy," *Clin. Exp. Immunol.*, Feb. 2012, 167(2):206-215.
Eberl et al., "Selective bystander proliferation of memory CD4+ and CD8+ T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
European Search Report issued in connection with corresponding European Patent Application No. 15181446.4, dated Dec. 7, 2015, 10 pages.
Evans, Michael et al., "Mechanism-based profiling of enzyme families," *Chem. Rev.*, Aug. 2006, 106(8):3279-3301.
Evans, "The rise of azide-alkyne 1,3-dipolar 'click' cycloaddition and its application to polymer science and surface modification," *Australian J. Chem.*, Jun. 2007, 60(6):384-395.
Extended European Search Report dated Jan. 5, 2016 in European Patent Application No. 13830785.5, in 10 pages.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from *Streptococcus Pneumoniae*, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.

Fellouse et al., "Synthetic antibodies from a four-amino-acid code: a dominant role for tyrosine in antigen recognition," *Proc. Natl. Acad. Sci. U.S.A.* Aug. 24, 2004, 101(34):12467-12472.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fishwild et al., "High-avidity human IgGκ monoclonal antibodies from a novel strain of minilocus transgenic mice," *Nature Biotechnol.*, Jul. 1996, 14(7):845-851.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Galfrè et al., "Preparation of monoclonal antibodies: strategies and procedures," *Methods Enzymol.*, 1981, 73(Pt B):3-46.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.

(56) References Cited

OTHER PUBLICATIONS

GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Gill et al., "Direct brain infusion of glial cell line-derived neurotrophic factor in Parkinson disease," *Nature Med.*, May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goding, *Monoclonal Antibodies: Principles and Practice 2nd ed., Chapter 3: Production of Monoclonal Antibodies*, 1986, pp. 59-103, Academic Press, London.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.
Govorkova et al, Combination chemotherapy for influenza. Viruses. Aug. 2010;2(8):1510-29.
Graham et al., "Characteristics of a human cell line transformed by DNA from human adenovirus type 5," *J. Gen. Virol.*, Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," *N. Engl. J. Med.*, May 20, 2004, 350(21):2191-2193.
Greenbaum et al., "Chemical approaches for functionally probing the proteome," *Mol. Cell. Proteomics*, 2002, 1:60-68.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Ha, YA et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, YA et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toin A2/B subunits," *J. Immunol.*, May 1, 1995, 154(9):4322-4332.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity. Mimicking affinity maturation," *J. Mol. Biol.*, 1992, 226(3):889-896.
Healthy Living, "10 Simple and Natural Ways to Boost Your Immune System," Published Jan. 31, 2014, downloaded from

(56) References Cited

OTHER PUBLICATIONS online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," Immunol. Lett., Dec. 1996, 54(2-3):195-199.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," Gene, Jun. 15, 1993, 128(1):119-126.
Holliger et al., "'Diabodies': small bivalent and bispecific antibody fragments," Proc. Nati. Acad. Sci. U.S.A., Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Honegger et al., "Yet another numbering scheme for immunoglobulin variable domains: an automatic modeling and analysis tool," J. Mol. Biol., Jun. 8, 2001, 309:657-670.
Hoogenboom et al., "By-passing immunisation: Human antibodies from synthetic repertoires of germline $V_H$ gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," Immunol. Today, Jun. 1992, 13(6):198-200.
Hsu et al., "Alkynyl sugar analogs for the labeling and visualization of glycoconjugates in cells," Proc. Natl. Acad. Sci. USA, Feb. 20, 2007, 104(8), 2614-2619.
Hsu, Nien-Yeen et al., Desorption Ionization of Biomolecules on Metals, Anal. Chem., 80, 5203-5210, 2008.
Huang et al., "Carbohydrate-based vaccines with a glycolipid adjuvant for breast cancer," Proc. Nati. Acad. Sci. U.S.A., Feb. 12, 2013, 110(7):2517-2522.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," J. Am. Chem. Soc., Apr. 24, 2013, 135(16):5934-5937.
Hurle et al., "Protein engineering techniques for antibody humanization," Curr. Opin. Biotechnol., Aug. 1994, 5(4):428-433.
Immunogenicity, Wikipedia p. 1-3. Downloaded on Aug. 16, 2016 from https://en.wikipedia.org/wiki/Immunogenicity. (2016).
Inouye et al., "Single-step purification of F(ab')$_{2\mu}$ , fragments of mouse monoclonal antibodies (immunoglobulins M) by hydrophobic interaction high-performance liquid chromatography using TSKgel Ether-5PW," J. Biochem. Biophys. Methods, Feb. 1993, 26(1):27-39.
International Search Report and Written Opinion issued for International application No. PCT/US2015/011748, dated Aug. 21, 2015, 17 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
International Search Report and Written Opinion in International Application No. PCT/US2017/048074, dated Dec. 26, 2017, 17 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," J. Immunol., Apr. 1, 1995, 154(7):3310-3319.
Jacobs et al., "Metabolic labeling of glycoproteins with chemical tags through unnatural sialic acid biosynthesis," Methods Enzymol., 2000, 327:260-275.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Japanese Office Action dated Apr. 21, 2015, from Related Japanese Patent Application No. 2013-510261, 6 Pages.

(56) References Cited

OTHER PUBLICATIONS

Jayasena, Sumedha, Aptamers: An Emerging Class of Molecules That Rival Antibodies in Diagnostics, Clin. Chem. (1999), 45, 1628-1650.

Jenkins N, Curling EM., "Glycosylation of recombinant proteins: problems and prospects", *Enzyme Microb Technol.* May 1994;16(5):354-64.

Jewett, J.C.; Bertozzi, C.R., Cu-Free Click Cycloaddition Reactions in Chemical Biology, Chem. Soc. Rev. 2010, 39, 1272-1279.

Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.

Jewett et al., "Synthesis of a fluorogenic cyclooctyne activate by Cu-free click chemistry," *Org. Lett.*, Nov. 18, 2011, 13(22):5937-5939.

Jin, R. C. et al., Photoinduced Conversion of Silver Nanospheres to Nanoprisms, Science (2001), 294, 1901-1903.

Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.

John, F. & Hendrickson, T. L. Synthesis of Truncated Analogues for Studying the Process of Glycosyl Phosphatidylinositol Modification. Org. Lett. 12, 2080-2083, (2010).

Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those fro ma mouse," *Nature*, May 29-Jun. 4, 1986, 321(6069):522-525.

Jones, "Analysis of polypeptides and proteins," *Adv. Drug Delivery Rev.*, Jan.-Apr. 1993, 10(1):29-90.

Jonges, M. et al., Dynamics of Antiviral-Resistant Influenza Viruses in the Netherlands, 2005-2008, Antiviral Res., Sep. 2009, 83(3): 290-297.

Jorgensen, Trond et al., Up-Regulation of the Oligosaccharide Sialyl Lewisx: A New Prognostic Parameter in Metastatic Prostate Cancer, Cancer Res. 55, 1817-1819, 1995.

Jose, Jiney et al., Energy transfer dyads based on Nile Red, Tetrahedron Letters (2009), 50(47), 6442-6445.

Joshi, Shantaran et al., Cell Surface Properties Associated with Malignancy of Metastatic Large Cell Lymphoma Cells, (1987) Cancer Res. 47, 3551-3557.

Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.

Kale et al., Detection of intact influenza viruses using biotinylated biantennary S-sialosides. J Am Chem Soc. Jul. 2, 2008;130(26):8169-71.

Kalesh et al., "Peptide-based activity-based probes (ABPs) for target-specific profiling of protein tyrosine phosphatases (PTPs)," *Chem. Commun.*, Jan. 28, 2010, 46(4):589-591.

Kamkaew, A. et al., "BODIPY dyes in photodynamic therapy." Chem. Soc. Rev. 2013, 42, 77-88.

Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.

Kaneko et al., "Anti-inflammatory activity of immunoglobulin G resulting from Fc sialylation," *Science*, Aug. 4, 2006, 313(5787):670-673.

Kawakami et al., "Critical role of Va14+ natural killer T cells in the innate phase of host protection against *Streptococcus pneumoniae* infection," *Eur. J. Immunol.*, Dec. 2003, 33(12):3322-3330.

Kawano et al., "CD1d-restricted and TCR-mediated activation of $v_\alpha 14$ NKT cells by glycosylceramides," *Science*, Nov. 28, 1997, 278(5343):1626-1629.

Kanie, Osmau et al., Orthogonal glycosylation strategy in synthesis of extended blood group B determinant. Tetrahedron Lett. 37, 4551-4554 (1996).

Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.

Kannagi et al., "Stage-specific embryonic antigens (SSEA-3 and -4) are epitopes of a unique globo-series ganglioside isolated from human teratocarcinoma cells, "*EMBO J.*, 1983, 2(12):2355-2361.

Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.

Karlin, Samuel et al., Applications and Statistics for Multiple High-Scoring Segments in Molecular Sequences, Proc. Natl. Acad Sci. USA 90:5873-77, 1993.

Karlin S. et al., "Methods for assessing the statistical significance of molecular sequence features by using general scoring schemes", *Proc Natl Acad Sci USA*. Mar. 1990;87(6):2264-8.

Karmakar, M. et al., Current Trends in Research and Application of Microbial Cellulases, Research Journal of Microbiology, (2001) 6(1): 41-53.

Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communications, 332, 1004-1011, 2005.

Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.

Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).

Kidd et al., "Profiling serine hydrolase activities in complex proteomes," *Biochemistry*, Apr. 3, 2001, 40(13):4005-4015.

Kiick, K.L. et al., Identification of an Expanded Set of Translationally Active Methionine Analogues in *Escherichia coli*, tetrahedron 56:9487, 2001.

Kim et al., "Localization of the site of the murine IgG1 molecule that is involved in binding to the murine intestinal Fc receptor," *Eur. J. Immunol.*, 1994, 24:2429-2434.

Kim et al., High-Throughput Screening of Glycan-Binding Proteins Using Miniature Pig Kidney N-Glycan-Immobilized Beads, Chemistry & biology 15.3, p. 215-223 (2008).

Kim, Gap-Sue et al., AB Initio Study of Excited Electronic States and Vibronic Spectra of Phenyl Radical, Chem Phys. Lett., 2002, 3 5 2, 421.

Kimura et al., Design and Synthesis of Immobilized Tamiflu Analog on Resin for Affinity Chromatography, Tetrahedron Lett., Jul. 1, 2009, 50(26):3205-3208.

King, M. et al., New Tetramethlthiepinium (TMTI) for Copper-Free Click Chemistry, Chem. Commun. 2012, 48, 9308-9309.

Kitamura et al., "α-galactosylceramide induces early B-cell activation through IL-4 production by NKT cells," *Cell. Immunol.*, Jan. 10, 2000, 199(1):37-42.

Klein, J. et al., "Isomaltines and their N-acyl derivatives, their preparation, and use of some acyl derivatives as surfactants or for preparation of hydrophilic polymers," CAPLUS 110:95711 (1989).

Köhler et al., "Continuous cultures of fused cells secreting antibody of predefined specificity," *Nature*, Aug. 7, 1975, 256(5517):495-497.

Kolb et al., "Click chemistry: diverse chemical function from a few good reactions,"*Angew. Chem. Int. Ed. Engl.*, Jun. 1, 2001, 40(11):2004-2021.

Kolb et al., "The growing impact of click chemistry on drug discovery," *Drug Discov. Today*, Dec. 15, 2003, 8(24):1128-1137.

(56) References Cited

OTHER PUBLICATIONS

Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.

Komori, Tatsuya et al., Study on Systematizing the Synthesis of the A-Series Ganglioside Glycans GT1a, GD1a, and GM1 Using the Newly Developed N-Troc-Protected GM3 and GalN Intermediates, Carbohydr. Res. 2009, 344, 1453.

Kong, L. et al. Expression-system-dependent modulation of HIV-I envelope glycoprotein antigenicity and immunogenicity. J. Mol. Biol. 403, 131-147, (2010).

Kontermann, "Intrabodies as therapeutic agents," *Methods*, Oct. 2004, 34(2):163-170.

Kos, "Regulation of adaptive immunity by natural killer cells," *Immunol. Res.*, 1998, 17(3):303-312.

Koshihara et al., 1984, Biochmica et biophysica acta, 792(1), pp. 92-97.

Kostelny et al., "Formation of a bispecific antibody by the use of leucine zippers," *J. Immunol.*, Mar. 1, 1992, 148(5):1547-1553.

Kotteas et al., Immunotherapy for pancreatic cancer, J cancer Res Clin Oncol, 142(8): 1795-1805, 2016.

Kozbor, "A human hybrid myeloma for production of human monoclonal antibodies," *J. Immunol.*, Dec. 1984, 133(6):3001-3005.

Kriegler M et al., "A novel form of NF/cachectin is a cell surface cytotoxic transmembrane protein: ramifications for the complex physiology of TNF" *Cell*. Apr. 8, 1988;53(1):45-53.

Krise, Jeffrey et al., Prodrugs of Phosphates, Phosphonates, and Phosphinates, Adv. Drug Deliv. Rev. 1996, 19(2), 287-310.

Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. 2001;49(6):783-9.

Kubin, R. F. et al., Fluorescence Quantum Yields of Some Rhodamine Dyes, Luminescence 1982, 27, 455-462.

Kubler-Kielb, J. et al., A New Method for Conjugation of Carbohydrates to Proteins Using an Aminooxy-Thiol Heterbifunctional Linker, J Org Chem 2005, 70, 6987-6990.

Kudo et al., "Up-regulation of a set of glycosyltransferase genes in human colorectal cancer," *Lab. Invest.*, Jul. 1998, 78(7):797-811.

Kwong, Peter et al., Rational Design of Vaccines to Elicit Broadly Neutralizing Antibodies to HIV-I. Cold Spring Harb.Perspect. Med. 1, 2011, 1-16.

Lantz et al., "An invariant T cell receptor a chain is used by a unique subset of major histocompatibility complex class I-specific $CD4^+$ and $CD4^- 8^-$ T cells in mice and humans," *J. Exp. Med.*, Sep. 1, 1994, 180(3):1097-1106.

Lau et al., "N-Glycans in cancer progression," *Glycobiology*, Oct. 2008, 18(10):750-760.

Lau, K. et al. Highly efficient chemoenzymatic synthesis of β1-4-linked galactosides with promiscuous baterial β1-4-galactosyltransferases. Chem. Commun. 46, 6066-6068, (2010).

Le, Mai et al., Avian flu: Isolation of Drug-Resistant H5N1 Virus, Nature, Oct. 20, 2005, 437(7062):1108.

Lebens et al., Mucosal vaccines based on the use of cholera toxin B as immunogen and antigen carrier, *Dev. Biol. Stand.*, 1994, 82:215-227.

Le Droumaguet, C. et al., Fluorogenic Click Reaction., Chem. Soc. Rev. 2010, 39, 1233-1239.

Lederman et al., A single amino acid substitution in a common African allele of the CD4 molecule ablates binding of the monoclonal antibody, OKT4, Molecular Immunology, 28, 1171-1181 (1991).

Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.

Lee et al., "Bivalent antibody phage display mimics natural immunoglobulin," *J. Immunol. Methods*, Jan. 2004, 284(1-2):119-132.

Lee et al., "High-affinity human antibodies from phage-displayed synthetic Fab libraries with a single framework scaffold," *J. Mol. Biol.*, Jul. 23, 2004, 340(5):1073-1093.

Lee et al., A new Solvent System for Efficient Synthesis of 1,2,3-Triazoles, Tetrahedron Lett., Jul. 17, 2006, 47(29):5105-5109.

Lee et al., An Efficient and Practical Method for the Synthesis of Mono-N-Protected α,ω-diaminoalkanes, Tetrahedron Lett., Apr. 2, 2001, 42(14):2709-2711.

Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.

Lee et al., Immunogenicity Study of Globo H Analogues with Modification at the Reducing or Nonreducing end of the tumor antigen, J Am Chem Soc, 136: 16844-16853 (2014).

Lefranc et al., "IMGT, the international ImMunoGeneTics database," *Nucleic Acids Res.*, Jan. 1, 1999, 27(1):209-212.

Lehninger, *Biochemistry: The Molecular Basis of Cell Structure and Function*, 2nd ed., 1975, pp. 73-75, Worth Publishers, New York.

Lei, Jianqing et al., Potential antitumor applications of a monoclonal antibody specifically targeting human papilloma virus 16 E749-57 peptide, Microbiology and Immunology, 2012, vol. 56, pp. 456-462.

Lemieux, R. U. et al., Halide ion catalyzed glycosidation reactions. Syntheses of a-linked disaccharides. J Am. Chem. Soc. 97(14), 4056-62, (1975).

Leung et al., "A method for random mutagenesis of a defined DNA segment using a modified polymerase chain reaction," *Technique—A Journal of Methods in Cell and Molecular Biology*, Aug. 1989, 1(1):11-15.

Lew et al., Discovery and Development of GS 4104 (oseltamivir): an Orally Active Influenza Neuraminidase Inhibitor, Curr Med Chem, Jun. 2000, 7(6):663-672.

Li et al., β-endorphin omission analogs: Dissociation of Immunoreactivity from other biological activities, Proc Natl Avad Sci USA, 77:3211-3214 (1980).

Li, Y. L. et al., Crystallization and Melting Behaviors of PPC-BS/PVA Blends, 19, 1557-1566, 2003.

Li, Henghui et al., MALDI-MS Analysis of Sialylated N-Glycan Linkage Isomers Using Solid-Phase Two Step Derivatization Method, Analytica Chimica Acta 924 (2016) 77-85.

Li et al., "Design of a potent CD1d-binding NKT cell ligand as a vaccine adjuvant," *Proc. Natl. Acad. Sci. USA*, Jul. 20, 2010, 107:13010-13015.

Li, J.; Hu, M.; Yao, S. Q. "Rapid synthesis, screening, and identification ofxanthone and xanthene-based fluorophores using click chemistry." Org. Lett. 2009, 11, 3008-3011.

Li, Lingling, et al., "Syntheses and spectral properties of functionalized, water-soluble Bodipy derivatives." J. Org. Chem. 2008, 73, 1963-1970.

Li, L. et al. Efficient chemoenzymatic synthesis of an N-glycan isomer library. Chem. Sci. 6, 5652-5661 (2015).

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Liang et al., "Quantitative microarray analysis of intact glycolipid-Cd1d interaction and correlation with cell-based cytokine production," *J. Am. Chem. Soc.*, Sep. 17, 2008, 130(37):12348-12354.

Liang, P. H., Wang, S. K. & Wong, C. -H. Quantitative analysis of carbohydrate-protein interactions using glycan microarrays: Determination of surface and solution dissociation constants. J. Am. Chem. Soc. 129, 11177-11184, (2007).

Liang, Chi-Hui et al., Iron Oxide/Gold Core/Shell Nanoparticles for Ultrasensitive Detection of Carbohydrate-Protein Interactions, Anal. Chem. 2009; 81, 7750-7756.

Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.

Lin et al., A common glycan structure on immunoglobulin G for enhancement of effector functions, PNAS, Aug. 25, 2015, vol. 112, No. 34, p. 10611-10616.

(56) References Cited

OTHER PUBLICATIONS

Lindmark et al., "Binding of immunoglobulins to protein A and immunoglobulin levels in mammalian sera," *J. Immunol. Meth.*, Aug. 12, 1983, 62(1):1-13.

Liu C, et al., "Expansion of spleen myeloid suppressor cells represses NK cell cytotoxicity in tumor-bearing host" *Blood.* May 15, 2007;109(10):4336-42. Epub Jan. 23, 2007.

Liu et al., "Activity-based protein profiling: the serine hydrolases," *Proc. Natl. Acad. Sci. USA*, Dec. 21, 1999, 96(26):14694-14699.

Liu et al., "Eradication of large colon tumor xenografts by targeted delivery of maytansinoids," *Proc. Natl., Acad. Sci. U.S.A.*, Aug. 6, 1996, 93(16):8618-8623.

Liu et al., Enhanced anti-influenza agents conjugated with anti-inflammatory activity. J Med Chem. Oct. 11, 2012;55(19):8493-501.

Liu et al., Intramolecular ion-pair prodrugs of znamivir nad guanidino-oseltamivir. Bioorganic & Medicinal Chemistry. Jun. 2011; 19(16):4796-4802.

Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.

LoBuglio et al., "Mouse/human chimeric monoclonal antibody in man: kinetics and immune response," *Proc. Natl. Acad. Sci. U.S.A.*, Jun. 1989, 86(11):4220-4224.

Lode et al., "Targeted therapy with a novel enediyene antibiotic calicheamicin $\Theta^I1$ effectively suppresses growth and dissemination of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Lopes, J.F. et al., Simulataneous Chromatographic Separation of Enantiomers, Anomers and Structural Isomers of Some Biologically Relevant Monsaccharides. J. Chomatogr. A, (2008) 1188:34-42.

Lou, et al., Stage-specific embryonic antigent-4 as a potential therapeutic target in glioblastoma multiforms and other cancers. Proc Natl Acad Sci USA 2014, 111(7):2482-7.

Loudet, A.; Burgess, K. "Bodipy dyes and their derivatives: syntheses and spectroscopic properties." Chem. Rev. 2007, 107, 4891-4932.

Louis et al., "The 2007 WHO classification of tumours of the central nervous system," *Acta. Neuropathol.*, Aug. 2007, 114(2):97-109.

Lu et al., "Design of a mechanism-based probe for neuraminidase to capture influenza viruses," *Angew. Chem. Int. Ed. Engl.*, Oct. 28, 2005, 44(42):6888-6892.

Lu, Guokai et al., Reactivity-Based One-Pot Synthesis of Immunosuppressive Glycolipids From the Caribbean Sponge Plakortis Simplex, J. Chem. 2009, 27, 2217-2222.

Lu et al., "Single chain anti-c-Met antibody conjugated nanoparticles for in vivo tumor-targeted imaging and drug delivery," *Biomaterials*, Apr. 2011, 32(12):3265-3274.

MacBeath, G. and Schreiber, S. L., Printing Proteins as Microarrays for High-Throughput Function Determination, Science, 289, 1760-1763, 2000.

Macfarlane GT, et al., "Formation of glycoprotein degrading enzymes by Bacteroides fragilis" *FEMS Microbiol Lett.* Jan. 15, 1991;61(2-3):289-93.

Makino et al., Predominant expression of invariant $V_\alpha 14^+$ TCR α chain in NK1.1$^+$ T cell populations, *Int. Immunol.*, Jul. 1995, 7(7):1157-1161.

Mandler., et al "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marcato et al., "Chapter 17: The Rocky Road from Cancer Stem Cell Discovery to Diagnostic Applicability," Cancer Stem Cells Theories and Practice, pp. 335-360, Mar. 22, 2011.

Marks et al., "By-passing immunization. Human antibodies from V-gene libraries displayed on phage," *J. Mol. Biol.*, Dec. 5, 1991, 222(3):581-597.

Marks et al., "By-passing immunization: Building high affinity human antibodies by chain shuffling," *Nature Biotechnology*, Jul. 1992, 10(7):779-783.

Massart, R., IEEE Transactions on Magnetics, 17, 1247 (1981).

Masuko, T. et al., Thiolation of Chitosan. Attachment of Proteins Via Thioether Formation, Biomacromolecules 2005, 6, 880-884.

Mather et al., "Culture of testicular cells in hormone-supplemented serum-free medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.

Matsuda et al., "Structure and physical map of 64 variable segments in the 3' 0.8-megabase region of the human immunoglobulin heavy-chain locus," *Nature Genet.*, Jan. 1993, 3(1):88-94.

Matz et al., "Fluorescent proteins from nonbioluminescent *Anthozoa* species," *Nat. Biotechnol.*, Oct. 1999, 17(10):969-973.

McCafferty et al., "Phage antibodies: Filamentous phage displaying antibody variable domains," *Nature*, Dec. 6, 1990, 348:552-554.

McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.

McKimm-Breschkin, "Resistance of influenza viruses to neuraminidase inhibitors—a review," Antiviral Res., Jul. 2000, 47(1): 1-17.

McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Medelson et al., NKp46 O-glycan Sequences that are involved in the interaction with Hemagglutinin Type 1 of Influenza Virus. J. Virol. Feb. 10, 2010, 84(8):3789-3797.

McLellan, J. S. et al. Structure of HIV-I gp120 V1/V2 domain with broadly neutralizing antibody PG9. Nature 480, 336-343, 2011.

Merck, MAB4304, Anti-Stage-Specific Embryonic Antigen-4 Antibody, Clone MC-813-70, 4 Pages, 2017.

Meyer, "Malignant gliomas in adults," *N. Engl. J. Med.*, Oct. 23, 2008, 359(17):1850.

Milstein, C & Cuello, AC, Hybrid Hydridomas and their use in immunohistochemistry, Nature 305, 537-540, Oct. 1993.

Mimura et al., "Role of oligosaccharide residues of IgG1-Fc in FcγRIIb binding," *J. Biol. Chem.*, Dec. 7, 2001, 276(49):45539-45547.

(56) References Cited

OTHER PUBLICATIONS

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," Cancer Res., Jul. 15, 2001, 61(14):5349-5354.
Miyagi et al., "Mammalian sialidases: Physiological and pathological roles in cellular functions," Glycobiology, Jul. 2012, 22(7):880-896.
Miyagi et al., "Plasma membrane-associated sialidase as a crucial regulator of transmembrane signalling," J. Biochem., Sep. 2008, 144(3):279-285.
Miyagi et al., "Sialidase and malignancy: a minireview," Glycoconj. J., 2004, 20(3):189-198.
Miyagi, "Aberrant expression of sialidase and cancer progression," Proc. Jpn. Acad. Ser. B. Phys. Biol. Sci., 2008(10), 84:407-418.
Miyaji, E. N. et al., Induction of Neutralizing Antibodies Against Diphtheria Toxin by Priming with Recombinant Mycobacterium bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," Nature, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," Adv. Carbohydr. Chem. Biochem., 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", Review in Current Analytical Chemistry, vol. 1, No. 1 (2005), pp. 29-57.
Mori K, et al., "Non-fucosylated therapeutic antibodies: the next generation of therapeutic antibodies" Cytotechnology. Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," Proc. Natl. Acad. Sci. U.S.A., Nov. 1984, 81(21):6851-6855.
Morrison, "Immunology. Success in specification," Nature, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," Immunol. Today, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," Anal. Biochem., Sep. 1, 1980, 107(1):220-239.

Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," Nature, Dec. 13-19, 1984, 312(5995):604-608.
Neuberger, "Generating high-avidity human Mabs in mice," Nature Biotechnol., Jul. 1996, 14(7):826.
Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I_1$: A rationally designed molecule with extremely potent and selective DNA cleaving properties and apoptosis inducing activity," Angew. Chem. Intl. Ed. Engl., Feb. 1, 1994, 33(2):183-186.
Niculescu-Duvaz et al., "Antibody-directed enzyme prodrug therapy (ADEPT): A review," Adv. Drg. Del. Rev., Jul. 7, 1997, 26(2-3):151-172.
Nieuwenhuis et al., "CD1d-dependent macrophage-mediated clearance of Pseudomonas aeruginosa from lung," Nat. Med., Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Noto et al., "CD44 and SSEA-4 positive cells in an oral cancer cell line HSC-4 possess cancer stem-like cell characteristics," Oral Oncol., Aug. 2013, 49(8):787-795.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," Proc. Natl. Acad. Sci. USA, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," Immunity, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," Adv. Immunol., 1998, 70:281-312.
Olden, Kenneth et al., Carbohydrate Moieties of Glycoproteins: A Re-Evaluation of Their Function, Biochem et Biophys Acta 650:209-232 (1982).
Orlandi et al., "Cloning immunoglobulin variable domains for expression by the polymerase chain reaction," Proc. Natl. Avad. Sci. U.S.A., May 1989, 86(10):3833-3837.
Ørum et al., "Efficient method for constructing comprehensive murine Fab antibody libraries displayed on phage." Nucleic Acids Res., Sep. 25, 1993, 21(19):4491-4498.
Otsubo N, et al., An Efficient and Straightforward Synthesis of Sialyl Lex Glycolipid as a Potent Selectin Blocker[[1]], Carbohydr. Res. 1998, 306, 517-530.

(56) References Cited

OTHER PUBLICATIONS

Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Papanastassiou et al., "The potential for efficacy of the modified (ICP 34.5⁻) herpes simplex virus HSV1716 following intratumoural injection into human malignant glioma: a proof of principle study," Gene Therapy, Mar. 2002, 9(6):398-406.
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," *Biochemistry*, Jan. 16, 2007, 46(2):350-358.
Paulson, J. C., Blixt, 0. & Collins, B. E. Sweet spots in functional glycomics. Nat. Chem. Biol. 2, 238-248, (2006).
Pearlman et al., *Peptide and Protein Drug Delivery, Chapter 6: Analysis of Protein Drugs*, Lee, ed., 1991, pp. 247-301, Marcel Dekker Publishing, New York.
Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.
Peipp et al., "Antibody fucosylation differentially impacts cytotoxicity mediated by NK and PMN effector cells," *Blood*, 2008, 112(6):2390-2399.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).

Piizi, G. and Hardinger, S., Stereochemistry: an Introduction, UCLA Chemistry 30A Presentation, Fall 2002, in 40 pages.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.
Poloukhtine et al., "Selective labeling of living cells by a photo-triggered click reaction," *J. Am. Chem. Soc.*, Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res*. Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.

(56) References Cited

OTHER PUBLICATIONS

Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).

Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Sell, "Cancer-associated carbohydrates identified by monoclonal antibodies," *Hum. Pathol.*, Oct. 1990, 21(10):1003-1019.
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.

(56) References Cited

OTHER PUBLICATIONS

Shie, Jiun-Jie et al., "A concise and flexible synthesis of the potent anti-influenza agents tamiflu and tamiphosphor," Angew. Chem. Int. Ed Engl., 2008, 47(31):5788-5791.

Shie, Jiun-Jie et al., An Azido-BODIPY Probe for Glycosylation: Initiation of Strong Fluorescence Upon Triazole Formation, J. Am. Chem. Soc. 2014, 136, 9953-9961.

Shieh, Peyton et al., Fluorogenic Azidofluoresceins for Biological Imaging, J. Am. Chem. Soc. 2012, 134, 17428-17431.

Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.

Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.

Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).

Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.

Shriver, Zachary et al., Glycomics: a Pathway to a Class of New and Improved Therapeutics, Nat Rev Drug Disc, 2004, 3, 863-873.

Sidhu et al., "Phage-displayed antibody libraries of synthetic heavy chain complementarity determining regions," *J. Mol. Biol.*, Apr. 23, 2004, 338(2):299-310.

Siebenlist et al., "*E. coli* RNA polymerase interacts homologously with two different promoters," *Cell*, Jun. 1980, 20(2):269-281.

Sieber et al., "Proteomic profiling of metalloprotease activities with cocktails of active-site probes," *Nat. Chem. Biol.*, May 2006, 2(5):274-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Sivakumar, Krishnamoorthy et al., "A fluorogenic 1,3-dipolar cycloaddition reaction of 3-azidocoumarins and acetylenes." Org. Lett. 2004,24, 4603-4606.

Skehel, John et al., Receptor Binding and Membrane Fusion in Virus Entry: The Influenza Hemagglutinin, Ann. Rev Biochem, 69:531, 2000.

Skerra, "Bacterial expression of immunoglobulin fragments," *Curr. Opinion in Immunol.*, Apr. 1993, 5(2):256-262.

Slamon DJ, et al., Human breast cancer: correlation of relapse and survival with amplification of the HER-2/neu oncogene, *Science*. Jan. 9, 1987; 235(4785):177-82.

Sletten et al., "Bioorthogonal Chemistry: Fishing for Selectivity in a Sea of Functionality," *Angew. Che. Int. Ed. Engl.*, Aug. 27, 2009, 48(38):6974-6998.

Smith RA et al., "The active form of tumor necrosis factor is a trimer" *J Biol Chem.* May 25, 1987;262(15):6951-4.

Smyth MJ, et al., "CD4+CD25+ T regulatory cells suppress NK cell-mediated immunotherapy of cancer" *J Immunol.* Feb. 1, 2006;176(3):1582-7.

Sok, Devin et al., SnapShot: Broadly Neutralizing Antibodies. Cell 155, 728-728, (2013).

Solomons, G. and Fryhle, C., Chapter 5 Titled, Stereochemistry: Chiral Molecules, p. 184-228, in "Organic Chemistry," 7th Edition, Wiley, Jun. 18, 2001.

Soriano del Amo, David et al. Chemoenzymatic synthesis of the sialyl Lewis X glycan and its derivatives. Carbohydr. Res. 345, 1107-13, (2010).

Spinosa, Maria Rita et al., The Neisseria Meningitidis Capsule is Important for Intracellular Survival in Huamn Cells, Infect Immun 2001, 75, 3594-3603.

Srinivasan, Quantitative et al., Biochemical Rationale for Differences in Transmissibility of 1918 Pandemic Influenza A Viruses, Proc. Natl. Acad. Sci., 105, 2800-2805, 2008.

Stein, K.E. et al., The Immune Response to an Isomaltohexosyl-Protein Conjugate, a Thymus-Dependent Analogue of Alpha(1 Replaced By 6) Dextran., J Immunol 1982, 128, 1350-1354.

Stein, K.E., Thymus-Independent and Thymus-Dependent Responses to Polysaccharide Antigens, J Infect Dis 1992, 165 Suppl 1, S49-52.

Stephens, David, Conquering the Meningococcus, FEALS Microbial Rev 2007, 31, 3-14.

Stephens, D.S. et al., Epidemic Meningitis, Meningococcaemia, and Neisseria Meningitidis, Lancet 2007, 369, 2196-2210.

Stephenson et al., "Neuraminidase inhibitor resistance after oseltamivir treatment of acute influenza A and B in children," Clin. Infect. Dis., Feb. 15, 2009, 48(4):389-396.

Stevanovic, Stefan, Identification of Tumour-Associated T-Cell Epitopes for Vaccine Development, Nat. Rev. Cancer, 2002, 2, 514-520.

Stevens, James et al., Structure of the Uncleaved Human H1 Hemagglutinin From the Extinct 1918 Influenza Virus, Science, 303:1866, 2004.

Stevens, James et al., Structure and Receptor Specificity of the Hemagglutinin From an H5N1 Influenza Virus, Science, 312:404, 2006.

Stevens et al., Glycan Microarray Analysis of the Hemagglutinins From Modern and Pandemic Influenza Viruses Reveals Different Receptor Specificities. Journal of Molecular Biology 355.5 (2006): 1143-1155.

Stickings, Paul et al., Transcutaneous Immunization with Cross-Reacting Material CRM197 of Diphtheria Toxin Boosts Functional Antibody Levels in Mice Primed Parenterally with Adsorbed Diphtheria Toxoid Vaccine, Infection and Immunity, 2008, 76, 1766-1773.

Stockmann, H. et al., Development and Evaluation of New Cyclootynes for Cell Surface Glycan Imaging in Cancer Cells, J. Chem. Sci. 2011, 2, 932-936.

Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.

Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.

Su, G. Hahner, W. Zhou "Investigation of the pore formation in anodic aluminum oxide" J Mater. Chem. 2008, 18 5787-5795.

Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).

Supplementary European Search Report in European Application No. EP 13775664.9, dated Oct. 27, 2015, in 7 pages.

Suresh et al., "Bispecific monoclonal antibodies from hybrid hybridomas," *Methods in Enzymology*, 1986, 121:210-228.

Sutton, VR et al., Bcl-2 Prevents Apoptosis Induced by Perforin and Granzyme B, But Not That Mediated by Whole Cytotoxic Lymphocytes, J of Immunology 1997, 158(12), 5783.

Suzuki E, et al., "A nonfucosylated anti-HER2 antibody augments antibody-dependent cellular cytotoxicity in breast cancer patients" *Clin Cancer Res.* Mar. 15, 2007;13(6):1875-82.

Svennerholm et al., "Human brain gangliosides: Developmental changes from early fetal stage to advanced age," *Biochim. Biophys. Acta*, Sep. 25, 1989, 1005(2):109-117.

Syrigos et al., "Antibody directed enzyme prodrug therapy (ADEPT): a review of the experimental and clinical considerations," *Anticancer Research*, Jan.-Feb. 1999, 19(1A):605-614.

(56) References Cited

OTHER PUBLICATIONS

Tahir et al., "Loss of IFN-γ production by invariant NK T cells in advanced cancer," J. Immunol., Oct. 1, 2001, 167(7):4046-4050.
Takakura, Yoshimitsu et al., Molecular cloning, expression and properties of an alpha/beta-Galactoside alpha 2,3-sialyltransferase from Vibrio sp. JT- FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Takeda et al., "Construction of chimaeric processed immunoglobulin genes containing mouse variable and human constant region sequences," Nature, Apr. 4-10, 1985, 314(6010):452-454.
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Taylor-Papadimitriou et al., "Exploiting altered glycosylation patterns in cancer: Progress and challenges in diagnosis and therapy," Trends Biotechnol., Jun. 1994, 12(6):227-233.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thorpe, (1985) "Antibody Carriers of Cytotoxic Agents in Cancer Therapy: A Review," in Monoclonal Antibodies '84: Biological and Clinical Applications, A. Pinchera et al. (ed.s), pp. 475-506.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," J. Mol. Biol., Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," EMBO J., Dec. 1991, 10(12):3655-3659.
Traylor et al., "Gangliosides of human cerebral astrocytomas," J. Neurochem., Jan. 1980, 34(1):126-131.
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai et al., "Design and synthesis of activity probes for glycosidases," Org. Lett., Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai Ti, et al., "Effective sugar nucleotide regeneration for the large-scale enzymatic synthesis of Globo H and SSEA4" J Am Chem Soc. Oct. 2, 2013;135(39):14831-9, Epub Sep. 17, 2013.

Tsai, Tsung-I et al., An Effective Bacterial Ducosidase for Glycoprotein Remodeling, ACS Chemical Biology, vol. 12, No. 1, Jan. 20, 2017, pp. 63-72.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')₃ derivatives that use cooperative signaling via the TCR/CD3 complex and CD2 to activate and redirect resting cytotoxic T cells," J. Immunol., Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" Glycobiology. Jan. 1996;6(1):83-93.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Urlaub et al., "Isolation of Chinese hamster cell mutants deficient in dihydrofolate reductase activity." Proc. Natl. Acad. Sci. U.S.A., Jul. 1980, 77(7):4216-4220.
Valentine MA, et al., "Phosphorylation of the CD20 phosphoprotein in resting B lymphocytes. Regulation by protein kinase C" J Biol Chem. Jul. 5, 1989;264(19):11282-7.
Van Beek et al., "Increased sialic acid density in surface glycoprotein of transformed and malignant cells—a general phenomenon?" Cancer Res., Nov. 1973, 33(11):2913-2922.
Van der Horst et al., "Photoaffinity labeling of a bacterial sialidase with an aryl azide derivative of sialic acid," J. Biol. Chem., Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," CA Cancer J. Clin., May-Jun. 2010, 60(3):166-193.
Van Slambrouck et al., "Clustering of monosialyl-Gb5 initiates downstream signalling events leading to invasion of MCF-7 breast cancer cells," Biochem. J., Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," Nature, Apr. 26, 2007, 446(7139):1023-1029.
Vasella et al., "Synthesis of a phosphoric acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," Ann. Allergy, Asthma Immunol., Aug. 1998, 81(2):105-116, 119.
Vavricka, Christopher et al., Influenza Neuraminidase Operates Via a Nucleophilic Mechanism and Can Be Targeted by Covalent Inhibitors, Nature Communcations, 4:1491 (2013).

(56) References Cited

OTHER PUBLICATIONS

Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, Es et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of Bodipy Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "Glycan microarray of Globo H and related structures for quantitative analysis of breast cancer," *Proc. Natl. Acad. Sci. U.S.A.*, Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).

Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from *Escherichia coli,*" *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "Trypanosoma cruzi trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the lgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," *Cancer Metastasis Rev.*, 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." *Eur. J. Immunol.*, Jul. 1993, 23(7):1456-1461.
Wiltshire, S. et al. Proc. Natl. Acad. Sci. (2000) 97, 10113-10119.
Winter et al., "Making antibodies by phage display technology," *Annu. Rev. Immunol.*, 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woof et al., "Human antibody-Fc receptor interactions illuminated by crystal structures," *Nat. Rev. Immunol.*, Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).

(56) References Cited

OTHER PUBLICATIONS

Wu et al., "Avidity of CD1d-ligand-receptor ternary complex contributes to T-helper 1 (Th1) polarization and anticancer efficacy," *Proc. Nmi Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in *Escherichia coli,*" *Methods: A Companion to Methods in Enzymol.*, Aug. 1992, 4(2):151-158.
Yates AJ et al., Brain Tumors in Childhood. Childs Brain 5(1), 31-39 (1979).
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of Gm1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "New cerebrosides from Acanthopanax gracilistylus," Caplus 156:225776 (2011).
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zhang et al., "Selection of tumor antigens as targets for immune attack using immunohistochemistry: I. Focus on gangliosides," *Int. J. Cancer*, Sep. 26, 1997, 73(1):42-49.

Zheng et al., Delayed antiviral plus immunomodular treatment still reduces mortality in mice infected by high inoculum on influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
Cheung et al., Meeting Info: 23rd International Symposium on Glycoconjugates, Glyco 23. Split, Croatia. Sep. 15, 2015-Sep. 20, 2015, vol. 32, No. 5, pp. 323.
Tsai, Charng-Sheng et al., Cell-Permeable Probe for Identification and Imaging of Sialidases, PNAS, vol. 110, No. 7, 2013, 2466-2471.
Al-Hajj, Muhammad, et al. "Prospective identification of tumorigenic breast cancer cells." Proceedings of the National Academy of Sciences 100.7 (2003): 3983-3988.
Almagro, Juan C., and Johan Fransson. "Humanization of antibodies." Front Biosci 13.1 (2008): 1619-1633.
Beck, Benjamin, and Cédric Blanpain. "Unravelling cancer stem cell potential." Nature Reviews Cancer 13.10 (2013): 727.
Bomken, S., et al. "Understanding the cancer stem cell." British journal of cancer 103.4 (2010): 439-445.
Clarke, Michael F., and Andrew T. Hass. "Cancer stem cells." Reviews in Cancer Res. (2006) 66(19):9339-9344.
De Genst, Erwin, et al. "Antibody repertoire development in camelids." Developmental & Comparative Immunology 30.1-2 (2006): 187-198.
De Leoz, Maria Lorna A., et al. "High-mannose glycans are elevated during breast cancer progression." Molecular & Cellular Proteomics 10.1 (2011): M110-002717, 9 pages; https://doi.org/10.1074/mcp.M110.002717.
Danishefsky, Samuel J., et al. "Development of Globo-H cancer vaccine." Accounts of Chemical Research 48.3 (2015): 643-652.
Dorner, Brigitte G., et al. "MIP-1a, MIP-1 β, Rantes, and ATAC/lymphotactin function together with IFN-? as type 1 cytokines." Proceedings of the National Academy of Sciences 99.9 (2002): 6181-6186.
Fuster, Mark M., and Jeffrey D. Esko. "The sweet and sour of cancer: glycans as novel therapeutic targets." Nature Reviews Cancer 5.7 (2005): 526-542.
Gao, Jingqing, Dianjun Liu, and Zhenxin Wang. "Microarray-based study of carbohydrate-protein binding by gold nanoparticle probes." Analytical chemistry 80.22 (2008): 8822-8827.
Ghaderi, Darius, et al. "Production platforms for biotherapeutic glycoproteins. Occurrence, impact, and challenges of non-human sialylation." Biotechnology and Genetic Engineering Reviews 28.1 (2012): 147-176.
Ginestier, Christophe, et al. "ALDH1 is a marker of normal and malignant human mammary stem cells and a predictor of poor clinical outcome." Cell stem cell 1.5 (2007): 555-567.
Hakomori, S., and W. W. Young Jr. "Tumor-associated glycolipid antigens and modified blood group antigens." Scandinavian Journal of Immunology 7 (1978): 97-117.
Hakomori, Sen-itiroh. "Aberrant glycosylation in cancer cell membranes as focused on glycolipids: overview and perspectives." Cancer research 45.6 (1985): 2405-2414.
Harvey, David J. "Matrix-assisted laser desorption/ionization mass spectrometry of sphingo- and glycosphingo-Lipids." Journal of Mass Spectrometry 30.9 (1995): 1311-1324.
Hwang-Verslues, Wendy W., et al. "Multiple lineages of human breast cancer stem/progenitor cells identified by profiling with stem cell markers." PloS one 4.12 (2009): e8377.
Intra, Jari, et al. "Comparative and phylogenetic analysis of α-l-fucosidase genes." Gene 392.1-2 (2007): 34-46.

(56) References Cited

OTHER PUBLICATIONS

Jordan, et al. "Cancer stem cells." N Engl J Med 355.12 (2006): 1253-1261.

Liang, Chi-Hui, et al. "Effects of neighboring glycans on antibody-carbohydrate interaction." Angewandte Chemie International Edition 50.7 (2011): 1608-1612.

Lingwood, Daniel, et al. "Cholesterol modulates glycolipid conformation and receptor activity." Nature chemical biology 7.5 (2011): 260-262.

Listinsky, Jay J., et al "Glycoengineering in cancer therapeutics: a review with fucose-depleted trastuzumab as the model." Anti-cancer drugs 24.3 (2013): 219-227.

Lloyd et al "Modelling the human immune response: performance of a 1011 human antibody repertoire against a broad panel of therapeutically relevant antigens" Protein Eng Des Sel. Mar. 2009;22(3):159-68. doi: 10.1093/protein/gzn058. Epub Oct. 29, 2008.

Novak, Anton, et al. "Cholesterol masks membrane glycosphingolipid tumor-associated antigens to reduce their immunodetection in human cancer biopsies." Glycobiology 23.11 (2013): 1230-1239.

Office Action dated Oct. 26, 2018, from corresponding Chinese Patent Application No. 201680006858.6, 13 total pages.

Package insert for human-type human TNF-alpha monoclonal antibody preparation, Humira, subcutaneous injection 40 mg, 2009, p. 1-7; Machine translation provided.

Partial European Search Report dated Jun. 13, 2018 in EP application 16740906.9, 14 pages.

Pece, Salvatore, et al. "Biological and molecular heterogeneity of breast cancers correlates with their cancer stem cell content." Cell 140.1 (2010): 62-73.

Q5LAD6 ver 52, Definition: Bacteroides fragilis (strain ATCC 25285/NCTN 9343), UniProtKB/TrEMBL [online], May 14, 2014, URL at http://www.uniprot.org/uniprot/Q5LAD6.txt?version=52; downloaded Feb. 8, 2019, 19 pages.

Rajan, Valanila P., et al. "A cloned human DNA restriction fragment determines expression of a GDP-L-fucose: beta-D-galactoside 2-alpha-L-fucosyltransferase in transfected cells. Evidence for isolation and transfer of the human H blood group locus." Journal of Biological Chemistry 264.19 (1989): 11158-11167.

Rouquier, Sylvie, et al. "Molecular cloning of a human genomic region containing the H blood group a (1, 2) fucosyltransferase gene and two H locus-related DNA restriction fragments isolation of a candidate for the human secretor blood group locus." Journal of Biological Chemistry 270.9 (1995): 4632-4639.

Shaw, Frances L., et al. "A detailed mammosphere assay protocol for the quantification of breast stem cell activity." Journal of mammary gland biology and neoplasia 17.2 (2012): 111-117.

Stanley, Pamela, and Richard D. Cummings. "Chapter 13. Structures common to different glycans." Essentials of Glycobiology [Internet]. 2nd edition. Cold Spring Harbor Laboratory Press (NY), 2009; NCBI Bookshelf, retrieved from the internet on Aug. 17, 2017, 40, pages.

Tripp, Ralph A., et al. "Bioconjugated nanoparticle detection of respiratory syncytial virus infection." International Journal of Nanomedicine 2(1) (2007): 117-124.

Tsai, H. H., C. A. Hart, and J. M. Rhodes. "Production of mucin degrading sulphatase and glycosidases by Bacteroides thetaiotaomicron." Letters in Applied Microbiology 13.2 (1991): 97-101.

Wright, Mollie H., et al. "Brca1 breast tumors contain distinct CD44+/CD24− and CD133+ cells with cancer stem cell characteristics." Breast Cancer Research 10.1 (2008): R10.

Zhou, Dapeng, et al. "The β1, 3-galactosyltransferase β3GalT-V is a stage-specific embryonic antigen-3 (SSEA-3) synthase." Journal of Biological Chemistry 275.30 (2000): 22631-22634.

\* cited by examiner

FIG. 1A

The CDRs of representative anti-SSEA4 antibody chAb6 in Kabat, AbM, Chothia, Contact, and IMGT method, respectively

H-CDR1

| Method | Definition | Sequence |
|---|---|---|
| Kabat | H31-H35B | NYGVS |
| AbM | H26-H35 | GFSLKNYGVS |
| Chothia | H26-H32...H34 | GFSLKNY[GV] |
| Contact | H30-H35 | KNYGVS |
| IMGT | Online prediction | GFSLKNYG |

H-CDR2

| Method | Definition | Sequence |
|---|---|---|
| Kabat | H50-H65 | VIWGDGSTNYHSTLRS |
| AbM | H50-H58 | VIWGDGSTN |
| Chothia | H52-H56 | WGDGS |
| Contact | H47-H58 | WLGVIWGDGSTN |
| IMGT | Online prediction | IWGDGST |

H-CDR3

| Method | Definition | Sequence |
|---|---|---|
| Kabat | H95-H102 | PGAGYAMDY |
| AbM | H95-H102 | PGAGYAMDY |
| Chothia | H95-H102 | PGAGYAMDY |
| Contact | H93-H101 | AKPGAGYAMD |
| IMGT | Online prediction | AKPGAGYAMDY |

L-CDR1

| Method | Definition | Sequence |
|---|---|---|
| Kabat | L24-L34 | SASSSVSYMH |
| AbM | L24-L34 | SASSSVSYMH |
| Chothia | L24-L34 | SASSSVSYMH |
| Contact | L30-L36 | VSYMHWY |
| IMGT | Online prediction | SSVSY |

L-CDR2

| Method | Definition | Sequence |
|---|---|---|
| Kabat | L50-L56 | DTSKLTS |
| AbM | L50-L56 | DTSKLTS |
| Chothia | L50-L56 | DTSKLTS |
| Contact | L46-L55 | LWIYDTSKLT |
| IMGT | Online prediction | DTS |

L-CDR3

| Method | Definition | Sequence |
|---|---|---|
| Kabat | L89-L97 | FQGSGYPLT |
| AbM | L89-L97 | FQGSGYPLT |
| Chothia | L89-L97 | FQGSGYPLT |
| Contact | L89-L96 | FQGSGYPL |
| IMGT | Online prediction | FQGSGYPLT |

FIG. 1B

Heavy Chain

```
                              H-CDR1              H-CDR2
chAb6     QVQLKESGPGLVAPSQSLSITCTVSGFSLKNYGVSWVRQPPGKGLEWLGVIWGDGSTNYH
hAb6-3.1  QVQLQESGPGLVAPSQTLSITCTVSGFSLKNYGVSWVRQPPGKGLEWIGVIWGDGSTNYH
                              H-CDR3
chAb6     STLRSRLTISKDNSKSQLFLKLNRLQTDDTATYYCAKPGAGYAMDYWGQGTSVTVSS
hAb6-3.1  STLRSRVTISKDNSKSQLFLKLNRLQTDDTATYYCAKPGRGYAMDYWGQGTLVTVSS
```

Light Chain

```
                              L-CDR1              L-CDR2
chAb6     QIVLTQSPAIMSVYPGEKVTMTCSASSSVSYMHWYQQKSSTSPKLWIYDTSKLTSGVPGR
hAb6-3.1  EIVLTQSPAIQSVYPGEKVTMTCSASSSVSYMHWYQQKSSTSPKLWIYDTSKLTSGVPGR
                              L-CDR3
chAb6     FSGSGSGNSYSLTISSMEAEDVATYYCFQGSGYPLTFGGGTKLEIKR
hAb6-3.1  FSGSGSGNSYTLTISSMEAEDAATYYCFQGSGYPLTFGGGTKVEIKR
```

FIG. 1C

Heavy chain

```
chAb6    QVQLKESGPGLVAPSQSLSITCTVSGFSLKNYGVSWVRQPPGKGLEWLGVIWDGSTNYH
hAb6-2   QVQLKESGPGLVAPSQTLSITCTVSGFSLKNYGVSWVRQPPGKGLEWLGVIWDGSTNYH
hAb6-3   QVQLQESGPGLVAPSQTLSITCTVSGFSLKNYGVSWVRQPPGKGLEWLGVIWDGSTNYH
```

```
chAb6    STLRSRLTISKDNSKSQLFLKLNRLQTDDTATYYCAKPGAGYAMDYWGQGTSVTVSS
hAb6-2   STLRSRVTISKDNSKSQLFLKLNRLQTDDTATYYCAKPGAGYAMDYWGQGTSVTVSS
hAb6-3   STLRSRVTISKDNSKSQLFLKLNRLQTDDTATYYCAKPGAGYAMDYWGQGTLVTVSS
```

Light chain

```
chAb6    QIVLTQSPAIMSVYPGEKVTMTCSASSSVSYMHWYQQKSSTSPKLWIYDTSKLTSGVPGR
hAb6-2   EIVLTQSPAIQSVYPGEKVTMTCSASSSVSYMHWYQQKSSTSPKLWIYDTSKLTSGVPGR
hAb6-3   EIVLTQSPAIQSVYPGEKVTMTCSASSSVSYMHWYQQKSSTSPKLWIYDTSKLTSGVPGR
```

```
chAb6    FSGSGSGNSYSLTISSMEAEDVATYYCFQGSGYPLTFGGGTKLEIKR
hAb6-2   FSGSGSGNSYTLTISSMEAEDVATYYCFQGSGYPLTFGGGTKLEIKR
hAb6-3   FSGSGSGNSYTLTISSMEAEDAATYYCFQGSGYPLTFGGGTKVEIKR
```

FIG. 1D

Heavy chain

| | |
|---|---|
| hAb6-3 | QVQLQESGPGLVAPSQTLSITCTVSGFSLKNYGVSWVRQPPGKGLEWIGVIWGDGSTNYH |
| hAb6-3.1 | QVQLQESGPGLVAPSQTLSITCTVSGFSLKNYGVSWVRQPPGKGLEWIGVIWGDGSTNYH |
| hAb6-3.2 | QVQLQESGPGLVAPSQTLSITCTVSGFSLKSYGVSWVRQPPGKGLEWIGVIWGDGSTNYH |
| hAb6-3.3 | QVQLQESGPGLVAPSQTLSITCTVSGFSLKNYGVSWVRQPPGKGLEWIGVIWGDGSTNYH |
| hAb6-3.4 | QVQLQESGPGLVAPSQTLSITCTVSGFSLKNYGVSWVRQPPGKGLEWIGVIWGDGSTNYH |

| | |
|---|---|
| hAb6-3 | STLRSRVTISKDNSKSQLFLKLNRLQTDDTATYYCAKPGAGYAMDYWGQGTLVTVSS |
| hAb6-3.1 | STLRSRVTISKDNSKSQLFLKLNRLQTDDTATYYCAKPGRGYAMDYWGQGTLVTVSS |
| hAb6-3.2 | STLRSRVTISKDNSKSQLFLKLNRLQTDDTATYYCAKPGRGYAMDYWGQGTLVTVSS |
| hAb6-3.3 | SALRSRVTISKDNSKSQLFLKLNRLQTDDTATYYCAKPGRGYAMDYWGQGTLVTVSS |
| hAb6-3.4 | STLRSRVTISKDNSKSQLFLKLNRLQTDDTATYYCAKPGRGYAMDYWGQGTLVTVSS |

Light chain

| | |
|---|---|
| hAb6-3 | EIVLTQSPAIQSVYPGEKVTMTCSASSSVSYMHWYQQKSSTSPKLWIYDTSKLTSGVPGR |
| hAb6-3.1 | EIVLTQSPAIQSVYPGEKVTMTCSASSSVSYMHWYQQKSSTSPKLWIYDTSKLTSGVPGR |
| hAb6-3.2 | EIVLTQSPAIQSVYPGEKVTMTCSASSSVSYMHWYQQKSSTSPKLWIYDTSKLTSGVPGR |
| hAb6-3.3 | EIVLTQSPAIQSVYPGEKVTMTCSASSSVSYMHWYQQKSSTSPKLWIYDTSKLTSGVPGR |
| hAb6-3.4 | EIVLTQSPAIQSVYPGEKVTMTCSASSSVSYMHWYQQKSSTSPKLWIYDTYKLTSGVPGR |

| | |
|---|---|
| hAb6-3 | FSGSGSGNSYTLTISSMEAEDAATYYCFQGSGYPLTFGGGTKVEIKR |
| hAb6-3.1 | FSGSGSGNSYTLTISSMEAEDAATYYCFQGSGYPLTFGGGTKVEIKR |
| hAb6-3.2 | FSGSGSGNSYTLTISSMEAEDAATYYCFQGSGYPLTFGGGTKVEIKR |
| hAb6-3.3 | FSGSGSGNSYTLTISSMEAEDAATYYCFQGSGYPLTFGGGTKVEIKR |
| hAb6-3.4 | FSGSGSGNSYTLTISSMEAEDAATYYCFQGSGYPLTFGGGTKVEIKR |

FIG. 1E

Heavy chain

| | |
|---|---|
| hAb6-3 | QVQLQESGPGLVAPSQTLSITCTVSGFSLKNYGVSWVRQPPGKGLEWIGVIWGDGSTNYH |
| hAb6-3.101 | QVQLQESGPGLVAPSQTLSITCTVSGFSLKNYGVSWVRQPPGKGLEWIGAIWGDGSTNYH |
| hAb6-3.103 | QVQLQESGPGLVAPSQTLSITCTVSGFSLKNYGVSWVRQPPGKGLEWIGVIWADGSTNYH |
| hAb6-3.105 | QVQLQESGPGLVAPSQTLSITCTVSGFSLKNYGVTWVRQPPGKGLEWIGVIWGDGSTNYH |
| hAb6-3.106 | QVQLQESGPGLVAPSQTLSITCTVSGFSLKNYGVSWVRQPPGKGLEWIGVIWGDGSTNYH |
| hAb6-3.107 | QVQLQESGPGLVAPSQTLSITCTVSGFSLKNYGVSWVRQPPGKGLEWIGVIWGDGSTNYH |
| hAb6-3.108 | QVQLQESGPGLVAPSQTLSITCTVSGFSLKNYGVSWVRQPPGKGLEWIGVIWGDGSTNYH |
| hAb6-3.110 | QVQLQESGPGLVAPSQTLSITCTVSGFSLKNYGVSWVRQPPGKGLEWIGVIWGDGSTNYH |
| | |
| hAb6-3 | STLRSRVTISKDNSKSQLFLKLNRLQTDDTATYYCAKPGAGYAMDYWGQGTLVTVSS |
| hAb6-3.101 | STLRSRVTISKDNSKSQLFLKLNRLQTDDTATYYCAKPGRGYAMDYWGQGTLVTVSS |
| hAb6-3.103 | STLRSRVTISKDNSKSQLFLKLNRLQTDDTATYYCAKPGRGYAMDYWGQGTLVTVSS |
| hAb6-3.105 | STLRSRVTISKDNSKSQLFLKLNRLQTDDTATYYCAKPGRGYAMDYWGQGTLVTVSS |
| hAb6-3.106 | STLRSRVTISKDNSKSQLFLKLNRLQTDDTATYYCAKPGRGYAMDYWGQGTLVTVSS |
| hAb6-3.107 | STLRSRVTISKDNSKSQLFLKLNRLQTDDTATYYCAKPGRGYAMDYWGQGTLVTVSS |
| hAb6-3.108 | STLRSRVTISKDNSKSQLFLKLNRLQTDDTATYYCAKPGRGYAMDYWGQGTLVTVSS |
| hAb6-3.110 | STLRSRVTISKDNSKSQLFLKLNRLQTDDTATYYCAKPGRGYAMDYWGQGTLVTVSS |

Light chain

| | |
|---|---|
| hAb6-3 | EIVLTQSPAIQSVYPGEKVTMTCSASSSVSYMHWYQQKSSTSPKLWIYDTSKLTSGVPGR |
| hAb6-3.101 | EIVLTQSPAIQSVYPGEKVTMTCSASSSVSYMHWYQQKSSTSPKLWIYDTSKLTSGVPGR |
| hAb6-3.103 | EIVLTQSPAIQSVYPGEKVTMTCSASSSVSYMHWYQQKSSTSPKLWIYDTSKLTSGVPGR |
| hAb6-3.105 | EIVLTQSPAIQSVYPGEKVTMTCSASSSVSYMHWYQQKSSTSPKLWIYDTSKLTSGVPGR |
| hAb6-3.106 | EIVLTQSPAIQSVYPGEKVTMTCSASSSTSYMHWYQQKSSTSPKLWIYDTSKLTSGVPGR |
| hAb6-3.107 | EIVLTQSPAIQSVYPGEKVTMTCSASSSASYMHWYQQKSSTSPKLWIYDTSKLTSGVPGR |
| hAb6-3.108 | EIVLTQSPAIQSVYPGEKVTMTCSASSSVSYMHWYQQKSSTSPKLWIYDTSKLTSGVPGR |
| hAb6-3.110 | EIVLTQSPAIQSVYPGEKVTMTCSASSSVSYMHWYQQKSSTSPKLWIYDTSKLTSGVPGR |
| | |
| hAb6-3 | FSGSGSGNSYTLTISSMEAEDAATYYCFQGSGYPLTFGGGTKVEIKR |
| hAb6-3.101 | FSGSGSGNSYTLTISSMEAEDAATYYCFQGSGYPLTFGGGTKVEIKR |
| hAb6-3.103 | FSGSGSGNSYTLTISSMEAEDAATYYCFQGSGYPLTFGGGTKVEIKR |
| hAb6-3.105 | FSGSGSGNSYTLTISSMEAEDAATYYCFQGSGYPLTFGGGTKVEIKR |
| hAb6-3.106 | FSGSGSGNSYTLTISSMEAEDAATYYCFQGSGYPLTFGGGTKVEIKR |
| hAb6-3.107 | FSGSGSGNSYTLTISSMEAEDAATYYCFQGSGYPLTFGGGTKVEIKR |
| hAb6-3.108 | FSGSGSGNSYTLTISSMEAEDAATYYCFQASGYPLTFGGGTKVEIKR |
| hAb6-3.110 | FSGSGSGNSYTLTISSMEAEDAATYYCFQGSQFPLTFGGGTKVEIKR |

FIG. 2 chAb6

Heavy chain
QVQLKESGPGLVAPSQSLSITCTVSGFSLKNYGVSWVRQPPGKGLEWLGVIWGDGSTNYHST
LRSRLTISKDNSKSQLFLKLNRLQTDDTATYYCAKPGAGYAMDYWGQGTSVTVSS

Light chain
QIVLTQSPAIMSVYPGEKVTMTCSASSSVSYMHWYQQKSSTSPKLWIYDTSKLTSGVPGRFS
GSGSGNSYSLTISSMEAEDVATYYCFQGSGYPLTFGGGTKLEIKR humanized Ab6-2

Heavy chain
QVQLKESGPGLVAPSQTLSITCTVSGFSLKNYGVSWVRQPPGKGLEWIGVIWGDGSTNYHST
LRSRVTISKDNSKSQLFLKLNRLQTDDTATYYCAKPGAGYAMDYWGQGTSVTVSS

Light chain
EIVLTQSPAIQSVYPGEKVTMTCSASSSVSYMHWYQQKSSTSPKLWIYDTSKLTSGVPGRFS
GSGSGNSYTLTISSMEAEDVATYYCFQGSGYPLTFGGGTKLEIKR humanized Ab6-3

Heavy chain
QVQLQESGPGLVAPSQTLSITCTVSGFSLKNYGVSWVRQPPGKGLEWIGVIWGDGSTNYHST
LRSRVTISKDNSKSQLFLKLNRLQTDDTATYYCAKPGAGYAMDYWGQGTLVTVSS

Light chain
EIVLTQSPAIQSVYPGEKVTMTCSASSSVSYMHWYQQKSSTSPKLWIYDTSKLTSGVPGRFS
GSGSGNSYTLTISSMEAEDAATYYCFQGSGYPLTFGGGTKVEIKR

FIG. 3

| H01 | H02 | H03 | H04 | H05 | H06 | H07 | H08 | H09 | H10 | H11 | H12 | H13 | H14 | H15 |
|---|---|---|---|---|---|---|---|---|---|---|---|---|---|---|
| Q | V | Q | L | K | E | S | G | P | G | L | V | A | P | S |

| H16 | H17 | H18 | H19 | H20 | H21 | H22 | H23 | H24 | H25 | H26 | H27 | H28 | H29 | H30 |
|---|---|---|---|---|---|---|---|---|---|---|---|---|---|---|
| Q | S | L | S | I | T | C | T | V | S | G | F | S | L | K |

| H31 | H32 | H33 | H34 | H35 | H36 | H37 | H38 | H39 | H40 | H41 | H42 | H43 | H44 | H45 |
|---|---|---|---|---|---|---|---|---|---|---|---|---|---|---|
| N | Y | G | V | S | W | V | R | Q | P | P | G | K | G | L |

| H46 | H47 | H48 | H49 | H50 | H51 | H52 | H53 | H54 | H55 | H56 | H57 | H58 | H59 | H60 |
|---|---|---|---|---|---|---|---|---|---|---|---|---|---|---|
| E | W | L | G | V | I | W | G | D | G | S | T | N | Y | H |

| H61 | H62 | H63 | H64 | H65 | H66 | H67 | H68 | H69 | H70 | H71 | H72 | H73 | H74 | H75 |
|---|---|---|---|---|---|---|---|---|---|---|---|---|---|---|
| S | T | L | R | S | R | L | T | I | S | K | D | N | S | K |

| H76 | H77 | H78 | H79 | H80 | H81 | H82 | H82A | H82B | H82C | H83 | H84 | H85 | H86 | H87 | H88 | H89 | H90 |
|---|---|---|---|---|---|---|---|---|---|---|---|---|---|---|---|---|---|
| S | Q | L | F | L | K | L | N | R | L | Q | T | D | D | T | A | T | Y |

| H91 | H92 | H93 | H94 | H95 | H96 | H97 | H98 | H99 | H100 | H100A | H101 | H102 | H103 | H104 | H105 |
|---|---|---|---|---|---|---|---|---|---|---|---|---|---|---|---|
| Y | C | A | K | P | G | A | G | Y | A | M | D | Y | W | G | Q |

| H106 | H107 | H108 | H109 | H110 | H111 | H112 | H113 | H114 |
|---|---|---|---|---|---|---|---|---|
| G | T | S | V | T | V | S | S | - |

FIG. 4

| L01 | L02 | L03 | L04 | L05 | L06 | L07 | L08 | L09 | L10 | L11 | L12 | L13 | L14 | L15 |
|---|---|---|---|---|---|---|---|---|---|---|---|---|---|---|
| Q | I | V | L | T | Q | S | P | A | I | M | S | V | Y | P |

| L16 | L17 | L18 | L19 | L20 | L21 | L22 | L23 | L24 | L25 | L26 | L27 | L28 | L29 | L30 |
|---|---|---|---|---|---|---|---|---|---|---|---|---|---|---|
| G | E | K | V | T | M | T | C | S | A | S | S | - | S | V |

| L31 | L32 | L33 | L34 | L35 | L36 | L37 | L38 | L39 | L40 | L41 | L42 | L43 | L44 | L45 |
|---|---|---|---|---|---|---|---|---|---|---|---|---|---|---|
| S | Y | M | H | W | Y | Q | Q | K | S | S | T | S | P | K |

| L46 | L47 | L48 | L49 | L50 | L51 | L52 | L53 | L54 | L55 | L56 | L57 | L58 | L59 | L60 |
|---|---|---|---|---|---|---|---|---|---|---|---|---|---|---|
| L | W | I | Y | D | T | S | K | L | T | S | G | V | P | G |

| L61 | L62 | L63 | L64 | L65 | L66 | L67 | L68 | L69 | L70 | L71 | L72 | L73 | L74 | L75 |
|---|---|---|---|---|---|---|---|---|---|---|---|---|---|---|
| R | F | S | G | S | G | S | G | N | S | Y | S | L | T | I |

| L76 | L77 | L78 | L79 | L80 | L81 | L82 | L83 | L84 | L85 | L86 | L87 | L88 | L89 | L90 |
|---|---|---|---|---|---|---|---|---|---|---|---|---|---|---|
| S | S | M | E | A | E | D | V | A | T | Y | Y | C | F | Q |

| L91 | L92 | L93 | L94 | L95 | L96 | L97 | L98 | L99 | L100 | L101 | L102 | L103 | L104 | L105 |
|---|---|---|---|---|---|---|---|---|---|---|---|---|---|---|
| G | S | G | Y | P | L | T | F | G | G | G | T | K | L | E |

| L106 | L107 | L108 | L109 | L110 | L111 |
|---|---|---|---|---|---|
| I | K | R | - | - | - |

MDA-MB-231

MCF7

Demonstration of the binding of exemplary humanized Ab6s with conservative CDR modifications to MCF7 cell line.

SEQUENCE LISTING

```
<160> NUMBER OF SEQ ID NOS: 197

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
```

```
<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Tyr Gly Val Ser
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Trp Gly Asp Gly Ser Thr Asn Tyr His Ser Thr Leu Arg Ser
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Gly Ala Gly Tyr Ala Met Asp Tyr
1               5

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Thr Leu Arg
    50                  55                  60

Ser Arg Leu Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
            85                  90                  95

Lys Pro Gly Ala Gly Tyr Ala Met Asp Tyr Trp Gly Gln Gly Thr Ser
            100                 105                 110

Val Thr Val Ser Ser
            115
```

<210> SEQ ID NO 14
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
caggtgcagc tgaaggagtc aggacctggc ctggtggcgc cctcacagag cctgtccatc    60
acatgcactg tctcagggtt ctcattaaaa aactatggtg taagctgggt tcgccagcct   120
ccaggaaagg gtctggagtg gctgggagta atatggggtg acgggagcac aaattatcat   180
tcaactctca gatccagact gaccatcagc aaggataatt ccaagagcca acttttctta   240
aaactgaaca gactgcaaac tgatgacaca gccacgtact actgtgccaa acctggggcg   300
ggttatgcta tggactactg gggtcaagga acctcagtca ccgtctcctc a            351
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Ser Ala Ser Ser Ser Val Ser Tyr Met His
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Asp Thr Ser Lys Leu Thr Ser
1               5
```

<210> SEQ ID NO 17
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 17

Phe Gln Gly Ser Gly Tyr Pro Leu Thr
1               5

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ile Val Leu Thr Gln Ser Pro Ala Ile Met Ser Val Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Gly Gly Thr Lys Leu Glu Ile Lys Arg
            100                 105

<210> SEQ ID NO 19
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caaattgttc tcacccagtc tccagcaatc atgtctgtat atccagggga aaaggtcacc      60
atgacctgca gtgccagctc aagtgtaagt tacatgcact ggtaccagca gaagtcaagc     120
acctccccca aactctggat ttatgacaca tccaaactga cttctggagt cccaggtcgc     180
ttcagtggca gtgggtctgg aaactcttac tctctcacga tcagcagcat ggaggctgaa     240
gatgttgcca cttattactg ttttcagggg agtgggtacc cactcacgtt cggagggggg     300
accaagctgg aaataaaacg g                                               321

<210> SEQ ID NO 20
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caaattgttc tcacccagtc tccagcaatc atgtctgtat atccagggga aaaggtcacc      60
atgacctgca gtgccagctc aagtgtaagt tacatgcact ggtaccagca gaagtcaagc     120

```
acctccccca aactctggat ttatgacaca tccaaactga cttctggagt cccaggtcgc    180
ttcagtggca gtgggtctgg aaactcttac tctctcacga tcagcagcat ggaggctgaa    240
gatgttgcca cttattactg ttttcagggg agtgggtacc cactcacgtt cggagggggg    300
accaagctgg aaataaaacg ggctgatgct gcaccaactg tatcc                    345
```

```
<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ala Ser Ser Ser Val Ser Tyr Met His
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Thr Ser Lys Leu Thr Ser
1               5

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Ala Gly Tyr Ala Met Asp Tyr Trp Gly Gln Gly Thr Ser
            100                 105                 110

Val Thr Val Ser Ser
        115

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 24

Gln Ile Val Leu Thr Gln Ser Pro Ala Ile Met Ser Val Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Ser Leu Thr Ile Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Gly Gly Thr Lys Leu Glu Ile Lys Arg
            100                 105

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Gly Gly Thr Lys Leu Glu Ile Lys Arg
            100                 105

<210> SEQ ID NO 29
<400> SEQUENCE: 29

000

<210> SEQ ID NO 30
<400> SEQUENCE: 30

000

<210> SEQ ID NO 31
<400> SEQUENCE: 31

000

<210> SEQ ID NO 32
<400> SEQUENCE: 32

000

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Ala Gly Tyr Ala Met Asp Tyr Trp Gly Gln Gly Thr Leu
            100                 105                 110

Val Thr Val Ser Ser
        115

<210> SEQ ID NO 34
<400> SEQUENCE: 34

000

<210> SEQ ID NO 35
<400> SEQUENCE: 35

000

<210> SEQ ID NO 36

```
<400> SEQUENCE: 36

000

<210> SEQ ID NO 37
<400> SEQUENCE: 37

000

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
            100                 105

<210> SEQ ID NO 39
<400> SEQUENCE: 39

000

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Tyr Gly Val Ser
1               5

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Ile Trp Gly Asp Gly Ser Thr Asn Tyr His Ser Thr Leu Arg Ser
1               5                   10                  15
```

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Gly Arg Gly Tyr Ala Met Asp Tyr
1               5

<210> SEQ ID NO 43
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 44
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caggtgcagc tgcaggagtc cggaccagga ctggtggctc ccagccagac cctgtctatc     60
acctgcacag tgtctggctt ctccctgaag aactacggcg tgagctgggt gagacagcca    120
cctggcaagg gactggagtg gatcggcgtg atctggggcg acggctctac caattatcac    180
tccacactga ggagccgggt gaccatctcc aaggataact ccaagagcca gctgtttctg    240
aagctgaatc gcctgcagac agacgatacc gccacatact attgcgctaa gccaggccgg    300
ggctacgcta tggactattg gggccagggc accctggtga cagtgtccag c             351

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Ala Ser Ser Ser Val Ser Tyr Met His
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Thr Ser Lys Leu Thr Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Gln Gly Ser Gly Tyr Pro Leu Thr
1               5

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
                100                 105

<210> SEQ ID NO 49
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gagatcgtgc tgacccagtc tcctgccatc cagtccgtgt acccaggcga gaaggtgacc    60

```
atgacatgtt ccgcttcttc cagcgtgagc tacatgcatt ggtatcagca gaagtcttcc    120
acatctccca agctgtggat ctacgacacc tctaagctga catccggagt gcctggcagg    180
ttctctggat ccggaagcgg caacagctat accctgacaa tcagctctat ggaggctgag    240
gatgccgcta cctactattg tttccagggc tctggctatc ccctgacctt tggcggcggc    300
acaaaggtgg agatcaagcg t                                              321
```

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Tyr Gly Val Ser
1               5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Trp Gly Asp Gly Ser Thr Asn Tyr His Ser Thr Leu Arg Ser
1               5                   10                  15

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Arg Gly Tyr Ala Met Asp Tyr
1               5

<210> SEQ ID NO 53
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Ser Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala

```
                    85                  90                  95
Lys Pro Gly Arg Gly Tyr Ala Met Asp Tyr Trp Gly Gln Gly Thr Leu
                100                 105                 110

Val Thr Val Ser Ser
            115

<210> SEQ ID NO 54

<400> SEQUENCE: 54

000

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ala Ser Ser Ser Val Ser Tyr Met His
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Thr Ser Lys Leu Thr Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Gln Gly Ser Gly Tyr Pro Leu Thr
1               5

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Ser Thr Ser Pro Lys Leu Trp Ile Tyr
            35                  40                  45

Asp Thr Ser Lys Leu Thr Ser Gly Val Pro Gly Arg Phe Ser Gly Ser
        50                  55                  60
```

```
Gly Ser Gly Asn Ser Tyr Thr Leu Thr Ile Ser Ser Met Glu Ala Glu
            65                  70                  75                  80

Asp Ala Ala Thr Tyr Tyr Cys Phe Gln Gly Ser Tyr Pro Leu Thr
                85                  90                  95

Phe Gly Gly Gly Thr Lys Val Glu Ile Lys Arg
            100                 105
```

<210> SEQ ID NO 59

<400> SEQUENCE: 59

000

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Asn Tyr Gly Val Ser
1               5
```

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Val Ile Trp Gly Asp Gly Ser Thr Asn Tyr His Ser Ala Leu Arg Ser
1               5                   10                  15
```

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Pro Gly Arg Gly Tyr Ala Met Asp Tyr
1               5
```

<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
                20                  25                  30

Gly Val Ser Trp Val Arg Gln Pro Pro Gly Lys Gly Leu Glu Trp Ile
            35                  40                  45
```

```
Gly Val Ile Trp Gly Asp Gly Ser Thr Asn Tyr His Ser Ala Leu Arg
        50                  55                  60
Ser Arg Val Thr Ile Ser Lys Asp Asn Ser Lys Ser Gln Leu Phe Leu
 65                  70                  75                  80
Lys Leu Asn Arg Leu Gln Thr Asp Asp Thr Ala Thr Tyr Tyr Cys Ala
                85                  90                  95
Lys Pro Gly Arg Gly Tyr Ala Met Asp Tyr Trp Gly Gln Gly Thr Leu
                100                 105                 110
Val Thr Val Ser Ser
        115

<210> SEQ ID NO 64

<400> SEQUENCE: 64

000

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Ala Ser Ser Ser Val Ser Tyr Met His
 1               5                   10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Thr Ser Lys Leu Thr Ser
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Gln Gly Ser Gly Tyr Pro Leu Thr
 1               5

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Ile Val Leu Thr Gln Ser Pro Ala Ile Gln Ser Val Tyr Pro Gly
 1               5                   10                  15

Glu Lys Val Thr Met Thr Cys Ser Ala Ser Ser Ser Val Ser Tyr Met
```

```
                    20                  25                  30

His Trp Tyr Gln Gln Lys Ser Ser Thr Ser Pro Lys Leu Trp Ile Tyr
                35                  40                  45

Asp Thr Ser Lys Leu Thr Ser Gly Val Pro Gly Arg Phe Ser Gly Ser
            50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
            100                 105
```

<210> SEQ ID NO 69

<400> SEQUENCE: 69

000

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Asn Tyr Gly Val Ser
1               5
```

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Val Ile Trp Gly Asp Gly Ser Thr Asn Tyr His Ser Thr Leu Arg Ser
1               5                   10                  15
```

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Pro Gly Arg Gly Tyr Ala Met Asp Tyr
1               5
```

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Gln Val Gln Leu Gln Glu Ser Gly Pro Gly Leu Val Ala Pro Ser Gln
1               5                   10                  15
```

```
Thr Leu Ser Ile Thr Cys Thr Val Ser Gly Phe Ser Leu Lys Asn Tyr
             20                  25                  30

Gly Val Ser Trp Val Arg Gln Pro Pro Gly Lys Gly Leu Glu Trp Ile
         35                  40                  45

Gly Val Ile Trp Gly Asp Gly Ser Thr Asn Tyr His Ser Thr Leu Arg
     50                  55                  60

Ser Arg Val Thr Ile Ser Lys Asp Asn Ser Lys Ser Gln Leu Phe Leu
 65                  70                  75                  80

Lys Leu Asn Arg Leu Gln Thr Asp Asp Thr Ala Thr Tyr Tyr Cys Ala
                 85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 74

<400> SEQUENCE: 74

000

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Ala Ser Ser Ser Val Ser Tyr Met His
 1               5                  10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Thr Tyr Lys Leu Thr Ser
 1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe Gln Gly Ser Gly Tyr Pro Leu Thr
 1               5

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 78

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Tyr Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
            100                 105

<210> SEQ ID NO 79

<400> SEQUENCE: 79

000

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Tyr Gly Val Ser
1               5

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Ile Trp Gly Asp Gly Ser Thr Asn Tyr His Ser Thr Leu Arg Ser
1               5                   10                  15

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Pro Gly Arg Gly Tyr Ala Met Asp Tyr
1               5

<210> SEQ ID NO 83
<211> LENGTH: 117
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 83

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Ala Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 84

<400> SEQUENCE: 84

000

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 85

Ser Ala Ser Ser Ser Val Ser Tyr Met His
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 86

Asp Thr Ser Lys Leu Thr Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 87

Phe Gln Gly Ser Gly Tyr Pro Leu Thr
1               5

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

Glu Ile Val Leu Thr Gln Ser Pro Ala Ile Gln Ser Val Tyr Pro Gly
1               5                   10                  15
Glu Lys Val Thr Met Thr Cys Ser Ala Ser Ser Val Ser Tyr Met
            20                  25                  30
His Trp Tyr Gln Gln Lys Ser Ser Thr Ser Pro Lys Leu Trp Ile Tyr
        35                  40                  45
Asp Thr Ser Lys Leu Thr Ser Gly Val Pro Gly Arg Phe Ser Gly Ser
    50                  55                  60
Gly Ser Gly Asn Ser Tyr Thr Leu Thr Ile Ser Ser Met Glu Ala Glu
65                  70                  75                  80
Asp Ala Ala Thr Tyr Tyr Cys Phe Gln Gly Ser Gly Tyr Pro Leu Thr
                85                  90                  95
Phe Gly Gly Gly Thr Lys Val Glu Ile Lys Arg
            100                 105

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Tyr Gly Val Ser
1               5

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Ile Trp Ala Asp Gly Ser Thr Asn Tyr His Ser Thr Leu Arg Ser
1               5                   10                  15

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Gly Arg Gly Tyr Ala Met Asp Tyr
1               5

<210> SEQ ID NO 103
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Ala Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 104

<400> SEQUENCE: 104

000

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ala Ser Ser Ser Val Ser Tyr Met His
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Thr Ser Lys Leu Thr Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe Gln Gly Ser Gly Tyr Pro Leu Thr
1               5

<210> SEQ ID NO 108
<211> LENGTH: 107

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Ile Val Leu Thr Gln Ser Pro Ala Ile Gln Ser Val Tyr Pro Gly
1               5                   10                  15
Glu Lys Val Thr Met Thr Cys Ser Ala Ser Ser Val Ser Tyr Met
            20                  25                  30
His Trp Tyr Gln Gln Lys Ser Ser Thr Ser Pro Lys Leu Trp Ile Tyr
        35                  40                  45
Asp Thr Ser Lys Leu Thr Ser Gly Val Pro Gly Arg Phe Ser Gly Ser
    50                  55                  60
Gly Ser Gly Asn Ser Tyr Thr Leu Thr Ile Ser Ser Met Glu Ala Glu
65                  70                  75                  80
Asp Ala Ala Thr Tyr Tyr Cys Phe Gln Gly Ser Gly Tyr Pro Leu Thr
                85                  90                  95
Phe Gly Gly Gly Thr Lys Val Glu Ile Lys Arg
            100                 105

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

```
<210> SEQ ID NO 116
<400> SEQUENCE: 116

000

<210> SEQ ID NO 117
<400> SEQUENCE: 117

000

<210> SEQ ID NO 118
<400> SEQUENCE: 118

000

<210> SEQ ID NO 119
<400> SEQUENCE: 119

000

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asn Tyr Gly Val Thr
1               5

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Val Ile Trp Gly Asp Gly Ser Thr Asn Tyr His Ser Thr Leu Arg Ser
1               5                   10                  15

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Pro Gly Arg Gly Tyr Ala Met Asp Tyr
1               5

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123
```

```
Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Thr Trp Val Arg Gln Pro Pro Gly Lys Gly Leu Glu Trp Ile
            35                  40                  45

Gly Val Ile Trp Gly Asp Gly Ser Thr Asn Tyr His Ser Thr Leu Arg
        50                  55                  60

Ser Arg Val Thr Ile Ser Lys Asp Asn Ser Lys Ser Gln Leu Phe Leu
65              70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 124

<400> SEQUENCE: 124

000

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Ala Ser Ser Ser Val Ser Tyr Met His
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Thr Ser Lys Leu Thr Ser
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Phe Gln Gly Ser Gly Tyr Pro Leu Thr
1               5

<210> SEQ ID NO 128
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 128

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
            100                 105

<210> SEQ ID NO 129

<400> SEQUENCE: 129

000

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asn Tyr Gly Val Ser
1               5

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Val Ile Trp Gly Asp Gly Ser Thr Asn Tyr His Ser Thr Leu Arg Ser
1               5                   10                  15

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Gly Arg Gly Tyr Ala Met Asp Tyr
1               5

<210> SEQ ID NO 133
<211> LENGTH: 117
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Gln Glu Ser Gly Pro Gly Leu Val Ala Pro Ser Gln
1               5                   10                  15
Thr Leu Ser Ile Thr Cys Thr Val Ser Gly Phe Ser Leu Lys Asn Tyr
            20                  25                  30
Gly Val Ser Trp Val Arg Gln Pro Pro Gly Lys Gly Leu Glu Trp Ile
        35                  40                  45
Gly Val Ile Trp Gly Asp Gly Ser Thr Asn Tyr His Ser Thr Leu Arg
    50                  55                  60
Ser Arg Val Thr Ile Ser Lys Asp Asn Ser Lys Ser Gln Leu Phe Leu
65                  70                  75                  80
Lys Leu Asn Arg Leu Gln Thr Asp Asp Thr Ala Thr Tyr Tyr Cys Ala
                85                  90                  95
Lys Pro Gly Arg Gly Tyr Ala Met Asp Tyr Trp Gly Gln Gly Thr Leu
            100                 105                 110
Val Thr Val Ser Ser
        115

<210> SEQ ID NO 134

<400> SEQUENCE: 134

000

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Ala Ser Ser Ser Ile Ser Tyr Met His
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Thr Ser Lys Leu Thr Ser
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Phe Gln Gly Ser Gly Tyr Pro Leu Thr
```

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 138

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
            100                 105

<210> SEQ ID NO 139

<400> SEQUENCE: 139

000

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 140

Asn Tyr Gly Val Ser
1               5

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 141

Val Ile Trp Gly Asp Gly Ser Thr Asn Tyr His Ser Thr Leu Arg Ser
1               5                   10                  15

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 142

```
Pro Gly Arg Gly Tyr Ala Met Asp Tyr
1               5
```

<210> SEQ ID NO 143
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115
```

<210> SEQ ID NO 144

<400> SEQUENCE: 144

000

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Ser Ala Ser Ser Ser Ala Ser Tyr Met His
1               5                   10
```

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Asp Thr Ser Lys Leu Thr Ser
1               5
```

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Phe Gln Gly Ser Gly Tyr Pro Leu Thr
1               5

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Ala Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Val Glu Ile Lys Arg
                100                 105

<210> SEQ ID NO 149

<400> SEQUENCE: 149

000

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Tyr Gly Val Ser
1               5

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Ile Trp Gly Asp Gly Ser Thr Asn Tyr His Ser Thr Leu Arg Ser
1               5                   10                  15

<210> SEQ ID NO 152
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Gly Arg Gly Tyr Ala Met Asp Tyr
1               5

<210> SEQ ID NO 153
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 154

<400> SEQUENCE: 154

000

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Ala Ser Ser Ser Val Ser Tyr Met His
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Thr Ser Lys Leu Thr Ser
```

```
<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Gln Ala Ser Gly Tyr Pro Leu Thr
1               5

<210> SEQ ID NO 158
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Ser Thr Ser Pro Lys Leu Trp Ile Tyr
            35                  40                  45

Asp Thr Ser Lys Leu Thr Ser Gly Val Pro Gly Arg Phe Ser Gly Ser
        50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Ala Ser Gly Tyr Pro Leu Thr
                85                  90                  95

Phe Gly Gly Gly Thr Lys Val Glu Ile Lys Arg
            100                 105

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163
```

```
<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asn Tyr Gly Val Ser
1               5

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Ile Trp Gly Asp Gly Ser Thr Asn Tyr His Ser Thr Leu Arg Ser
1               5                   10                  15

<210> SEQ ID NO 172
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 172

Pro Gly Arg Gly Tyr Ala Met Asp Tyr
1               5

<210> SEQ ID NO 173
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Gln Leu Gln Glu Ser Gly Pro Gly Leu Val Ala Pro Ser Gln
1               5                   10                  15

Thr Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Ile
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 174

<400> SEQUENCE: 174

000

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ala Ser Ser Ser Val Ser Tyr Met His
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Thr Ser Lys Leu Thr Ser
1               5
```

```
<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Phe Gln Gly Ser Gly Phe Pro Leu Thr
1               5

<210> SEQ ID NO 178
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Phe Pro Leu Thr
                85                  90                  95

Phe Gly Gly Gly Thr Lys Val Glu Ile Lys Arg
            100                 105

<210> SEQ ID NO 179

<400> SEQUENCE: 179

000

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Phe Ser Leu Lys Asn Tyr Gly Val Ser
1               5                   10

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Phe Ser Leu Lys Asn Tyr Gly Val
```

```
<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Asn Tyr Gly Val Ser
1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Phe Ser Leu Lys Asn Tyr Gly
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Val Ile Trp Gly Asp Gly Ser Thr Asn
1               5

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Trp Gly Asp Gly Ser
1               5

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Trp Leu Gly Val Ile Trp Gly Asp Gly Ser Thr Asn
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 187

Ile Trp Gly Asp Gly Ser Thr
1               5

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Lys Pro Gly Ala Gly Tyr Ala Met Asp
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Lys Pro Gly Ala Gly Tyr Ala Met Asp Tyr
1               5                   10

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Val Ser Tyr Met His Trp Tyr
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Ser Val Ser Tyr
1               5

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Leu Trp Ile Tyr Asp Thr Ser Lys Leu Thr
1               5                   10

<210> SEQ ID NO 193

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Phe Gln Gly Ser Gly Tyr Pro Leu
1               5

<210> SEQ ID NO 194
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Thr Leu Arg
    50                  55                  60

Ser Arg Val Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Arg Gly Tyr Ala Met Asp Tyr Trp Gly Gln Gly Thr Leu
            100                 105                 110

Val Thr Val Ser Ser
        115

<210> SEQ ID NO 195
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Ile Val Leu Thr Gln Ser Pro Ala Ile Gln Ser Val Tyr Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Thr Leu Thr Ile Ser Ser Met Glu Ala Glu
65                  70                  75                  80

Asp Ala Ala Thr Tyr Tyr Cys Phe Gln Gly Ser Gly Tyr Pro Leu Thr
                85                  90                  95

Phe Gly Gly Gly Thr Lys Leu Glu Ile Lys Arg
            100                 105
```

<210> SEQ ID NO 196
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Lys Asn Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Thr Leu Arg
    50                  55                  60

Ser Arg Leu Thr Ile Ser Lys Asp Asn Ser Lys Ser Gln Leu Phe Leu
65                  70                  75                  80

Lys Leu Asn Arg Leu Gln Thr Asp Asp Thr Ala Thr Tyr Tyr Cys Ala
                85                  90                  95

Lys Pro Gly Ala Gly Tyr Ala Met Asp Tyr Trp Gly Gln Gly Thr Ser
            100                 105                 110

Val Thr Val Ser Ser
        115
```

<210> SEQ ID NO 197
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

```
Gln Ile Val Leu Thr Gln Ser Pro Ala Ile Met Ser Val Tyr Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Gly Gly Thr Lys Leu Glu Ile Lys Arg
            100                 105
```

ANTIBODIES, BINDING FRAGMENTS, AND METHODS OF USE

RELATED APPLICATIONS

This application claims the benefit of priority to U.S. provisional application Ser. No. 62/378,102, filed on Aug. 22, 2016, the contents of which are incorporated by reference in their entirety.

FIELD OF INVENTION

The present disclosure is directed to antibodies and binding fragments for immunotherapy in the treatment of proliferative disorders, including cancer and methods of diagnosis for the same. In particular, the disclosure relates to carbohydrate-related immunotherapy comprising an antibody and/or binding fragment against an immunogenic oligosaccharide SSEA4 and a pharmaceutical composition. Moreover, the disclosure relates to detection and/or diagnosis of hyperproliferative conditions and oncologically-related or specific carbohydrates expressed on abnormal cells.

BACKGROUND

Stage-specific embryonic antigen 4 (SSEA4) is a hexasaccharide belonged to globo-series glycosphingolipids (GSLs) and comprises the structure of Neu5Ac$\alpha$2→3 Gal$\beta$1→3 GalNAc$\beta$1→3 Gal$\alpha$1→4Gal$\beta$1→4Glc$\beta$1. Since SSEA4 was first isolated from human teratocarcinoma cells in 1983 (Kannagi R, et al., 1983), it is widely used as a surface marker to define human embryonic stem cells (hESCs) so far. In past decades, more and more studies indicated that GloboH, a GSL which shares the core structure Gal$\beta$1→3GalNAc$\beta$1→3Gal$\alpha$1→4Gal$\beta$1→4Glc$\beta$1 (SSEA3) with SSEA4, is overexpressed in many epithelial cancers, including ovarian, gastric, prostate, lung, breast, and pancreatic cancers (Zhang S, et al., 1997). And high-level expression of SSEA4 was observed in renal cell carcinoma (Saito S, et al., 1997) and glioblastoma multiforme (Lou Y W, et al., 2014). More interestingly, together with SSEA3 and GloboH, the expression of SSEA4 was found not only in breast tumor cells but also in breast cancer stem cells (Chang W W, et al., 2008; Huang Y L, et al., 2013).

Carbohydrate antigens, however, are often tolerated by the immune system and consequently induce weak or non-specific immune response (Stein K E, et al., 1992; Snapper C M, et al. 1996.). It is proposed that the carbohydrate antigens are unable to be internalized and digested by the antigen presenting cells (APC), such as macrophages, B cells or dendritic cells, and therefore cannot be presented to helper T (Th) cells. The lack of simulations from APC to T-cell results in the absent of antibody maturation and isotype switching. Accordingly, low affinity and non-class-switching IgM antibody against carbohydrate antigen is predominately produced (Musher D M, et al. 1990; Lortan J E, et al. 1993). Various approaches have been developed to address the deficiencies. Conjugating carbohydrate antigens with carrier proteins to improve the immunogenicity has been developed since 1950s (Lindberg A A, et al., 1999). Such kind of highly immunogenic proteins include diphtheria toxoid (DT), tetanus toxoid (TT), CRM197 (a non-toxic variant of diphtheria toxin), and a complex outer-membrane protein (OMP) mixture from *N. meningitides* (Ada G. et al., 1999). In addition to the intrinsic immunogenic property of these proteins, a booster effect is expected if the recipient had been immunized with these toxoids before. The carrier protein-carbohydrate antigen conjugates provide peptides conjugated with certain carbohydrate antigen to be processed and presented by APC through MHC II molecules. With the co-simulation from Th cells, T and B cells against certain carbohydrate antigen are then activated. Followed by antibody isotype-switching and maturation, the IgG antibody against certain carbohydrate antigen with high affinity and specificity could be further generated (Bazendale H E, et al., 2000). WO 2016029071 provides a carbohydrate based vaccine comprising synthetic SSEA4 analogs chemically conjugated to the immunogenic carrier diphtheria toxin cross-reacting material 197 (CRM 197) via a linker.

Although the carrier proteins in the carbohydrate vaccination provide a solution to improve the immunogenicity, the strategy poses some new and existing problems (Ingale S, et al., 2007). First, the foreign carrier protein and the attaching linker may elicit strong immune responses, thereby leading to the suppression of an antibody response against the carbohydrate antigen. Second, the chemical conjugation is basically on the lysine of the protein surface. The experiment process is difficult to control, resulting in the heterogeneous composition and final structure. The ambiguous composition probably causes different immune response. Third, the conjugation to mimic the expression of the carbohydrate on the cell surface is not ideal, thereby the induced antibody somehow is failed to recognize the carbohydrate cluster. Alternative approaches, such as carbohydrate PEGylation (Giorgi M E. et al., 2014), are investigated to overcome the remaining problems.

Nevertheless, the active immunization therapy mentioned above is not practice well in cancer patients who is in the status of hypoimmune. Particular those who receive chemotherapy or radiation therapy, as well as late-stage cancer patients, the efficacy of active immune intervention is often limited.

In view of the foregoing, instead of the vaccination, there exists a need to develop a therapeutic antibody against the cancer carbohydrate epitope to adapt passive immunity.

SUMMARY

The present disclosure provides exemplary isolated anti-SSEA4 monoclonal antibodies, binding fragments thereof, the nucleic acids encoding them, and the compositions containing such antibodies and fragment thereof, and their methods of use for inhibiting and/or reducing tumor growth and treatment of cancer. The exemplary monoclonal anti-SSEA4 antibodies and binding fragments provided herein can mediate antibody dependent cell-mediated cytotoxicity (ADCC) and/or complement-dependent cytotoxicity (CDC) activities to target and kill the tumor cells expressing SSEA4. In addition, the monoclonal anti-SSEA4 antibodies provided herein can be used to detect the SSEA4 expressing tumor cells within the tumor sample and/or sections in an exemplary diagnostic application.

Accordingly, provided herein are novel recombinant anti-SSEA4 antibodies specifically binding to SSEA4 or its derivatives and fragments, and methods of their use in anti-tumor immunotherapies, such as the treatment of cancer. Once bound to a cancer antigen, antibodies can induce antibody-dependent cell-mediated cytotoxicity, activate the complement system, and inhibit the growth of tumor.

In one embodiment, SSEA4 is highly expressed on various tumor cells, including brain tumor cells, lung tumor cells, breast tumor cells, oral tumor cells, esophageal tumor cells, stomach tumor cells, liver tumor cells, bile duct tumor cells, pancreatic tumor cells, colon tumor cells, renal tumor cells, cervical tumor cells, ovarian tumor cells, prostate tumor cells.

In one embodiment, the monoclonal anti-SSEA4 antibody specifically binds to SSEA4 molecule and derivatives.

In one embodiment, the compositions comprising the anti-SSEA4 antibody described herein are useful in anti-cancer therapies. In particular, the present embodiments provide the complementarity determining region (CDR) sequences of specific anti-SSEA4 antibody, which can be used in a variety of anti-SSEA4 binding portion. In particular, the present invention provides a humanized or chimeric antibody or an antigen-binding fragment thereof capable of binding to SSEA4 or its derivatives.

In certain embodiments, the CDR sequences are defined by Kabat method.

In certain embodiments, the anti-SSEA4 antibody has the activity of inhibiting tumor growth upon binding to SSEA4-positive or SSEA4 expressing cells.

In certain embodiments, the isolated anti-SSEA4 antibody is a monoclonal antibody. Monoclonal antibodies to SSEA4 can be made according to knowledge and skill in the art. For example, it can be made by injecting test subjects with human embryonic carcinoma cell and then isolating hybridomas expressing antibodies having the desired sequence or functional characteristics.

In one embodiment, the present disclosure provides an isolated monoclonal antibody or an antigen binding portion thereof that binds to SSEA4 wherein upon target binding the antibody has CDC inducing activity.

In one embodiment, the present disclosure provides an isolated monoclonal antibody or an antigen binding portion thereof that binds to SSEA4 wherein upon target binding the antibody has ADCC inducing activity.

In one aspect, the present disclosure provides an isolated monoclonal antibody or an antigen-binding fragment thereof comprising:

(i) H-CDR1 selected from SEQ ID Nos. 10, 40, 50, 60, 70, 80, 100, 120, 130, 140, 150 and 170, or 80% or more conserved sequence homologs thereof;

(ii) H-CDR2 selected from SEQ ID Nos. 11, 41, 51, 61, 71, 81, 101, 121, 131, 141, 151, and 171, or 80% or more conserved sequence homologs thereof;

(iii) H-CDR3 selected from SEQ ID Nos: 12, 42, 52, 62, 72, 82, 102, 122, 132, 142, 152 and 172, or 80% or more conserved sequence homologs thereof;

(iv) L-CDR1 selected from SEQ ID Nos. 15, 45, 55, 65, 75, 85, 105, 125, 135, 145, 155 and 175, or 80% or more conserved sequence homologs thereof;

(v) L-CDR2 selected from SEQ ID Nos. 16, 46, 56, 66, 76, 86, 106, 126, 136, 146, 156 and 176, or 80% or more conserved sequence homologs thereof, and (vi) L-CDR3 selected from SEQ ID Nos: 17, 47, 57, 67, 77, 87, 107, 127, 137, 147, 157, and 177 respectively, or 80% or more conserved sequence homologs thereof.

In one aspect, the present disclosure provides an isolated monoclonal antibody or an antigen-binding fragment thereof comprising:

(i) H-CDR1 selected from SEQ ID Nos. 10, 40, 50, 60, 70, 80, 100, 120, 130, 140, 150 and 170, or a conserved sequence homolog thereof containing less than 5 amino acid substitutions;

(ii) H-CDR2 selected from SEQ ID Nos. 11, 41, 51, 61, 71, 81, 101, 121, 131, 141, 151, and 171, or a conserved sequence homolog thereof containing less than 5 amino acid substitutions;

(iii) H-CDR3 selected from SEQ ID Nos: 12, 42, 52, 62, 72, 82, 102, 122, 132, 142, 152 and 172, or a conserved sequence homolog thereof containing less than 5 amino acid substitutions; and (iv) L-CDR1 selected from SEQ ID Nos. 15, 45, 55, 65, 75, 85, 105, 125, 135, 145, 155 and 175, or a conserved sequence homolog thereof containing less than 5 amino acid substitutions;

(v) L-CDR2 selected from SEQ ID Nos. 16, 46, 56, 66, 76, 86, 106, 126, 136, 146, 156 and 176, or a conserved sequence homolog thereof containing less than 5 amino acid substitutions; and (vi) L-CDR3 selected from SEQ ID Nos: 17, 47, 57, 67, 77, 87, 107, 127, 137, 147, 157, and 177 or a conserved sequence homolog thereof containing less than 5 amino acid substitutions.

In certain embodiments, the isolated monoclonal antibody or an antigen-binding fragment thereof further comprising amino acid substitution on the CDR selected from one or more of A100R, N31S, T62A on the heavy chain and/or S52Y on the light chain.

In certain embodiments, the isolated monoclonal antibody or an antigen-binding fragment thereof further comprising amino acid substitution on the CDR selected from one or more of V50A, G53A, S35T on the heavy chain and/or one or more of V30I/A, G91A, Y94F on the light chain.

In one aspect, the present disclosure provides an isolated monoclonal antibody or an antigen-binding fragment thereof, comprising: (i) a heavy chain variable domain selected from SEQ ID Nos. 13, 23, 33, 43, 53, 63, 73, 83, 103, 123, 133, 143, 153, and 173 or 80% or more conserved sequence homologs thereof; and (ii) a light chain variable domain selected from SEQ ID Nos. 18, 28, 38, 48, 58, 68, 78, 88, 108, 128, 138, 148, 158, and 178 or 80% or more conserved sequence homologs thereof.

In one embodiment, the isolated monoclonal antibody or an antigen-binding fragment thereof of claim 1, further comprising: (i) a heavy chain variable domain selected from SEQ ID Nos. 13, 23, 33, 43, 53, 63, 73, 83, 103, 123, 133, 143, 153, and 173 or 80% or more conserved sequence homologs thereof further comprising H-CDR1 selected from SEQ ID Nos. 10, 40, 50, 60, 70, 80, 100, 120, 130, 140, 150 and 170; H-CDR2 selected from SEQ ID Nos. 11, 41, 51, 61, 71, 81, 101, 121, 131, 141, 151, and 171, H-CDR3 selected from SEQ ID Nos: 12, 42, 52, 62, 72, 82, 102, 122, 132, 142, 152 and 172; respectively, and (ii) a light chain variable domain selected from SEQ ID Nos. 18, 28, 38, 48, 58, 68, 78, 88, 108, 128, 138, 148, 158, and 178 or 80% or more conserved sequence homologs thereof further comprising L-CDR1 selected from SEQ ID Nos. 15, 45, 55, 65, 75, 85, 105, 125, 135, 145, 155 and 175; and L-CDR2 selected from SEQ ID Nos. 16, 46, 56, 66, 76, 86, 106, 126, 136, 146, 156 and 176, and L-CDR3 selected from SEQ ID Nos: 17, 47, 57, 67, 77, 87, 107, 127, 137, 147, 157, and 177.

In one aspect, the present disclosure provides an isolated monoclonal antibody or an antigen-binding fragment thereof, comprising: (i) a heavy chain variable domain selected from SEQ ID Nos. 13, 23, 33, 43, 53, 63, 73, 83, 103, 123, 133, 143, 153, and 173 or a conserved sequence homologs thereof containing less than 10 amino acid substitutions; and (ii) a light chain variable domain selected from SEQ ID Nos. 18, 28, 38, 48, 58, 68, 78, 88, 108, 128, 138, 148, 158, and 178 or a conserved sequence homologs thereof containing less than 10 amino acid substitutions.

In one embodiment, the isolated monoclonal antibody or an antigen-binding fragment thereof, further comprising: (i) a heavy chain variable domain selected from SEQ ID Nos.

13, 23, 33, 43, 53, 63, 73, 83, 103, 123, 133, 143, 153, and 173 or a conserved sequence homologs thereof containing less than 10 amino acid substitutions further comprising H-CDR1 selected from SEQ ID Nos. 10, 40, 50, 60, 70, 80, 100, 120, 130, 140, 150 and 170; H-CDR2 selected from SEQ ID Nos. 11, 41, 51, 61, 71, 81, 101, 121, 131, 141, 151, and 171, H-CDR3 selected from SEQ ID Nos: 12, 42, 52, 62, 72, 82, 102, 122, 132, 142, 152 and 172; respectively, and (ii) a light chain variable domain selected from SEQ ID Nos. 18, 28, 38, 48, 58, 68, 78, 88, 108, 128, 138, 148, 158, and 178 or a conserved sequence homologs thereof containing less than 10 amino acid substitutions further comprising L-CDR1 selected from SEQ ID Nos. 15, 45, 55, 65, 75, 85, 105, 125, 135, 145, 155 and 175; and L-CDR2 selected from SEQ ID Nos. 16, 46, 56, 66, 76, 86, 106, 126, 136, 146, 156 and 176, and L-CDR3 selected from SEQ ID Nos: 17, 47, 57, 67, 77, 87, 107, 127, 137, 147, 157, and 177.

In one aspect, the present disclosure provides an isolated monoclonal antibody or an antigen-binding fragment thereof, further comprising: (i) a heavy chain variable domain selected from SEQ ID Nos. 13, 23, 33, 43, 53, 63, 73, 83, 103, 123, 133, 143, 153, and 173, or a conserved sequence homologs thereof containing less than 10 amino acid substitutions; and (ii) a light chain variable domain selected from SEQ ID Nos. 18, 28, 38, 48, 58, 68, 78, 88, 108, 128, 138, 148, 158, and 178, or sequence homologs thereof containing less than 10 conserved amino acid substitutions, further comprising L-CDR1 selected from SEQ ID Nos. 15, 45, 55, 65, 75, 85, 105, 125, 135, 145, 155 and 175; and L-CDR2 selected from SEQ ID Nos. 16, 46, 56, 66, 76, 86, 106, 126, 136, 146, 156 and 176, and L-CDR3 selected from SEQ ID Nos: 17, 47, 57, 67, 77, 87, 107, 127, 137, 147, 157, and 177.

In one aspect, the present disclosure provides an isolated monoclonal antibody or an antigen-binding fragment thereof, further comprising: (i) a heavy chain variable domain selected from SEQ ID Nos. 13, 23, 33, 43, 53, 63, 73, 83, 103, 123, 133, 143, 153, and 173, or a conserved sequence homologs thereof containing less than 10 amino acid substitutions, further comprising H-CDR1 selected from SEQ ID Nos. 10, 40, 50, 60, 70, 80, 100, 120, 130, 140, 150 and 170; H-CDR2 selected from SEQ ID Nos. 11, 41, 51, 61, 71, 81, 101, 121, 131, 141, 151, and 171, H-CDR3 selected from SEQ ID Nos: 12, 42, 52, 62, 72, 82, 102, 122, 132, 142, 152 and 172; respectively; and (ii) a light chain variable domain selected from SEQ ID Nos. 18, 28, 38, 48, 58, 68, 78, 88, 108, 128, 138, 148, 158, and 178; or a conserved sequence homologs thereof containing less than 10 amino acid substitutions.

In one aspect, the present disclosure provides an isolated monoclonal antibody or an antigen-binding fragment thereof, comprising the respective corresponding VH, VL and respective H-CDRs and L-CDRS as set forth in each variant in Tables 2A-2D.

In certain embodiments, the isolated antibody or antigen-binding fragment is:
 a. a chimeric antibody or a fragment thereof; or
 b. a humanized antibody or fragment thereof; or
 c. a human antibody or fragment thereof; or
 d. an antigen-binding fragment selected from the group consisting of Fab, Fab', Fv, scFv, dsFv, F(ab)$_2$, Fd and a diabody.

In certain embodiments, the isolated antibody or antigen-binding fragment is IgG.

In certain embodiments, the isolated antibody or antigen-binding fragment thereof targets the carbohydrate antigen SSEA4 having the structure Neu5Acα2→3Galβ1→3GalNAc β1→3Galα1→4Galβ1-4Glcβ1.

In certain embodiments, the isolated antibody or antigen-binding fragment of wherein the antibody has CDC and/or ADCC inducing activity upon binding to the target cells.

In certain embodiments, the pharmaceutical composition, comprising the isolated antibody or antigen-binding fragment thereof and a pharmaceutical acceptable carrier.

In certain embodiments, the pharmaceutical composition further comprising one or more anti-tumor agent.

In certain embodiments, the pharmaceutical composition wherein the anti-tumor agent is a chemotherapeutic agent.

In certain embodiments, the immunoconjugate comprising the antibody and a cytotoxic agent.

In certain embodiments, the immunoconjugate having the formula AB-(L-D)p, wherein: (a) AB is the antibody of anyone of claims 1-10; (b) L is a linker; (c) D is a suitable cytotoxic drug, and (d) p ranges from 1 to 8.

In certain embodiments, the immunoconjugate wherein the drug is MMAE.

In certain embodiments, the immunoconjugate wherein the linker is cleavable linker.

In certain embodiments, the ADC wherein the linker is an alkoxyamine-cleavable linker.

In certain embodiments, the pharmaceutical formulation comprising the immunoconjugate of claims and a pharmaceutically acceptable carrier.

In certain embodiments, the pharmaceutical formulation further comprising an additional therapeutic agent.

In certain embodiments, the isolated nucleic acid (cDNA) encoding the antibody of or a binding fragment disclosed herein.

In certain embodiments, the host cell comprising the nucleic acid encoding the antibody of or a binding fragment disclosed herein.

In certain embodiments, the disclosure provides a method of producing an antibody comprising culturing the host cell so that the antibody is produced.

In certain embodiments, the disclosure provides an antibody produced by steps comprising:
 (a) providing a nucleic acid encoding 3 VL domain CDRs having sequences of: L-CDR1 selected from SEQ ID Nos. 15, 45, 55, 65, 75, 85, 105, 125, 135, 145, 155 and 175; and L-CDR2 selected from SEQ ID Nos. 16, 46, 56, 66, 76, 86, 106, 126, 136, 146, 156 and 176, and L-CDR3 selected from SEQ ID Nos: 17, 47, 57, 67, 77, 87, 107, 127, 137, 147, 157, and 177, respectively;
 (b) combining a repertoire of nucleic acids encoding 3 VH domain CDRs having the sequences of H-CDR1 selected from SEQ ID Nos. 10, 40, 50, 60, 70, 80, 100, 120, 130, 140, 150 and 170; H-CDR2 selected from SEQ ID Nos. 11, 41, 51, 61, 71, 81, 101, 121, 131, 141, 151, and 171, H-CDR3 selected from SEQ ID Nos: 12, 42, 52, 62, 72, 82, 102, 122, 132, 142, 152 and 172; respectively with the nucleic acid encoding the 3 VL domain CDRs, so as to provide a product repertoire of nucleic acids encoding the 3 VL domain CDRs and the repertoire of 3 VH domain CDRs;
 (c) expressing the nucleic acids of the product repertoire;
 (d) selecting an antigen-binding fragment comprising a variable domain that specifically binds to SSEA4 and that is expressed from the nucleic acids of the product repertoire; and
 (e) producing an antibody comprising the antigen-binding fragment.

In certain embodiments, the disclosure provides a method of treating a subject having a SSEA4-positive cancer, the method comprising administering to the subject in need thereof an effective amount of the pharmaceutical composition disclosed herein.

In certain embodiments, the disclosure provides a method wherein the SSEA4-positive cancer is selected from brain, lung, breast, oral, esophageal, stomach, liver, bile duct, pancreatic, colon, kidney, cervical, ovarian, and prostate cancer.

In certain embodiments, the disclosure provides method further comprising administering an additional therapeutic modality or agent in combination to the individual.

In certain embodiments, the disclosure provides a method wherein the combined treatment modality is selected from therapeutic antibodies, cell therapies, radiation, cytokines, and/or chemotherapeutic agents.

In certain embodiments, the disclosure provides a method of inhibiting proliferation of a SSEA4-positive cell, the method comprising exposing the cell to the pharmaceutical formulations as disclosed herein under conditions permissive for binding of the antibodies/fragments/ADCs to SSEA4 on the surface of the cell expressing carbohydrate antigen, thereby inhibiting proliferation of the cell.

In certain embodiments, the method of treating a subject having a SSEA4-positive cancer, wherein the SSEA4-positive cancer is resistant to a first therapeutic agent, the method comprising administering to the individual an effective amount of the pharmaceutical formulation disclosed herein.

In certain embodiments, the method wherein the SSEA4-positive cancer is brain, lung, breast, oral, esophageal, stomach, liver, bile duct, pancreatic, colon, kidney, cervical, ovarian, and/or prostate cancer.

In certain embodiments, the method wherein the first therapeutic agent comprises a first antibody/binding fragment/ADC that binds an antigen other than SSEA4, and/or radiation, and/or chermotherapeutic agents.

In certain embodiments, the method of detecting SSEA4 in a biological sample comprising contacting the biological sample with the anti-SSEA4 antibody as disclosed herein under conditions permissive for binding of the anti-SSEA4 antibody to a naturally occurring SSEA4, and detecting whether a complex is formed between the anti-SSEA4 antibody and a naturally occurring SSEA4 in the biological sample.

In certain embodiments, the method wherein the biological sample is a cancer sample.

In certain aspect, the disclosure provides a method for detecting a SSEA4-positive cancer comprising (i) administering a labeled anti-SSEA4 antibody to a subject having or suspected of having a carbohydrate antigen expressing tumor, wherein the labeled anti-SSEA4 antibody comprises the anti-SSEA4 antibody as disclosed herein, and (ii) detecting the labeled anti-SSEA4 antibody in the subject, wherein detection of the labeled anti-SSEA4 antibody indicates a SSEA4-positive cancer in the subject.

In certain embodiments, the isolated antibody wherein the antibody specifically binds to SSEA4 with an affinity constant less than $10^{-7}$ M.

In certain embodiments, the isolated antibody wherein the antibody is IgG1, IgG2, IgG3, or IgG4.

In certain embodiments, the isolated antibody wherein the antibody is IgG1λ or IgG1κ.

In certain embodiments, the monoclonal antibody or antigen-binding portion thereof wherein the monoclonal antibody or antigen-binding portion thereof binds to SSEA4 with a $K_D$ of $1\times10^{-7}$M or less, and wherein the $K_D$ is measured by surface plasmon resonance (Biacore) analysis.

In certain embodiments, the isolated anti-SSEA4 antibody or binding fragment thereof wherein the binding affinity is <50 nM.

The present disclosure is directed to antibodies and binding fragments thereof which specifically binds to SSEA4 according to any of the aspect/embodiments of the present invention. In one aspect, the present disclosure provides an isolated monoclonal antibody or a binding fragment thereof that binds to SSEA4 wherein upon target binding the antibody has ADCC inducing activity.

According to certain embodiments, the antibody is a monoclonal antibody.

According to certain embodiments, the antibody is a chimeric or humanized antibody.

According to certain embodiments, the antibody is bispecific antibody.

According to certain embodiment, the invention disclosed a chimeric antigen receptor (CAR) which selectively binds to SSEA4. In this embodiment, the CAR may comprise an antigen-binding domain which has a variable heavy chain ($V_H$) and a variable light chain ($V_L$).

In one aspect the antibody or binding fragment thereof have the half-maximum binding to SSEA4 with an $EC_{50}$ of about 5, 10, 15, 20, 15, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250 nanogram/mL or a value between any of the two values recited herein by ELISA binding assay.

In one aspect, the isolated anti-SSEA4 antibody or binding fragment thereof wherein the binding affinity is <50 nM (less than 50 nM). In certain embodiments, the binding affinity can range from <5, <10, <15, <20, <25, <30, <35, <40, <45, or <50 nM.

According to one embodiment of the present disclosure, the pharmaceutical composition comprises (1) a therapeutically effective amount of the antibody or antigen-binding fragment according to any of aspects/embodiments of the present disclosure, and optionally (2) a pharmaceutically acceptable carrier.

In one aspect, the present invention is directed to a pharmaceutical composition for treating cancer in a subject in need thereof comprising the isolated antibody, or antigen-binding fragment thereof comprising the exemplary H-CDR1, H-CDR2, H-CDR3, L-CDR1, L-CDR2, and L-CDR3 as disclosed herein and a pharmaceutical acceptable carrier.

In certain embodiments, the pharmaceutical composition is useful in the treatment against a hyperproliferative disease, such as cancer. Exemplary hyperproliferative disease can include, for example, one or more of the tumors listed in Table 4.

TABLE 4

Expression of globo-series glycosphingolipids in tumor cells lines.

| Tumor origin | SSEA-4+ | SSEA-3+ | Globo H+ |
| --- | --- | --- | --- |
| Brain | 12/17 | 9/17 | 6/17 |
| Lung | 13/20 | 5/20 | 13/20 |
| Breast | 17/23 | 6/23 | 14/23 |
| Mouth | 8/13 | 2/13 | 11/13 |
| Esophagus | 1/2 | 0/2 | 2/2 |
| Stomach | 4/6 | 3/6 | 6/6 |
| Liver | 6/10 | 4/10 | 9/10 |
| Bile duct | 2/5 | 1/5 | 3/5 |
| Pancreas | 8/8 | 3/8 | 6/8 |
| Colon | 5/7 | 0/7 | 6/7 |

TABLE 4-continued

Expression of globo-series glycosphingolipids in tumor cells lines.

| Tumor origin | SSEA-4+ | SSEA-3+ | Globo H+ |
|---|---|---|---|
| Kidney | 5/6 | 0/6 | 5/6 |
| Cervix | 3/4 | 2/4 | 1/4 |
| Ovary | 8/9 | 2/9 | 5/9 |
| Prostate | 4/4 | 1/4 | 1/4 |

Expression of globo-series GSLs was determined by flow cytometry. Cell lines in which more than 15% of total cells were positive in flow cytometry are labeled positive.

Table 4. The list of globo-series glycosphingolipids expression on tumor cells lines. Various tumor cells expressing high globo-series glycosphingolipids, such as brain tumor cells, lung tumor cells, breast tumor cells, oral tumor cells, esophageal tumor cells, stomach tumor cells, liver tumor cells, bile duct tumor cells, pancreatic tumor cells, colon tumor cells, renal tumor cells, cervical tumor cells, ovarian tumor cells, prostate tumor cells.

In certain aspects, the disclosure provides a method of treating cancer in a subject in need thereof, wherein the method comprises administering to the subject a therapeutically effective amount of the representative pharmaceutical composition whereby the administered antibody enhances ADCC or CDC activity in said subject.

In certain embodiments, the method provided treats cancer selected from the group consisting of brain cancer, lung cancer, breast cancer, oral cancer, esophageal cancer, stomach cancer, liver cancer, bile duct cancer, pancreatic cancer, colon cancer, kidney cancer, bone cancer, skin cancer, cervical cancer, ovarian cancer, and prostate cancer.

According to embodiments of the present disclosure, the method includes administering to the subject an effective amount of the pharmaceutical composition comprising the antibody and/or pharmaceutical composition according to any of the aspects/embodiments of the present disclosure.

In certain embodiments, the present disclosure provides methods for diagnosing cancers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

As used herein, symbolic, graphic, and text nomenclature for describing glycans and related structures are well-established and understood in the art, including, for example, "Symbols Nomenclatures for Glycan Representation", Proteomics. 2009 December; 9(24): 5398-5399 by Ajit Varki et al.

FIG. 1A-1E. 1A: CDR sequences of representative Ab6 antibodies and/or binding fragments. The CDR sequences (SEQ ID NOS 10, 180-183, 11, 184-187, 12, 12, 12, 188-189, 15, 15, 15 , 190-191, 16, 16, 16, 192, 17, 17, 17, 193, and 17, respectively, in order of appearance) are defined by Kabat, AbM, Chothia, Contact, and IMGT methods, respectively. FIG. 1B: Demonstration of anti-SSEA4 antibodies with CDRs modifications. (SEQ ID NOS 13, 194, 18, and 195, respectively, in order of appearance). FIG. 1C: Demonstration of anti-SSEA4 antibodies with variable domain modifications (SEQ ID NOS 13, 23, 33, 18, 28, and 38, respectively, in order of appearance). FIG. 1D. Demonstration of anti-SSEA4 antibodies with non-conservative CDR modification: Sequence alignment of hAb6-3, hAb6-3.1/2/3/4 (SEQ ID NOS 33, 43, 53, 63, 43, 38, 38, 38, 38, and 78, respectively, in order of appearance). FIG. 1E. Demonstration of anti-SSEA4 antibodies with conservative CDR modification: Sequence alignment of hAb6-3 and hAb6-3.101/103/105/106/107/108/110 (SEQ ID NOS 33, 83, 103, 123, 43, 43, 43, 43, 38, 38, 38, 38, 138, 148, 158, and 178, respectively, in order of appearance).

FIG. 2. Representative humanized Ab6 sequences with 6 or 10 amino acid substitutes in variable domain. The CDR regions are underlined and the substituted amino acids are in box (SEQ ID NOS 13, 18, 23, 28, 33, and 38, respectively, in order of appearance).

FIG. 3. Kabat number of chAb6 heavy chain variable domain (SEQ ID NO: 196).

FIG. 4. Kabat number of chAb6 light chain variable domain (SEQ ID NO: 197).

FIG. 6C represents a demonstration of the binding affinity of non-conservatively modified amino acid substitutions. FIG. 6D represents a demonstration of the binding affinity of conservatively modified amino acid substitutions.

(FIG. 10A) The exemplary chimeric Ab6 (chAb6, 20 µg/mL) binds to HPAC, an exemplary pancreatic tumor cells line with high expression level of SSEA4, in (as shown in FIG. 10B) a dose-dependent manner. The binding $EC_{50}$ to HPAC cells is about 4 µg/mL.

FIG. 11C is a demonstration of the binding of exemplary humanized Ab6s with non-conservative CDR modifications to MDA-MB-231 cell line. FIG. 11D is a demonstration of the binding of exemplary humanized Ab6s with non-conservative CDR modifications to MCF7 cell line.

FIG. 11E is a demonstration of the binding of exemplary humanized Ab6s with conservative CDR modifications to MDA-MB-231 cell line. FIG. 11F is a demonstration of the binding of exemplary humanized Ab6s with conservative CDR modifications to MCF7 cell line FIG. 12. Demonstration of the ADCC activity of an exemplary chAb6 on a pancreatic tumor cells line HPAC. Representative chAb6 induces ADCC to kill HPAC cells in a dose-dependent manner. The $EC_{50}$ is 5 ng/mL. Human IgG1, kappa (hIgG1, kappa) is used as control.

The result of immune-histochemistry staining showed that chAb6 can be applied to detect SSEA4 expression in tumor samples.

Figure 20:
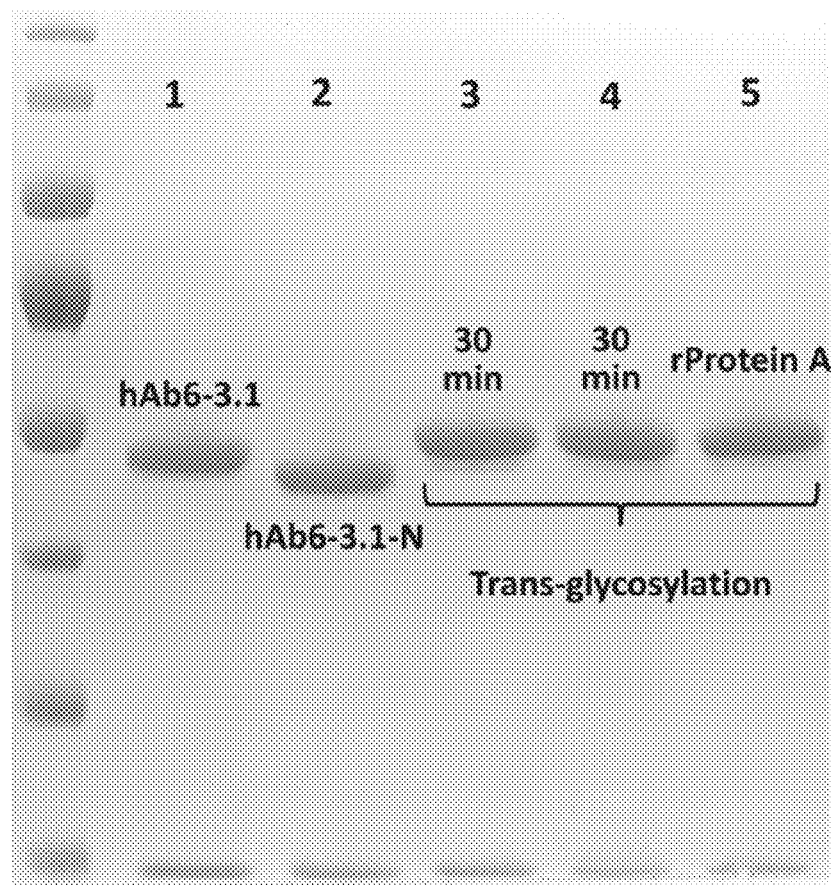

FIG. 20. Characterization of glycoengineered hAb6-3.1 by SDS-PAGE. Lane 1, native antibody produced from mammalian cells; Lane 2, Antibody with mono-GlcNAc; Lane 3-4, Glyo-engineered hAb6-3.1 produced in 30 mins and 60 mins; Lane 5, Purified glyco-engineered antibody.

Figure 21:
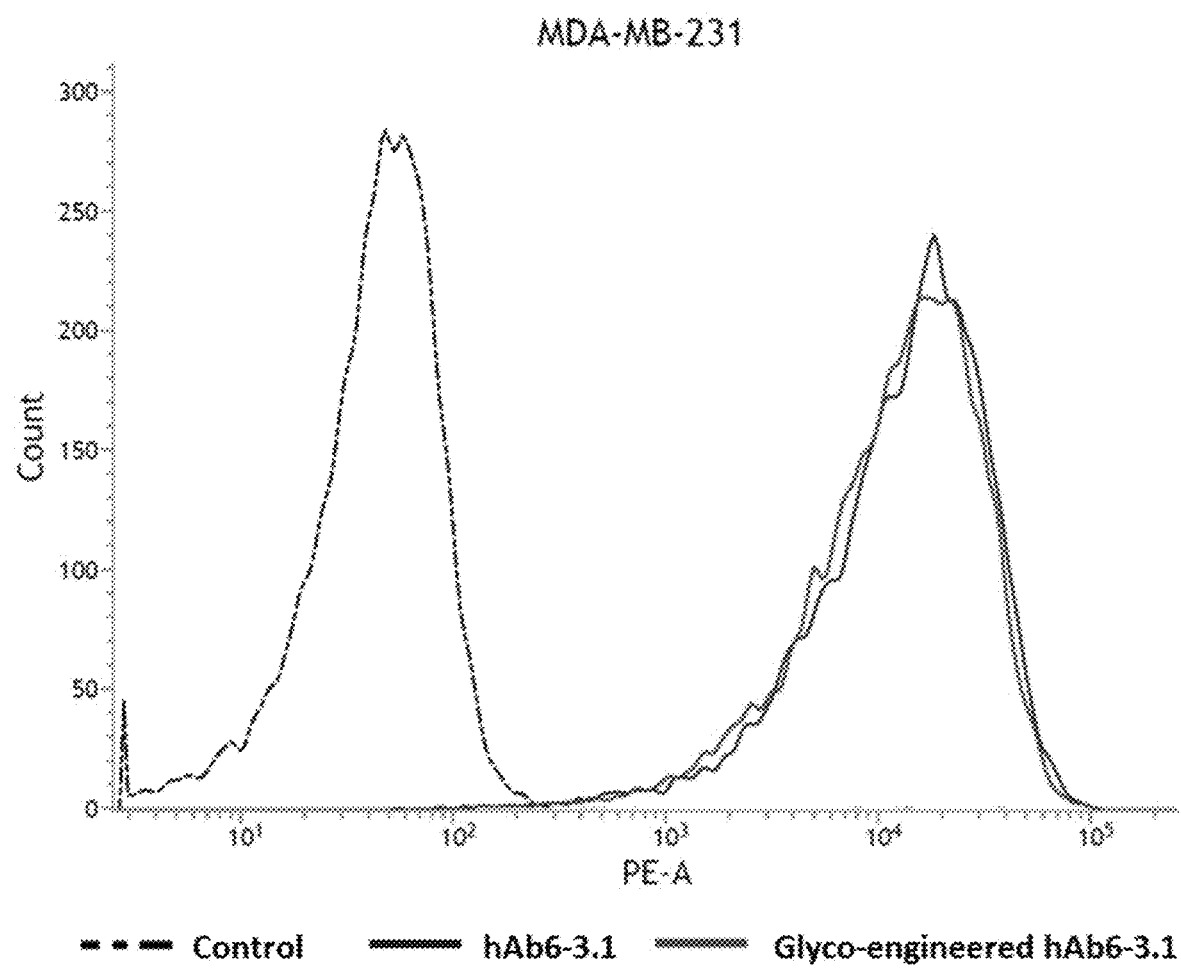

FIG. 21. The binding property of glycoengineered hAb6-3.1 by cell flow cytometry. The glyco-engineered antibody (red line) exhibits similar binding property with the native antibody (blue line) to SSEA4-expressing cell line MDA-MB-231. The result indicated that glycoengineering does not affect the antigen binding property of hAb6-3.1

Figure 22:
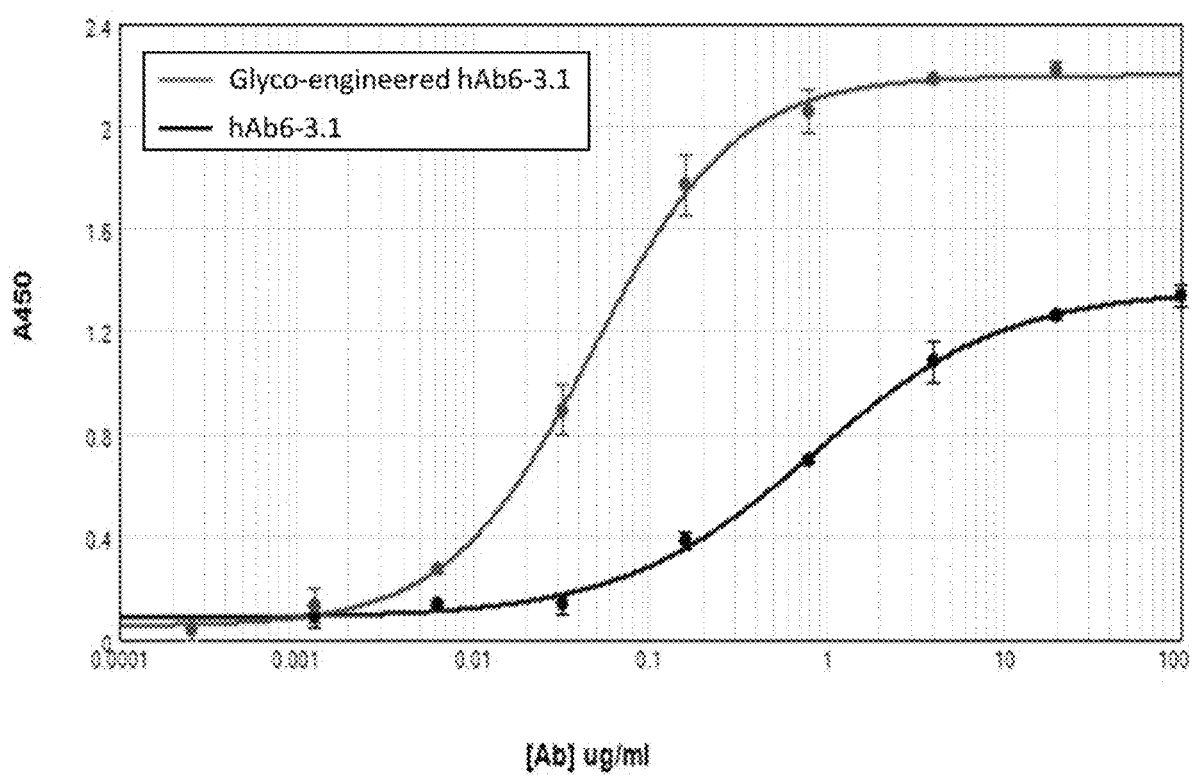

FIG. 22. Fc gamma receptor IIIA binding. The binding (EC50) of hAb6-3.1 to Fc gamma receptor IIIA was dramatically enhanced by glycoengineering. The EC50 for native and glyco-engineered antibody are 0.84 and 0.047 μg (microgram)/mL, respectively.

Figure 23:
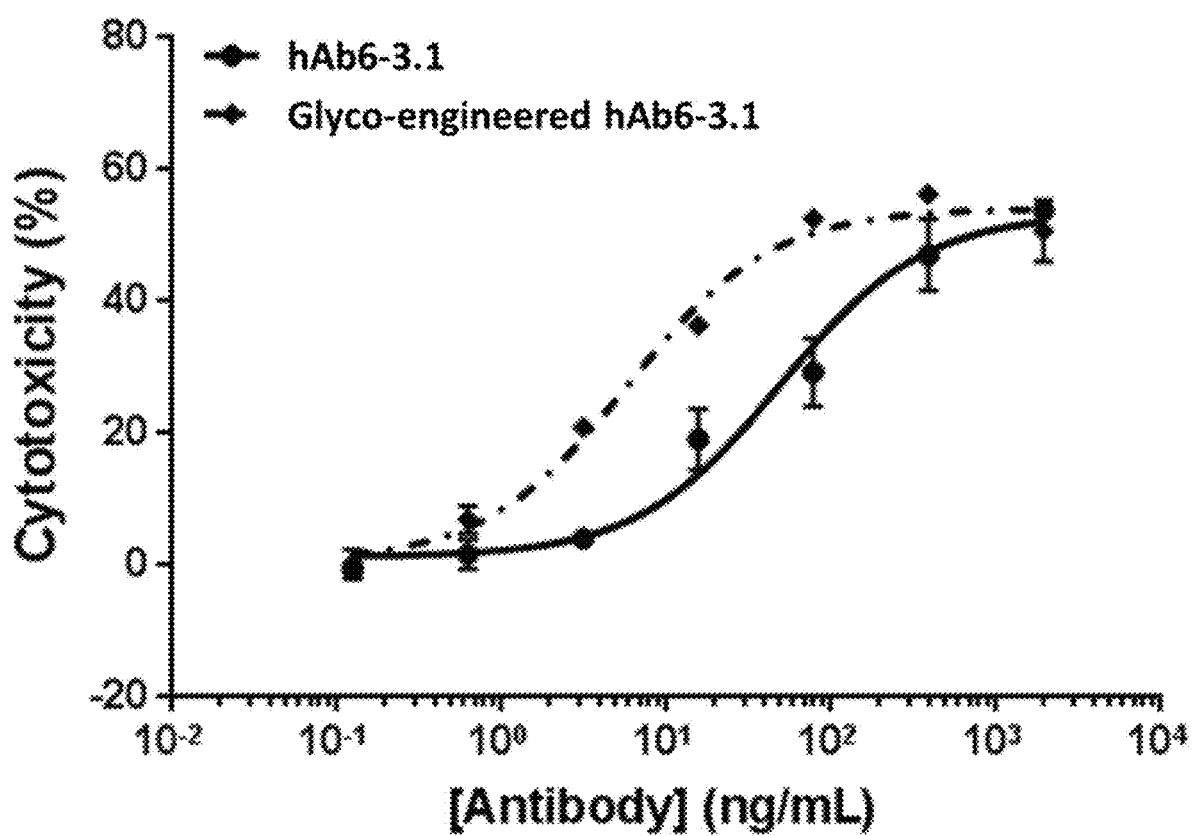

FIG. 23. The ADCC activity of native and glyco-engineered hAb6-3.1 on MDA-MB-231 cells. Both native and glyco-engineered hAb6-3.1 mediated ADCC to kill MDA-MB-231 cells in a dose-dependent manner. The ADCC activity of hAb6-3.1 was significantly improved by glyco-engineering. The EC50 for native and glyco-engineered hAb6-3.1 are about 50.29 and about 6.02 ng/ml, respectively.

Figure 24A:
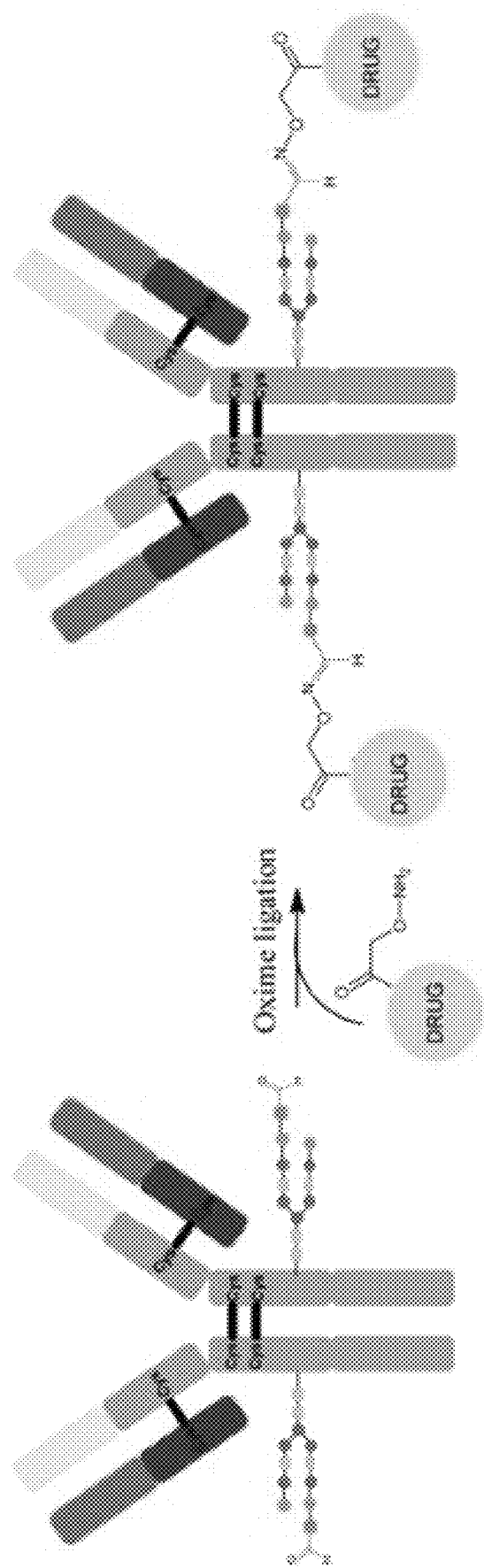
Figure 24B:
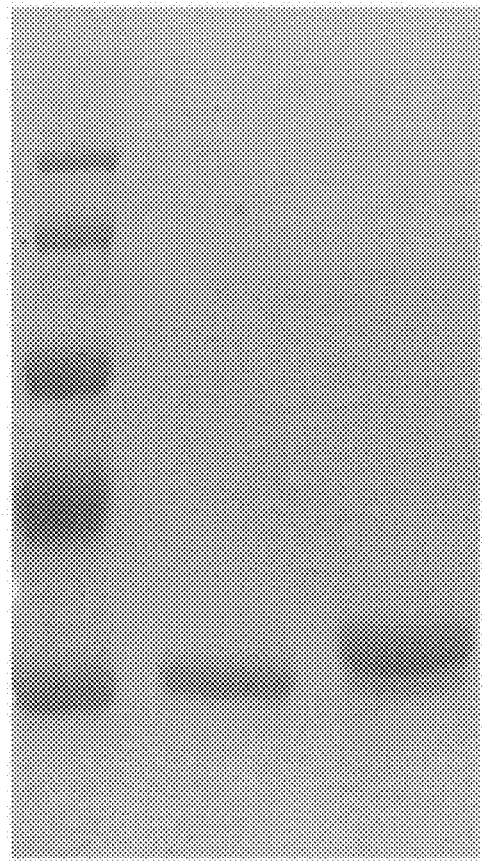

FIG. 24A. The oxmine ligation of drug onto the Fc glycan for ADC formation. FIG. 24B. is the SDS-PAGE profile of ADC complex formation. Lane 1: Marker, Lane 2: ketone tagged of hAb6-3.1, Lane 3: hAb6-3.1-A01.

Figure 25A:
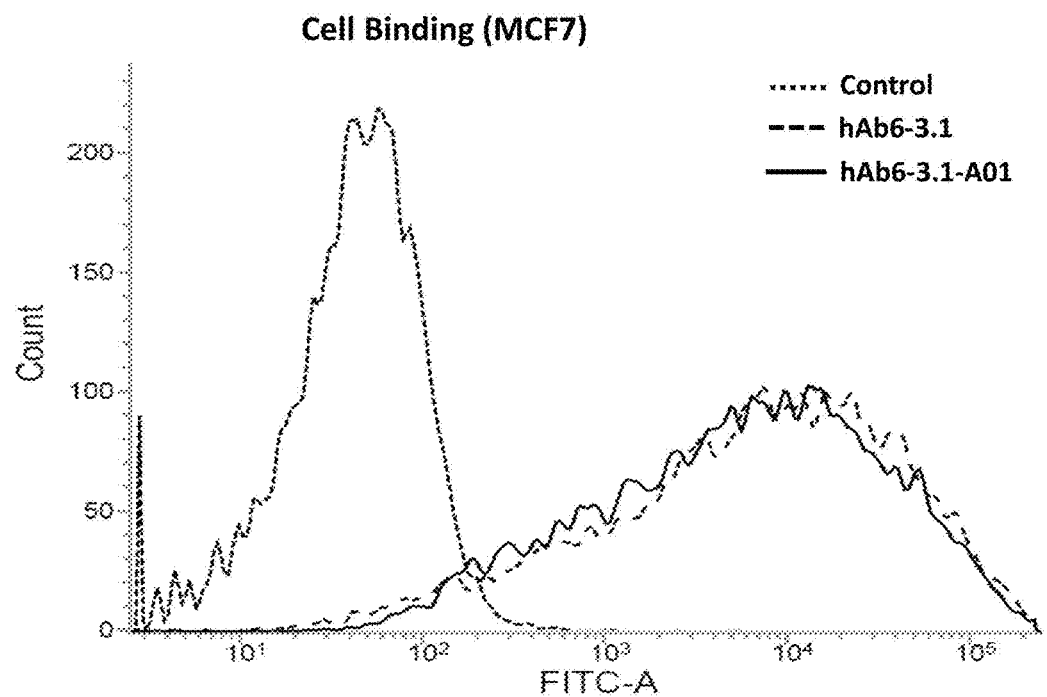
Figure 25B:
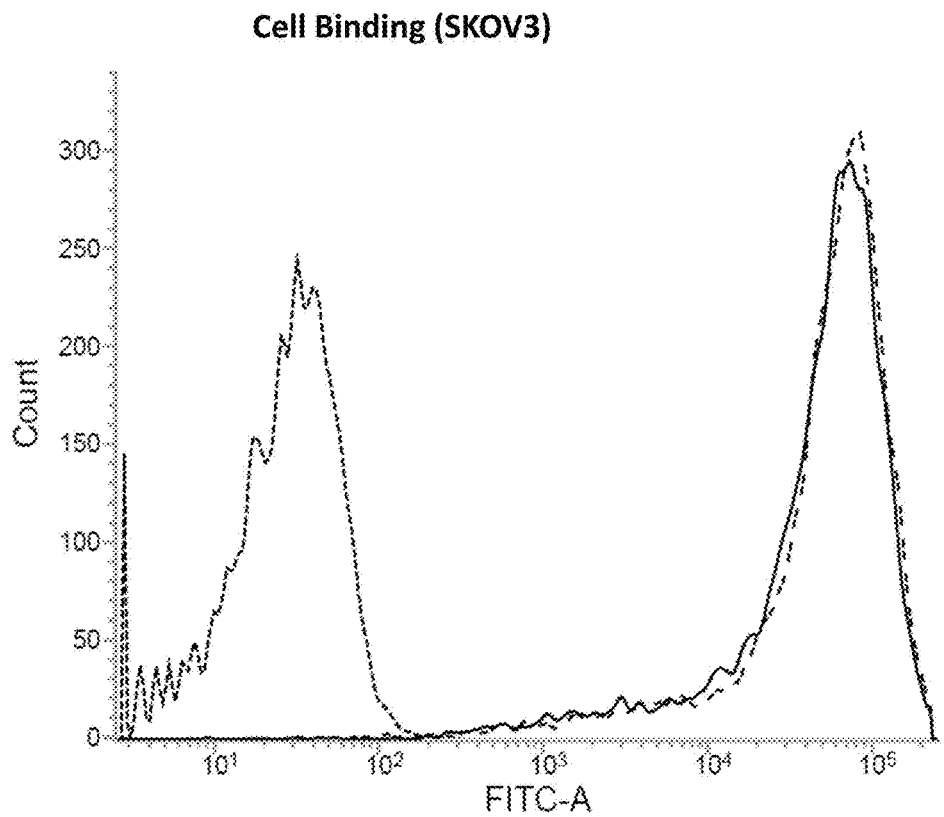

FIGS. 25A and 25B. FIG. 25A is The binding ability of hAb6-3.1-A01 to SSEA4-expressing cells by flow cytometry. SSEA4-expressing cell line MCF7 and SKOV3 were washed with PBS and 1×105 of cells were incubated with 10 ug/mL of hAb6-3.1 or hAb6-3.1-A01 in FACS buffer (PBS containing 2% FBS and 0.1% NaN3) on ice for 1 hr. After washing with PBS, the cells were stained with Alexa-Fluor 488 labeled anti-human IgG antibody and incubated on ice for 0.5 hr. The signals for cell binding of antibodies were detected by flow cytometry (Figure XX11AB). The result indicated the binding property of hAb6-3.1-A01 to SSEA4-expressing cell is similar with parental antibody hAb6-3.1. FIG. 25B is the comparison of cell binding property of hAb6-3.1 and hAb6-3.1-A01.

Figure 26:
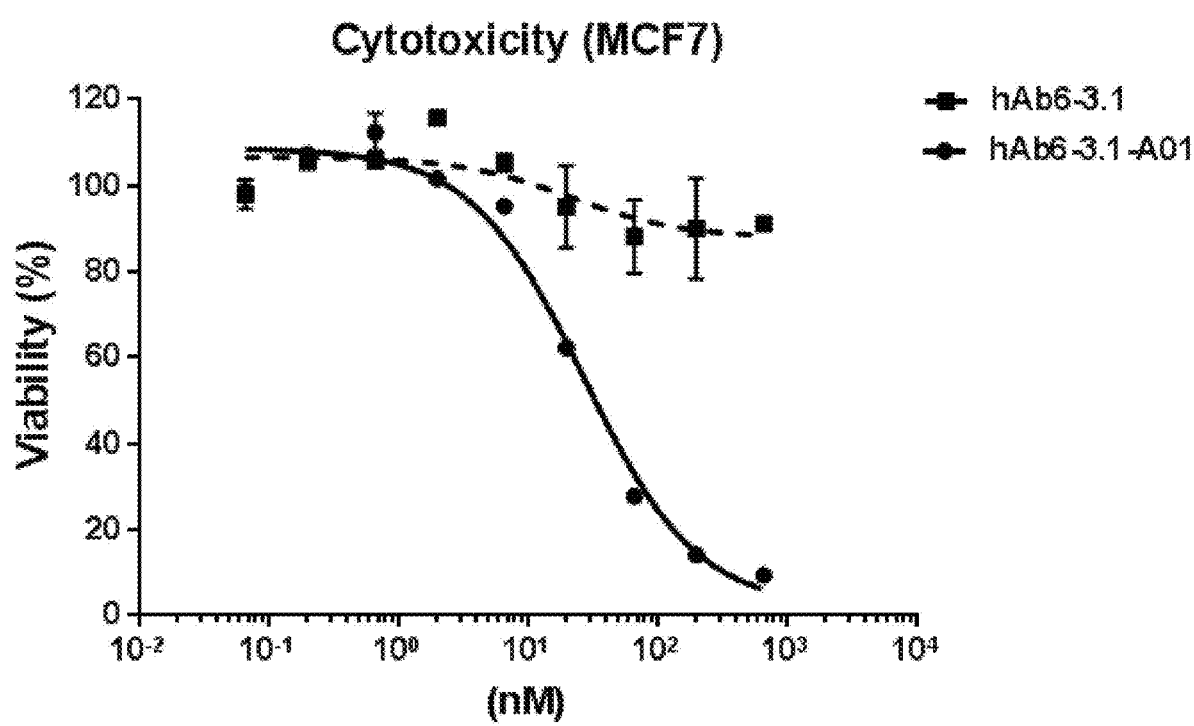

FIG. 26. Comparing the efficacy of hAb6-3.1-A01 in cell cytotoxicity on a SSEA4-expressing breast cell line MCF7 with antibody hAb6-3.1.

Figure 27:
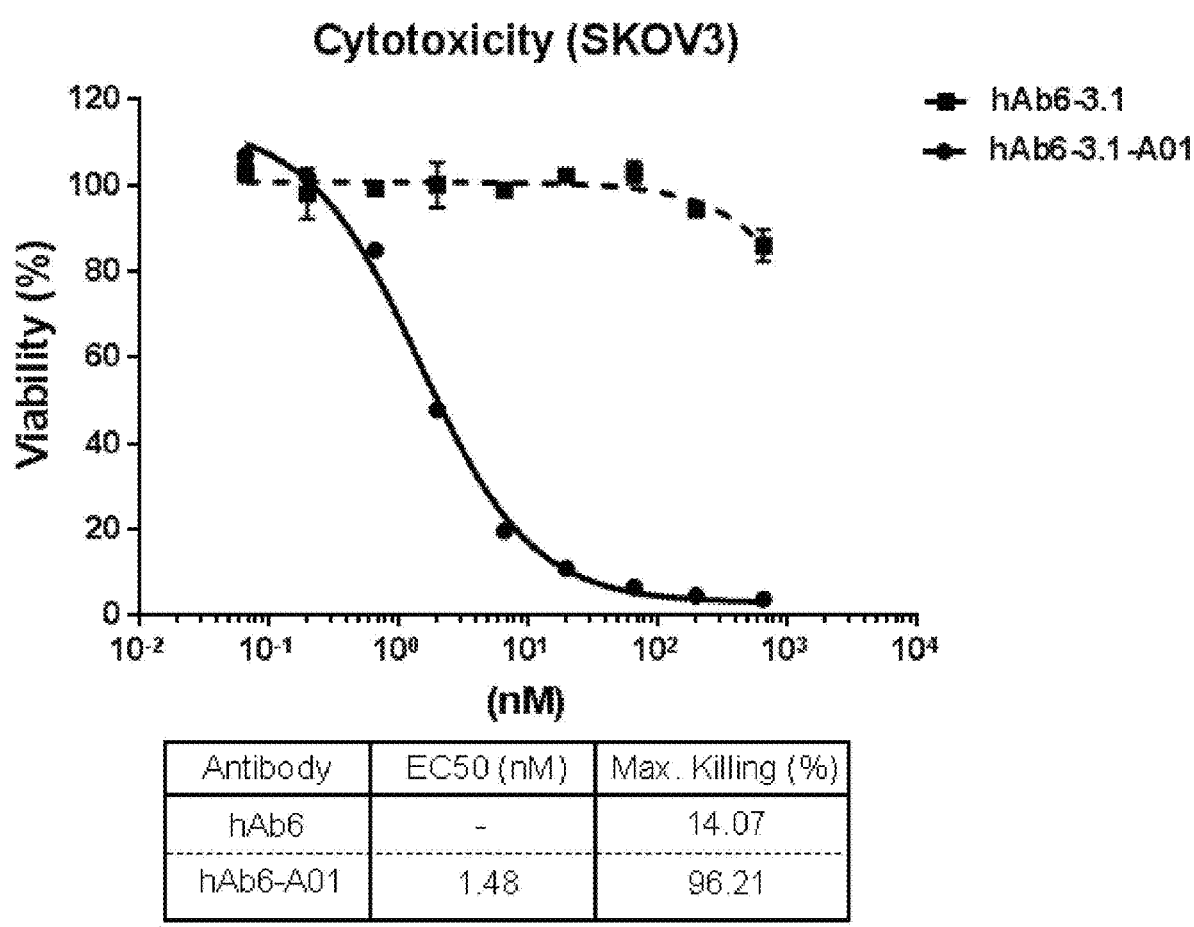

FIG. 27. Comparing the efficacy of hAb6-3.1-A01 in cell cytotoxicity on a SSEA4-expressing ovarian cell line SKOV3 with antibody hAb6-3.1.

DETAILED DESCRIPTIONS

Accordingly, antibody methods and compositions directed to the markers for use in diagnosing and treating a broad spectrum of cancers are provided. Anti-SSEA4 antibodies was developed and disclosed herein. Methods of use include, without limitation, cancer therapies and diagnostics. The antibodies described herein can bind to a broad spectrum of SSEA4-expressing tumor cells, thereby facilitating cancer diagnosis and treatment. Cells that can be targeted by the antibodies include carcinomas, such as those in brain, lung, breast, oral, esophageal, stomach, liver, bile duct, pancreatic, colon, kidney, cervical, ovarian, prostate cancer, etc.

Definitions

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Unless specified otherwise, in the polynucleotide notation used herein, the left-hand direction is 5'-terminal and the right-hand direction is 3'-terminal; in the peptide notation used herein, the left-hand direction is the amino-terminal (N-terminal) direction and the right-hand direction is the carboxyl-terminal (C-terminal) direction, in accordance with standard usage and convention.

The term "polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction.

The term "oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "vector" as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except proline.

The term "universal glycan" refers to the glycan sequence $Sia_2(\alpha 2\text{-}6)Gal_2GlcNAc_2Man_3GlcNAc_2$. The structure is

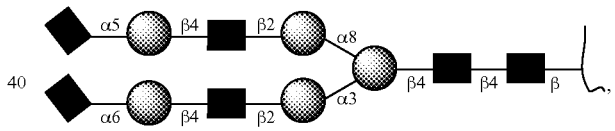

wherein ◆ is sialic acid (Sia); ◉ is galactose (Gal); ■ is N-Acetylglucosamine (GlcNAc); ● Mannose (Man).

The term "antigen" as used herein is defined as a substance capable of eliciting an immune response. Said immune response may involve either antibody production, or the activation of specific immunologically-competent cells, or both.

The term "epitope" refers to a unit of structure conventionally bound by an immunoglobulin $V_H/V_L$ pair. An epitope defines the minimum binding site for an antibody, and thus represent the target of specificity of an antibody.

As used herein, the term "immunogen" refers to an antigen capable of inducing the production of an antibody.

As used herein, the term "immunogenicity" generally refers to the ability of an immunogen or antigen to stimulate an immune response.

The term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding" refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less. In an additional or an alternative embodiment, the binding of the antibodies to their respective antigens is termed specific in terms of the antibody specificity. The term "specific" here is generally used to refer to the situation in which one member of a binding pair will not show any significant binding to molecules other than its specific binding partner (s) and e.g. has less than about 30%, preferably 20%, 15%, 10%, 5%, or 1% cross-reactivity with any other molecule other than those specified herein.

The term "binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

As used herein, the term "dissociation constant ($K_d$)" is a specific type of equilibrium constant that measures the propensity of a larger object to dissociate reversibly into smaller components, as when a complex falls apart into its component molecules. For a reaction $A_xB_y \rightleftharpoons xA+yB$, the dissociation constant is defined $K_d=[A]^x[B]^y/[A_xB_y]$, wherein [A], [B], and [$A_xB_y$] are the concentration of A, B, and $A_xB_y$, respectively. In particular, the $K_d$ value is determined by Biacore surface plasmon resonance system or enzyme-linked immunosorbent assay (ELISA).

As used herein, an antibody that "specifically binds to SSEA4 is intended to refer to an antibody that binds to SSEA4 with a $K_D$ of $1\times10^{-7}$ M or less, more preferably $5\times10^{-8}$ M or less, more preferably $1\times10^{-8}$ M or less, more preferably $5\times10^{-9}$ M or less or binds to SSEA-4 with a $K_D$ of between $1\times10^{-8}$ M and $1\times10^{-10}$ M or less.

The term K "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

The term "half maximal effective concentration ($EC_{50}$)" refers to the concentration of a drug, antibody or toxicant which induces a response halfway between the baseline and maximum after a specified exposure time. It is used as a measure of drug's potency.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g. bispecific antibodies) and may also include certain antibody fragments. Most antibodies are glycoproteins having the same structural characteristics: two heavy chains and two light chains linked to each other by disulfide bonds. The light chain includes a variable domain ($V_L$) and a constant domain ($C_L$); while the heavy chain includes a variable domain ($V_H$) and three constant domains ($C_H1$, $C_H2$ and $C_H3$, collectively referred to as $C_H$). The variable regions of both light ($V_L$) and heavy ($V_H$) chains determine binding recognition and specificity to the antigen. The $V_H$ and $V_L$ regions can be further subdivided into regions of hypervariability, termed hypervariable region (HVR), interspersed with regions that are more conserved, termed framework regions (FR). The constant region domains of the light ($C_L$) and heavy ($C_H$) chains confer important biological properties such as antibody chain association, secretion, trans-placental mobility, complement binding, and binding to Fc receptors (FcR). Depending on the amino acid sequences of the constant domains of their heavy chains, antibodies can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4$^{th}$ ed. (2000). An antibody may be part of a larger fusion molecule, formed by covalent or non-covalent association of the antibody with one or more other proteins or peptides. An antibody can be chimeric, human, humanized and/or affinity matured.

The "light chains" of antibodies (immunoglobulins) from any vertebrate species can be assigned to one of two distinct types, called kappa (κ) and lambda (λ), based on the amino acid sequences of their constant domains. In one embodiment, the chain is kappa type. In another embodiment, the chain is lamda type.

As used herein, "variable domain" refers to the portions of the light and heavy chains of antibody molecules that include amino acid sequences of hypervariable regions (HVRs), and framework regions (FRs). According to the methods used herein, the amino acid positions assigned to HVRs and FRs can be defined according to Kabat (*Sequences of Proteins of Immunological Interest*, National Institutes of Health, Bethesda, Md., 1987 and 1991). Amino acid numbering of antibodies or antigen binding fragments is also according to that of Kabat.

As used herein, the term "variable domain residue numbering as in Kabat" or "amino acid position numbering as in Kabat," and variations thereof, refers to the numbering system used for heavy chain variable domains or light chain variable domains of the compilation of antibodies in Kabat et al., *Sequences of Proteins of Immunological Interest*, 5$^{th}$ Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a standard Kabat numbered sequence.

As used herein, the term "framework region" (FR) residues are those variable domain residues other than the hypervariable region residues as herein defined.

As used herein, the term "hypervariable region" (HVR or HV) and "complementarity-determining region" (CDR) are used interchangeably, when used herein refers to the regions of an antibody variable domain which are hypervariable in sequence and/or form structurally defined loops. Generally, antibodies comprise six hypervariable regions; three in the $V_H$ (H-CDR1, H-CDR2, H-CDR3), and three in the $V_L$ (L-CDR1, L-CDR2, L-CDR3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5$^{th}$ Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "Contact" hypervariable regions are based on an analysis of the available complex crystal structures. "IMGT" (the international ImMunoGeneTics information system) provides unique numbering for immunoglobulin and T cell receptor variable domains and Ig superfamily V-like domains. The residues from each of these hypervariable regions defined by Kabat, AbM, Chothia, and Contact are noted below; IMGT are predicted on the website: http://www.imgt.org/

| Loop | Kabat | AbM | Chothia | Contact |
|------|-------|-----|---------|---------|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B | H26--H35B | H26--H32..34 | H30--H35B |
| | | (Kabat Numbering) | | |
| H1 | H31--H35 | H26--H35 | H26--H32 | H30--H35 |
| | | (Chothia Numbering) | | |
| H2 | H50--H65 | H50--H58 | H52--H56 | H47--H58 |
| H3 | H95--H102 | H95--H102 | H95--H102 | H93--H101 |

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

The term "antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

As used herein, the term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinant engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

As used herein, the term "Fv region" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

As used herein, the term "Fab fragment" contains the Fv region, the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteines from the antibody hinge region.

The term "antigen-binding fragment", refers to full length or one or more fragments of an antibody that retains the ability to specifically bind to an antigen. It has been shown that the antigen-binding function of an antibody can be performed by fragments of a full-length antibody. Examples of binding fragments encompassed within the term "antigen-binding fragment" include a Fab fragment; a Fv fragment; a single chain Fv (scFv) fragment; a diabody; a Fab'-SH fragment, which is the designation herein for Fab' in which the cysteine residue(s) of the constant domains bear a free thiol group; a F(ab)$_2$ fragment, which is a bivalent fragment comprising two Fab fragments linked by a disulfide bridge at the hinge region; a Fd fragment consisting of the V$_H$ and C$_H$1 domains; a dAb fragment (Ward et al., 1989 Nature 341:544-546), which consists of a V$_H$ domain; a dsFv fragment, two different disulfide-stabilized Fv antibody fragments connected by flexible linker peptides; and an isolated complementarity determining region (CDR); or any fusion proteins comprising such antigen-binding fragment.

The term "single-chain Fv" or "scFv" antibody fragments comprise the V$_H$ and V$_L$ domains of antibody, wherein these domains are present in a single polypeptide chain. Generally, the scFv polypeptide further comprises a polypeptide linker between the V$_H$ and V$_L$ domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (V$_H$) connected to a light-chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

The term "monoclonal antibody (mAb)" as used herein refers to an antibody obtained from a population of substantially homogeneous antibodies, e.g., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different epitopes, each monoclonal antibody of a monoclonal antibody is directed against a single epitope on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The term "chimeric antibodies" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass. In particular, in the present invention the chimeric antibody may be a humanized antibody in which the antigen binding sequences/variable domains of a non-human antibody have been grafted onto human antibody framework regions. Such antibodies are so long as they exhibit the desired biological activity (U.S. Pat. No. 4,816,567; and Morrison et al., Proc. Natl. Acad. Sci. USA 81:6851-6855 (1984)).

As used herein, the term "humanized antibodies" are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann.

Allergy, *Asthma & Immunol.* 1:105-115 (1998); Harris, *Biochem. Soc. Transactions* 23:1035-1038 (1995); Hurle and Gross, *Curr. Op. Biotech.* 5:428-433 (1994).

The term "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured antibody" is one with one or more alterations in one or more HVRs thereof which result in an improvement in the affinity of the antibody for antigen, compared to a parent antibody which does not possess those alteration(s). In one embodiment, an affinity matured antibody has nano-molar or even pico-molar affinities for the target antigen. Affinity matured antibodies are produced by procedures known in the art. Marks et al. *BioTechnology* 10:779-783 (1992) describes affinity maturation by $V_H$ and $V_L$ domain shuffling. Random mutagenesis of CDR and/or framework residues is described by: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An "isolated antibody" is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In one embodiment, the antibody will be purified (1) to greater than 90% by weight of antibody as determined by, for example, the Lowry method, and in some embodiments more than 95% by weight, (2) to a degree sufficient to obtain at least 15 residues of N-terminal or internal amino acid sequence by use of, for example, a spinning cup sequenator, or (3) to homogeneity by SDS-PAGE under reducing or non-reducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

A "blocking antibody" or an "antagonist antibody" is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

The term "chimeric antigen receptor (CAR)" is an artificially constructed hybrid protein or polypeptide containing the antigen-binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" or "proliferative disorder" refer to disorders that are associated with some degree of abnormal cell proliferation. In one embodiment, the cell proliferative disorder is cancer.

The term "tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" or "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include brain cancer, oral cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, stomach cancer, bile duct cancer, bladder cancer, hepatoma, breast cancer, colon cancer, bone cancer, colorectal cancer, endometrial or uterine carcinoma, salivary gland carcinoma, kidney cancer, liver cancer, prostate cancer, vulvar cancer, thyroid cancer, hepatic carcinoma, leukemia and other lymphoproliferative disorders, and various types of head and neck cancer.

As used herein, the term "individual" or "subject" is intended to include human and non-human animals. Preferred subjects include human patients in need of enhancement of an immune and/or anti-proliferative and/or anticancer therapeutic response. The methods are particularly suitable for treating human patients suitable for treatment of cancer cells in vivo.

As used herein, the term "theapeutic agent" is characterized by any agent that can reduce and/or inhibit hyperproliferative disease. Exemplary therapeutic agent can include, but no limited to, cytotoxic agent, chemotherapeutic agent, anti-proliferative agent, immune modulatoirs, hormonal modulators, cytokines as well as other anti-cancer substance and/or modalities.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, *vinca* alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. As used herein, a tumoricidal agent causes destruction of tumor cells. Cytotoxic agents and chemotherapeutic agents are not mutually exclusive.

Additionally or alternatively, a cytotoxin or cytotoxic agent may include any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The term "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside (Ara-C); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

As used herein, the term "cytokine" includes but not limited to examples listed in Kiefer et al. 2016, Immunol. Revs. 270:178-192. Exemplary suitable cytokines include but not limited to G-CSF, GM-CFS, IFNγ, IFNα, IL-1β, IL-2, IL-4, IL-6, IL-7, IL-9, IL-12, IL-13, IL-15, IL-17, IL-21, IL-23, and TNF.

In one embodiment, cytokine is linked to the binding domain via cross-links between lysine residues.

The term "therapeutic antibody" is an antibody useful in the treatment of disease. Examples of therapeutic antibodies are etaracizumab, atlizumab, tocilizumab, tacatuzumab tetraxetan, ruplizumab, ofatumumab, tefibazumab, bevacizumab, belimumab, tositumomab, blontuvetmab, mepolizumab, labetuzumab, arcitumomab, certolizumab pegol, ramucirumab, TRBS07, cetuximab, biciromab, obinutuzumab, trastuzumab, clivatuzumab tetraxetan, votumumab, zanolimumab, zalutumumab, adalimumab, fontolizumab, altumomab pentetate, canakinumab, igovomab, trastuzumab emtansine, alemtuzumab, rovelizumab, sulesomab, ranibizumab, FBTA05, bectumomab, rituximab, efungumab, gemtuzumab ozogamicin, imciromab, fanolesomab, motavizumab, visilizumab, pertuzumab, nivolumab, muromonab-cd3, oregovomab, edrecolomab, denosumab, capromab pendetide, efalizumab, infliximab, catumaxomab, girentuximab, abciximab, ertumaxomab, besilesomab, golimumab, basiliximab, eculizumab, ustekinumab, palivizumab, tamtuvetmab, nimotuzumab, pemtumomab, natalizumab, panitumumab, nofetumomab merpentan, omalizumab, ipilimumab, daclizumab, ibritumomab tiuxetan.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

The term "mammal" for purposes of treatment refers to any animal classified as a mammal, including humans, domestic and farm animals, and zoo, sports, or pet animals, such as dogs, horses, cats, cows, etc. In certain embodiments, the mammal is human.

The term "effective amount" refers to an amount effective, at dosages and for periods of time necessary, to achieve the desired therapeutic or prophylactic result.

As used herein, the term "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

As used herein, the term "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "pharmaceutically acceptable carrier" is one that is suitable for use with the subjects without undue adverse side effects (such as toxicity, irritation, and allergic response) commensurate with a reasonable benefit/risk ratio. Also, each carrier must be "acceptable" in the sense of being compatible with the other ingredients of the pharmaceutical composition. The carrier can be in the form of a solid, semi-solid, or liquid diluent, cream or a capsule. The carrier must be "acceptable" in the sense of being compatible with the other ingredients of the formulation, and is selected to minimize any degradation of the active agent and to minimize any adverse side effects in the subject.

The phrase "substantially similar", "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., $K_d$ values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

The term "Percentage (%) amino acid sequence identity" with respect to the amino acid sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). Specifically, the percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$(X \div Y) \times 100\%.$$

where X is the number of amino acid residues scored as identical matches by the sequence alignment program BLAST in that program's alignment of A and B, and where Y is the total number of amino acid residues in A or B, whichever is shorter.

Sequence Identity or homology with respect to a specified amino acid sequence is defined herein as the percentage of amino acid residues in a candidate sequence that are identical with the specified residues, after aligning the sequences and introducing gaps, if necessary, to achieve the maximum percent homology, and not considering any conservative substitutions as part of the sequence identity. None of N-terminal, C-terminal or internal extensions, deletions, or insertions into the specified sequence shall be construed as affecting homology. All sequence alignments called for in this invention are such maximal homology alignments. As discussed herein, minor variations in the amino acid sequences of proteins/polypeptides are contemplated as being encompassed by the presently disclosed and claimed inventive concept(s), providing that the variations in the amino acid sequence maintain at least 80% such as at least, 81%, 82%, 83%, 84%, 85%, 86%, 87%, 88%, 89%, 90%, 91%, 92%, 93%, 94%, 95%, 96%, 97%, 98% and 99%.

"Conservatively modified amino acid substitution" are contemplated. Conservative modified amino acid substitutions are those that take place within a family of amino acids that are related in their side chains. Genetically encoded amino acids are generally divided into families:

(1) acidic: aspartate (D), glutamate (E);
(2) basic: lysine (K), arginine (R), histidine (H);
(3) nonpolar: glycine (G), alanine (A), valine (V), leucine (L), isoleucine (I), proline (P), phenylalanine (F), methionine (M), tryptophan (W); and
(4) uncharged polar: asparagine (N), glutamine (Q), cysteine (C), serine (S), threonine (T), tyrosine (Y).

More preferred families are:
(3-1) aliphatic:alanine, valine, leucine and isoleucine;
(3-2) aromatic:phenylalanine, tryptophan, and tyrosine;
(4-1) aliphatic-hydroxyl:serine and threonine;
(4-2) amide-containing:asparagine and glutamine.

For example, it is reasonable to expect that an isolated substitution of a leucine with an isoleucine or valine, an aspartate with a glutamate, a threonine with a serine, or a similar replacement of an amino acid with a structurally related amino acid will not have a major effect on the binding or properties of the resulting molecule, especially if the substitution does not involve an amino acid within a framework site. Whether an amino acid change results in a functional peptide can readily be determined by assaying the specific activity of the polypeptide derivative. Fragments or analogs of proteins/polypeptides can be readily prepared by those of ordinary skill in the art. Preferred amino- and carboxyl-termini of fragments or analogs occur near boundaries of functional domains. Additional groups of amino acids may also be formulated using the principles described in, e.g., Creighton (1984) Proteins: Structure and Molecular Properties (2d Ed. 1993), W.H. Freeman and Company.

In certain embodiments, the conserved amino acid substitution can include sequence homologs which differs from the reference sequence (e.g. CDRs, VH, VL, Framework, full length etc) by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more substituted amino acid residues.

Derivatives

This disclosure also provides a method for obtaining an antibody specific for SSEA4. CDRs in such antibodies are not limited to the specific sequences of $V_H$ and $V_L$ identified in Table 2 and elsewhere herein and may include variants of these sequences that retain the ability to specifically bind SSEA4. Such variants may be derived from the sequences and concerved substitutions thereof listed below by a skilled artisan using techniques well known in the art.

| Original Residues | Exemplary Substitutions | Typical Substitutions |
| --- | --- | --- |
| Ala (A) | Val, Leu, Ile | Val |
| Arg (R) | Lys, Gln, Asn | Lys |
| Asn (N) | Gln | Gln |
| Asp (D) | Glu | Glu |
| Glu (E) | Asp | Asp |
| Cys (C) | Ser, Ala | Ser |
| Gln (Q) | Asn | Asn |
| Gly (G) | Pro, Ala, Gly | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala, Gly | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, an antibody of the invention comprises a heavy chain variable region comprising H-CDR1, H-CDR2 and H-CDR3 sequences and a light chain variable region comprising L-CDR1, L-CDR2 and L-CDR3 sequences, wherein one or more of these CDR sequences comprise specified amino acid sequences based on the preferred antibodies described herein, or conservative modifications thereof, and wherein the antibodies retain the desired functional properties of the anti-SSEA4 antibodies of the invention. Accordingly, the invention provides an isolated monoclonal antibody, or antigen-binding portion thereof, comprising a heavy chain variable region comprising H-CDR1, H-CDR2, and H-CDR3 sequences and a light chain variable region comprising L-CDR1, L-CDR2, and L-CDR3 sequences as well as conserved amino acid substituted variants thereof as well as full length sequences and homologs thereof comprising all 3 heavy chain and/or light chain CDRs.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the invention pertains to an isolated monoclonal antibody, or antigen-binding portion thereof, comprising a heavy chain variable region comprising H-CDR1, H-CDR2, and H-CDR3 sequences and a light chain variable region comprising L-CDR1, L-CDR2, and L-CDR3 sequences. Thus, such antibodies contain the $V_H$ and $V_L$ CDR sequences of monoclonal antibodies described herein yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) *Sequences of Proteins of Immunological Interest*, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the GenBank database. For example, the following heavy chain germline sequences found in the HCo7 HuMAb mouse are available in the accompanying GenBank accession numbers: 1-69 (NG_0010109, NT_024637 and BC070333), 3-33 (NG 0010109 and NT_024637) and 3-7 (NG_0010109 and NT_024637). As another example, the following heavy chain germline sequences found in the HCo12 HuMAb mouse are available in the accompanying GenBank accession numbers: 1-69 (NG_0010109, NT_024637 and BC070333), 5-51 (NG 0010109 and NT_024637), 4-34 (NG_0010109 and NT_024637), 3-30.3 (AJ556644) and 3-23 (AJ406678).

The CDR1, CDR2, and CDR3 sequences can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within each respective heavy or light chain CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies.

Another modification of the antibodies herein that is contemplated by the invention is PEGylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

In certain embodiments of the methods of engineering antibodies of the invention, mutations can be introduced randomly or selectively along all or part of an anti-PD-1 antibody coding sequence and the resulting modified anti-SSEA4 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule. In certain embodiments, the nucleic acid is expressed by a vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Exemplary nucleic acids molecules of the invention are those encoding the $V_H$ and $V_L$ amino acid sequences of the exemplary Ab6 monoclonal antibodies (see Tables 2A-2D).

Sequences with exemplary amino acid substitution on framework region (FR) are shown in TABLE 2B. Confirmation of the binding activity to SSEA4 and to SSEA4-expressing cells are demonstrated by binding assays as illustrated in the examples section. We confirmed that binding affinity function is conserved and retained even in exemplary variants with up to ⅗ amino acid substitutions on the framework of respective exemplary light chain and heavy chain.

Sequences with exemplary non-conservatively modified amino acid substitution on CDR are shown in Table 2C. Confirmation of the binding activity to SSEA4 and to SSEA4-expressing cells are demonstrated by binding assays as illustrated in the examples section. We confirmed that binding affinity and function are conserved and retained in exemplary variants with the following non-limiting exemplary amino acid substitutions on CDRs of light chain and heavy chain such as, for example, but not limited to, Heavy chain: A100R, N31S, T62A. Light chain: S52Y.

Sequences with exemplary conservatively modified amino acid substitution on CDR are shown in Table 2D. Confirmation of the binding activity to SSEA4 and to SSEA4-expressing cells are demonstrated by binding assays as illustrated in the examples section. We confirmed that binding affinity and function are conserved and retained in exemplary variants with non-limiting exemplary amino acid substitutions on CDRs of light chain and heavy chain, such as, for example, but not limited to, Heavy chain: V50A, G53A, S35T. Light chain: V30I/A, G91A, Y94F

TABLE 2A

Exemplary Parental Antibody chAb6 sequences (No. 01x)

| Antibody/SEQUENCE | SEQ ID Nos: | Amino Acid or nucleic acid sequence |
|---|---|---|
| H-CDR1 | No. 10 | NYGVS |
| H-CDR2 | No. 11 | VIWGDGSTNYHSTLRS |
| H-CDR3 | No. 12 | PGAGYAMDY |
| Heavy chain variable domain | No. 13 | QVQLKESGPGLVAPSQSLSITCTVSGFSLKNYGVSWVRQPPGKGLEWLGVIWGDGSTNYHSTLRSRLTISKDNSKSQLFLKLNRLQTDDTATYYCAKPGAGYAMDYWGQGTSVTVSS |
| Nucleotides of heavy chain | No. 14 | CAGGTGCAGCTGAAGGAGTCAGGACCTGGCCTGGTGGCGCCCTCACAGAGCCTGTCCATCACATGCACTGTCTCAGGGTTCTCATTAAAAAACTATGGTGTAAGCTGGGTTCGCCAGCCTCCAGGAAAGGGTCTGGAGTGGCTGGGAGTAATATGGGGTGACGGGAGCACAAATTATCATTCAACTCTCAGATCCAGACTGACCATCAGCAAGGATAATTCCAAGAGCCAACTTTTCTTAAAACTGAACAGACTGCAAACTGATGACACAGCCACGTACTACTGTGCCAAACCTGGGGCGGGTTATGCTATGGACTACTGGGGTCAAGGAACCTCAGTCACCGTCTCCTCA |
| L-CDR1 | No. 15 | SASSSVSYMH |
| L-CDR2 | No. 16 | DTSKLTS |
| L-CDR3 | No. 17 | FQGSGYPLT |
| Light chain variable domain | No. 18 | QIVLTQSPAIIVISVYPGEKVTMTCSASSSVSYMHWYQQKSSTSPKLWIYDTSKLTSGVPGRFSGSGSGNSYSLTISSMEAEDVATYYCFQGSGYPLTFGGGTKLEIKR |
| Nucleotides of light chain | No. 19 | CAAATTGTTCTCACCCAGTCTCCAGCAATCATGTCTGTATATCCAGGGGAAAAGGTCACCATGACCTGCAGTGCCAGCTCAAGTGTAAGTTACATGCACTGGTACCAGCAGAAGTCAAGCACCTCCCCCAAACTCTGGATTTATGACACATCCAAACTGACTTCTGGAGTCCCAGGTCGCTTCAGTGGCAGTGGGTCTGGAAACTCTTACTCTCTCACGATCAGCAGCATGGAGGCTGAAGATGTTGCCACTTATTACTGTTTTCAGGGGAGTGGGTACCCACTCACGTTCGGAGGGGGGACCAAGCTGGAAATAAAACGG |

TABLE 2B

Exemplary Antibody Embodiments with Modification in framework Region hAb6-2 sequence (No.02x)

| Heavy chain variable domain | No.23 | QVQLKESGPGLVAPSQTLSITCTVSGFSLKNYGVSWVRQPPGKGLEWIGVIWGDGSTNYHSTLRSRVTISKDNSKSQLFLKLNRLQTDDTATYYCAKPGAGYAMDYWGQGTSVTVSS |
|---|---|---|

TABLE 2B-continued

Exemplary Antibody Embodiments with Modification in framework Region

| | | |
|---|---|---|
| Light chain variable domain | No. 28 | EIVLTQSPAIQSVYPGEKVTMTCSASSSVSYMHWYQQKSSTSPKLWIYDTSKLTSGVPGRFSGSGSGNSYTLTISSMEAEDVATYYCFQGSGYPLTFGGGTKLEIKR |
| hAb6-3 sequence (No.03x) | | |
| Heavy chain variable domain | No. 33 | QVQLQESGPGLVAPSQTLSITCTVSGFSLKNYGVSWVRQPPGKGLEWIGVIWGDGSTNYHSTLRSRVTISKDNSKSQLFLKLNRLQTDDTATYYCAKPGAGYAMDYWGQGTLVTVSS |
| Light chain variable domain | No. 38 | EIVLTQSPAIQSVYPGEKVTMTCSASSSVSYMHWYQQKSSTSPKLWIYDTSKLTSGVPGRFSGSGSGNSYTLTISSMEAEDAATYYCFQGSGYPLTFGGGTKVEIKR |

TABLE 2C

Exemplary Antibody Embodiment with Non-conservative modification in CDRs hAb6-3.1 sequences (No.04x, H-CDR3:A100R)

| | | |
|---|---|---|
| H-CDR1 | No. 40 | NYGVS |
| H-CDR2 | No. 41 | VIWGDGSTNYHSTLRS |
| H-CDR3 | No. 42 | PG[R]GYAMDY |
| Heavy chain variable domain | No. 43 | QVQLQESGPGLVAPSQTLSITCTVSGFSLKNYGVSWVRQPPGKGLEWIGVIWGDGSTNYHSTLRSRVTISKDNSKSQLFLKLNRLQTDDTATYYCAKPG[R]GYAMDYWGQGTLVTVSS |
| Nucleotides of heavy chain | No. 44 | CAGGTGCAGCTGCAGGAGTCCGGACCAGGACTGGTGGCTCCCAGCCAGACCCTGTCTATCACCTGCACAGTGTCTGGCTTCTCCCTGAAGAACTACGGCGTGAGCTGGGTGAGACAGCCACCTGGCAAGGGACTGGAGTGGATCGGCGTGATCTGGGGCGACGGCTCTACCAATTATCACTCCACACTGAGGAGCCGGGTGACCATCTCCAAGGATAACTCCAAGAGCCAGCTGTTTCTGAAGCTGAATCGCCTGCAGACAGACGATACCGCCACATACTATTGCGCTAAGCCAGGCCGGGGCTACGCTATGGACTATTGGGGCCAGGGCACCCTGGTGACAGTGTCCAGC |
| L-CDR1 | No. 45 | SASSSVSYMH |
| L-CDR2 | No. 46 | DTSKLTS |
| L-CDR3 | No. 47 | FQGSGYPLT |
| Light chain variable domain | No. 48 | EIVLTQSPAIQSVYPGEKVTMTCSASSSVSYMHWYQQKSSTSPKLWIYDTSKLTSGVPGRFSGSGSGNSY |

TABLE 2C-continued

Exemplary Antibody Embodiment with Non-conservative modification in CDRs

|  |  |  |
|---|---|---|
|  |  | TLTISSMEAEDAATYYCFQGSGYP |
|  |  | LTFGGGTKVEIKR |
| Nucleotides of light chain | No.49 | GAGATCGTGCTGACCCAGTCTCCTGCCA |
|  |  | TCCAGTCCGTGTACCCAGGCGAGAAGG |
|  |  | TGACCATGACATGTTCCGCTTCTTCCAG |
|  |  | CGTGAGCTACATGCATTGGTATCAGCAG |
|  |  | AAGTCTTCCACATCTCCCAAGCTGTGGA |
|  |  | TCTACGACACCTCTAAGCTGACATCCGG |
|  |  | AGTGCCTGGCAGGTTCTCTGGATCCGGA |
|  |  | AGCGGCAACAGCTATACCCTGACAATCA |
|  |  | GCTCTATGGAGGCTGAGGATGCCGCTAC |
|  |  | CTACTATTGTTTCCAGGGCTCTGGCTATC |
|  |  | CCCTGACCTTTGGCGGCGGCACAAAGG |
|  |  | TGGAGATCAAGCGT | hAb6-3.2 sequences (No.05x, H-CDR1:N31S and H-CDR3:A100R)

| H-CDR1 | No.50 | SYGVS |
| H-CDR2 | No.51 | VIWGDGSTNYHSTLRS |
| H-CDR3 | No.52 | PGRGYAMDY |
| Heavy chain variable domain | No.53 | QVQLQESGPGLVAPSQTLSI |
|  |  | TCTVSGFSLKSYGVSWVRQ |
|  |  | PPGKGLEWIGVIWGDGSTN |
|  |  | YHSTLRSRVTISKDNSKSQLF |
|  |  | LKLNRLQTDDTATYYCAKPG |
|  |  | RGYAMDYWGQGTLVTVSS |
| Nucleotides of heavy chain | No.54 |  |
| L-CDR1 | No.55 | SASSSVSYMH |
| L-CDR2 | No.56 | DTSKLTS |
| L-CDR3 | No.57 | FQGSGYPLT |
| Light chain variable domain | No.58 | EIVLTQSPAIQSVYPGEKVTMTCS |
|  |  | ASSSVSYMHWYQQKSSTSPKLW |
|  |  | IYDTSKLTSGVPGRFSGSGSGNSY |
|  |  | TLTISSMEAEDAATYYCFQGSGYP |
|  |  | LTFGGGTKVEIKR |
| Nucleotides of light chain | No.59 |  | hAb6-3.3 sequences (No.06x, H-CDR2:T62A and H-CDR3:A100R)

| H-CDR1 | No.60 | NYGVS |
| H-CDR2 | No.61 | VIWGDGSTNYHSALRS |
| H-CDR3 | No.62 | PGRGYAMDY |

TABLE 2C-continued

Exemplary Antibody Embodiment with Non-conservative modification in CDRs

| | | |
|---|---|---|
| Heavy chain variable domain | No.63 | QVQLQESGPGLVAPSQTLSITCTVSGFSLKNYGVSWVRQPPGKGLEWIGVIWGDGSTNYHS[A]LRSRVTISKDNSKSQLFLKLNRLQTDDTATYYCAKPG[R]GYAMDYWGQGTLVTVSS |
| Nucleotides of heavy chain | No.64 | |
| L-CDR1 | No.65 | SASSSVSYMH |
| L-CDR2 | No.66 | DTSKLTS |
| L-CDR3 | No.67 | FQGSGYPLT |
| Light chain variable domain | No.68 | EIVLTQSPAIQSVYPGEKVTMTCSASSSVSYMHWYQQKSSTSPKLWIYDTSKLTSGVPGRFSGSGSGNSYTLTISSMEAEDAATYYCFQGSGYPLTFGGGTKVEIKR |
| Nucleotides of light chain | No.69 | | hAb6-3.4 sequences (No.07x, L-CDR2:S52Y and H-CDR3:A100R)

| | | |
|---|---|---|
| H-CDR1 | No.70 | NYGVS |
| H-CDR2 | No.71 | VIWGDGSTNYHSTLRS |
| H-CDR3 | No.72 | PG[R]GYAMDY |
| Heavy chain variable domain | No.73 | QVQLQESGPGLVAPSQTLSITCTVSGFSLKNYGVSWVRQPPGKGLEWIGVIWGDGSTNYHSTLRSRVTISKDNSKSQLFLKLNRLQTDDTATYYCAKPG[R]GYAMDYWGQGTLVTVSS |
| Nucleotides of heavy chain | No.74 | |
| L-CDR1 | No.75 | SASSSVSYMH |
| L-CDR2 | No.76 | DT[Y]KLTS |
| L-CDR3 | No.77 | FQGSGYPLT |
| Light chain variable domain | No.78 | EIVLTQSPAIQSVYPGEKVTMTCSASSSVSYMHWYQQKSSTSPKLWIYDT[Y]KLTSGVPGRFSGSGSGNSYTLTISSMEAEDAATYYCFQGSGYPLTFGGGTKVEIKR |
| Nucleotides of light chain | No.79 | |

TABLE 2D

| Exemplary Antibody embodiment with Conservative modification in CDRs |
| --- | hAb6-3.101 sequences (No.08x, H-CDR2:V50A and H-CDR3:A100R)

| | | |
|---|---|---|
| H-CDR1 | No.80 | NYGVS |
| H-CDR2 | No.81 | AIWGDGSTNYHSTLRS |
| H-CDR3 | No.82 | PGRGYAMDY |
| Heavy chain variable domain | No.83 | QVQLQESGPGLVAPSQTLSITCTVSGFSLKNYGVSWVRQPPGKGLEWIGAIWGDGSTNYHSTLRSRVTISKDNSKQLFLKLNRLQTDDTATYYCAKPGRGYAMDYWGQGTLVTVSS |
| Nucleotides of heavy chain | No.84 | |
| L-CDR1 | No.85 | SASSSVSYMH |
| L-CDR2 | No.86 | DTSKLTS |
| L-CDR3 | No.87 | FQGSGYPLT |
| Light chain variable domain | No.88 | EIVLTQSPAIQSVYPGEKVTMTCSASSSVSYMHWYQQKSSTSPKLWIYDTSKLTSGVPGRFSGSGSGNSYTLTISSMEAEDAATYYCFQGSGYPLTFGGGTKVEIKR |
| Nucleotides of light chain | No.89 | | hAb6-3.103 sequences (No.10x, H-CDR2:G53A and H-CDR3:A100R)

| | | |
|---|---|---|
| H-CDR1 | No.100 | NYGVS |
| H-CDR2 | No.101 | VIWADGSTNYHSTLRS |
| H-CDR3 | No.102 | PGRGYAMDY |
| Heavy chain variable domain | No.103 | QVQLQESGPGLVAPSQTLSITCTVSGFSLKNYGVSWVRQPPGKGLEWIGVIWADGSTNYHSTLRSRVTISKDNSKQLFLKLNRLQTDDTATYYCAKPGRGYAMDYWGQGTLVTVSS |
| Nucleotides of heavy chain | No.104 | |
| L-CDR1 | No.105 | SASSSVSYMH |
| L-CDR2 | No.106 | DTSKLTS |
| L-CDR3 | No.107 | FQGSGYPLT |

TABLE 2D-continued

Exemplary Antibody embodiment with Conservative modification in CDRs

| | | |
|---|---|---|
| Light chain variable domain | No.108 | EIVLTQSPAIQSVYPGEKVTMTCS ASSSVSYMHWYQQKSSTSPKLW IYDTSKLTSGVPGRFSGSGSGNSY TLTISSMEAEDAATYYCFQGSGYP LTFGGGTKVEIKR |
| Nucleotides of light chain | No.109 | | hAb6-3.105 sequences (No.12x, H-CDR1:S35T and H-CDR3:A100R)

| | | |
|---|---|---|
| H-CDR1 | No.120 | NYGV[T] |
| H-CDR2 | No.121 | VIWGDGSTNYHSTLRS |
| H-CDR3 | No.122 | PG[R]GYAMDY |
| Heavy chain variable domain | No.123 | QVQLQESGPGLVAPSQTLSI TCTVSGFSLKNYGV[T]WVRQ PPGKGLEWIGVIWGDGSTN YHSTLRSRVTISKDNSKSQLF LKLNRLQTDDTATYYCAKPG [R]GYAMDYWGQGTLVTVSS |
| Nucleotides of heavy chain | No.124 | |
| L-CDR1 | No.125 | SASSSVSYMH |
| L-CDR2 | No.126 | DTSKLTS |
| L-CDR3 | No.127 | FQGSGYPLT |
| Light chain variable domain | No.128 | EIVLTQSPAIQSVYPGEKVTMTCS ASSSVSYMHWYQQKSSTSPKLW IYDTSKLTSGVPGRFSGSGSGNSY TLTISSMEAEDAATYYCFQGSGYP LTFGGGTKVEIKR |
| Nucleotides of light chain | No.129 | | hAb6-3.106 sequences (No.13x, L-CDR1:V30I and H-CDR3:A100R)

| | | |
|---|---|---|
| H-CDR1 | No.130 | NYGVS |
| H-CDR2 | No.131 | VIWGDGSTNYHSTLRS |
| H-CDR3 | No.132 | PG[R]GYAMDY |
| Heavy chain variable domain | No.133 | QVQLQESGPGLVAPSQTLSI TCTVSGFSLKNYGVSWVRQ PPGKGLEWIGVIWGDGSTN YHSTLRSRVTISKDNSKSQLF LKLNRLQTDDTATYYCAKPG [R]GYAMDYWGQGTLVTVSS |

TABLE 2D-continued

Exemplary Antibody embodiment with Conservative modification in CDRs

| | | |
|---|---|---|
| Nucleotides of heavy chain | No.134 | |
| L-CDR1 | No.135 | SASSSISYMH |
| L-CDR2 | No.136 | DTSKLTS |
| L-CDR3 | No.137 | FQGSGYPLT |
| Light chain variable domain | No.138 | EIVLTQSPAIQSVYPGEKVTMTCS ASSSISYMHWYQQKSSTSPKLW IYDTSKLTSGVPGRFSGSGSGNSY TLTISSMEAEDAATYYCFQGSGYP LTFGGGTKVEIKR |
| Nucleotides of light chain | No.139 | | hAb6-3.107 sequences (No.14x, L-CDR1:V30A and H-CDR3:A100R)

| | | |
|---|---|---|
| H-CDR1 | No.140 | NYGVS |
| H-CDR2 | No.141 | VIWGDGSTNYHSTLRS |
| H-CDR3 | No.142 | PGRGYAMDY |
| Heavy chain variable domain | No.143 | QVQLQESGPGLVAPSQTLSI TCTVSGFSLKNYGVSWVRQ PPGKGLEWIGVIWGDGSTN YHSTLRSRVTISKDNSKSQLF LKLNRLQTDDTATYYCAKPG RGYAMDYWGQGTLVTVSS |
| Nucleotides of heavy chain | No.144 | |
| L-CDR1 | No.145 | SASSSASYMH |
| L-CDR2 | No.146 | DTSKLTS |
| L-CDR3 | No.147 | FQGSGYPLT |
| Light chain variable domain | No.148 | EIVLTQSPAIQSVYPGEKVTMTCS ASSSASYMHWYQQKSSTSPKLW IYDTSKLTSGVPGRFSGSGSGNSY TLTISSMEAEDAATYYCFQGSGYP LTFGGGTKVEIKR |
| Nucleotides of light chain | No.149 | | hAb6-3.108 sequences (No.15x, L-CDR3:G91A and H-CDR3:A100R)

| | | |
|---|---|---|
| H-CDR1 | No.150 | NYGVS |
| H-CDR2 | No.151 | VIWGDGSTNYHSTLRS |
| H-CDR3 | No.152 | PGRGYAMDY |
| Heavy chain variable domain | No.153 | QVQLQESGPGLVAPSQTLSI TCTVSGFSLKNYGVSWVRQ PPGKGLEWIGVIWGDGSTN |

TABLE 2D-continued

Exemplary Antibody embodiment with Conservative modification in CDRs

| | | |
|---|---|---|
| | | YHSTLRSRVTISKDNSKSQLF |
| | | LKLNRLQTDDTATYYCAKPG |
| | | RGYAMDYWGQGTLVTVSS |
| Nucleotides of heavy chain | No.154 | |
| L-CDR1 | No.155 | SASSSVSYMH |
| L-CDR2 | No.156 | DTSKLTS |
| L-CDR3 | No.157 | FQASGYPLT |
| Light chain variable domain | No.158 | EIVLTQSPAIQSVYPGEKVTMTCS |
| | | ASSSVSYMHWYQQKSSTSPKLW |
| | | IYDTSKLTSGVPGRFSGSGSGNSY |
| | | TLTISSMEAEDAATYYCFQASGYP |
| | | LTFGGGTKVEIKR |
| Nucleotides of light chain | No.159 | | hAb6-3.110 sequences (No.17x, L-CDR3:Y94F and H-CDR3:A100R)

| | | |
|---|---|---|
| H-CDR1 | No.170 | NYGVS |
| H-CDR2 | No.171 | VIWGDGSTNYHSTLRS |
| H-CDR3 | No.172 | PGRGYAMDY |
| Heavy chain variable domain | No.173 | QVQLQESGPGLVAPSQTLSI |
| | | TCTVSGFSLKNYGVSWVRQ |
| | | PPGKGLEWIGVIWGDGSTN |
| | | YHSTLRSRVTISKDNSKSQLF |
| | | LKLNRLQTDDTATYYCAKPG |
| | | RGYAMDYWGQGTLVTVSS |
| Nucleotides of heavy chain | No.174 | |
| L-CDR1 | No.175 | SASSSVSYMH |
| L-CDR2 | No.176 | DTSKLTS |
| L-CDR3 | No.177 | FQGSGFPLT |
| Light chain variable domain | No.178 | EIVLTQSPAIQSVYPGEKVTMTCS |
| | | ASSSVSYMHWYQQKSSTSPKLW |
| | | IYDTSKLTSGVPGRFSGSGSGNSY |
| | | TLTISSMEAEDAATYYCFQGSGFP |
| | | LTFGGGTKVEIKR |
| Nucleotides of light chain | No.179 | |

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In an embodiment, the antibodies of the invention are human monoclonal antibodies. Such human monoclonal antibodies directed against SSEA4 can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice."

The HuMAb mouse (Medarex, Inc.) contains human immunoglobulin gene miniloci that encode unrearranged human heavy (L and y) and x light chain immunoglobulin sequences, together with targeted mutations that inactivate the endogenous L and K chain loci (see e.g., Lonberg, et al. (1994) *Nature* 368(6474): 856-859). Accordingly, the mice exhibit reduced expression of mouse IgM or K, and in response to immunization, the introduced human heavy and light chain transgenes undergo class switching and somatic mutation to generate high affinity human IgGK monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-PD-1 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-SSEA4 antibodies of the invention. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-PD-1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202).

The term "antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998).

The term "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

The term "inhibits growth" (e.g. referring to cells, such as tumor cells) is intended to include any measurable decrease in the cell growth when contacted with an anti-SSEA4 antibody as compared to the growth of the same cells not in contact with an anti-SSEA4 antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g. effector cell phagocytosis, ADCC, CDC, and/or apoptosis.

In another aspect, the present invention features an anti-SSEA4 antibody, or a fragment thereof, conjugated to a therapeutic moiety, such as a cytotoxin, a drug (e.g., an immunosuppressant) or a radiotoxin.

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to antibodies of the invention using linker technology. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. DrugDeliv. Rev.* 53:247-264.

Antibody-drug conjugates (ADC) can include targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004). thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

In certain embodiments the ADC has the formula AB-(L-D)p, wherein: AB is the antibody or binding fragments described herein, L is a linker; D is a suitable cytotoxic drug, and p can range from 1, 2, 3, 4, 5, 6, 7, 8, 9, 10, 11, 12, 13, 14, 15, or more.

Exemplary linker "L" suitable for ADC construction can include "L" selected from the group consisting of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), N-Succinimidyl (4-iodo-acetyl)aminobenzoate (STAB), glucuronidase substrate, and PEG.

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), monomethyl auristatin E (MMAE), monomethyl auristatin F (MMAF), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity.

Antibodies of the present invention also can be conjugated to a radioactive isotope to generate cytotoxic radiopharmaceuticals, also referred to as radioimmunoconjugates.

Bispecific Molecules

In another aspect, the present invention features bispecific molecules comprising an anti-SSEA4 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-SSEA4 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzyl ethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosing and Dosage

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-SSEA4 antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising an anti-SSEA4 antibody, as described herein. The kit may also further comprise instructions for use in the treatment of a hyperproliferative disease (such as cancer as described herein). In another embodiment, the anti-SSEA4 antibodies may be co-packaged in unit dosage form, such as for example, PD-1 modulating and/or CAR-T therapeutic agents.

In another aspect, the present disclosure provides therapeutic methods and compositions that can be administered in combination with any other "cell therapy" or adoptive immunotherapeutic modalities. Exemplary adoptive immunotherapeutic modalities are described in, for example, Maus et al, *Annu. Rev. Immunol.* 2014. 32:189-225; and can include Chimeric Antigen Receptor (CAR-T) therapy, anti-PD-1 therapy, anti-PD-L1 therapy, and anti-CTL4 therapy etc.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994)*J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The antibodies, antibody compositions and methods of the present invention have numerous in vitro and in vivo utilities involving. In a preferred embodiment, the antibodies of the present invention are human antibodies. For example, these molecules can be administered to cells in culture, in vitro or ex vivo, or to human subjects, e.g., in vivo, to enhance immunity in a variety of situations. Accordingly, in one aspect, the invention provides a method of modifying ADCC response in a subject comprising administering to the subject the antibody, or antigen-binding portion thereof, of the invention such that the ADCC response in the subject is modified. Preferably, the response is enhanced, stimulated or up-regulated.

Accordingly, in one embodiment, the invention provides a method of inhibiting growth of tumor cells in a subject, comprising administering to the subject a therapeutically effective amount of an anti-SSEA4 antibody, or antigen-binding portion thereof. Preferably, the antibody is a human anti-SSEA4 antibody (such as any of the human anti-SSEA4 antibodies described herein). Additionally or alternatively, the antibody may be a chimeric or humanized anti-SSEA4 antibody.

In certain embodiments, the combination of therapeutic antibodies discussed herein may be administered concurrently as a single composition in a pharmaceutically acceptable carrier, or concurrently as separate compositions with each antibody in a pharmaceutically acceptable carrier.

Antibodies to Inhibit Tumor Growth

Provided herein are novel recombinant anti-SSEA4 antibodies specifically binding to SSEA4 or its derivatives, and methods of their use in anti-tumor immunotherapies, such as the treatment of cancer. Once bound to a cancer antigen, antibodies can induce antibody-dependent cell-mediated cytotoxicity, activate the complement system, and inhibit the growth of tumor.

In one embodiment, SSEA4 is highly expressed on various tumor cells, including brain tumor cells, lung tumor cells, breast tumor cells, oral tumor cells, esophageal tumor cells, stomach tumor cells, liver tumor cells, bile duct tumor cells, pancreatic tumor cells, colon tumor cells, renal tumor cells, cervical tumor cells, ovarian tumor cells, prostate tumor cells.

In one embodiment, the monoclonal anti-SSEA4 antibody specifically binds to SSEA4 molecule.

In one embodiment, the compositions comprising the anti-SSEA4 antibody described herein are useful in anti-cancer therapies. In particular, the present embodiments provide the complementarity determining region (CDR) sequences of specific anti-SSEA4 antibody, which can be used in a variety of anti-SSEA4 binding portion. In particular, the present invention provides a humanized or chimeric antibody or an antigen-binding fragment thereof capable of binding to SSEA4 or its derivatives.

In certain embodiments, the CDR sequences are defined by Kabat method.

In certain embodiments, the anti-SSEA4 antibody has the activity of inhibiting of tumor growth.

In certain embodiments, the isolated anti-SSEA4 antibody is a monoclonal antibody. Monoclonal antibodies to SSEA4 can be made according to knowledge and skill in the art. For example, it can be made by injecting test subjects with human embryonic carcinoma cell and then isolating hybridomas expressing antibodies having the desired sequence or functional characteristics.

In one embodiment, the present disclosure provides an isolated monoclonal antibody or an antigen binding portion thereof that binds to SSEA4 wherein upon target binding the antibody has CDC inducing activity.

In one embodiment, the present disclosure provides an isolated monoclonal antibody or an antigen binding portion thereof that binds to SSEA4 wherein upon target binding the antibody has ADCC inducing activity.

In one aspect, the present disclosure provides an isolated monoclonal antibody or an antigen-binding fragment thereof comprising: (i) a heavy chain variable region selected from SEQ ID Nos. 13, 23, 33, 43, 53, 63, 73, 83, 103, 123, 133, 143, 153, and 173 or a conserved sequence homologs of at least 80%, 81%, 82%, 83%, 84%, 85%, 86%, 87%, 88%, 89%, 90%, 91%, 91%, 92%, 93%, 94%, 95%, 96%, 97%, 98% or 99% sequence identity thereof, and (ii) a light chain variable region selected from SEQ ID Nos. 18, 28, 38, 48, 58, 68, 78, 88, 108, 128, 138, 148, 158, and 178 or a conserved sequence homologs of at least 80%, 81%, 82%, 83%, 84%, 85%, 86%, 87%, 88%, 89%, 90%, 91%, 91%, 92%, 93%, 94%, 95%, 96%, 97%, 98% or 99% sequence identity thereof.

In one aspect, the present disclosure provides an isolated monoclonal antibody or an antigen-binding fragment thereof comprising: (i) a heavy chain variable region selected from SEQ ID Nos. 13, 23, 33, 43, 53, 63, 73, 83, 103, 123, 133, 143, 153, and 173 or a conserved sequence homologs thereof containing less than or equal to 15, 14, 13, 12, 11, 10, 9, 8, 7, 6, 5, 4, 3, 2, or 1 amino acid substitutions; and (ii) a light chain variable region selected from SEQ ID Nos. 18, 28, 38, 48, 58, 68, 78, 88, 108, 128, 138, 148, 158, and 178 or a conserved sequence homologs thereof containing less than or equal to 15, 14, 13, 12, 11, 10, 9, 8, 7, 6, 5, 4, 3, 2, or 1 amino acid substitutions.

In one embodiment, the isolated monoclonal antibody or an antigen-binding fragment thereof further comprising: (i) a heavy chain variable region selected from SEQ ID Nos. 13, 23, 33, 43, 53, 63, 73, 83, 103, 123, 133, 143, 153, and 173 or 80% or more conserved sequence homologs thereof further comprising H-CDR1 selected from SEQ ID Nos. 10, 40, 50, 60, 70, 80, 100, 120, 130, 140, 150 and 170 or a conserved sequence homologs thereof containing less than or equal to 5, 4, 3, 2, or 1 amino acid substitutions; H-CDR2 selected from SEQ ID Nos. 11, 41, 51, 61, 71, 81, 101, 121, 131, 141, 151, and 171 or a conserved sequence homologs thereof containing less than or equal to 5, 4, 3, 2, or 1 amino acid substitutions, H-CDR3 selected from SEQ ID Nos: 12, 42, 52, 62, 72, 82, 102, 122, 132, 142, 152 and 172 or a conserved sequence homologs thereof containing less than or equal to 5, 4, 3, 2, or 1 amino acid substitutions; respectively, and (ii) a light chain variable region selected from SEQ ID Nos. 18, 28, 38, 48, 58, 68, 78, 88, 108, 128, 138, 148, 158, and 178 or 80% or more conserved sequence homologs thereof further comprising L-CDR1 selected from SEQ ID Nos. 15, 45, 55, 65, 75, 85, 105, 125, 135, 145, 155 and 175 or a conserved sequence homologs thereof containing less than or equal to 5, 4, 3, 2, or 1 amino acid substitutions; and L-CDR2 selected from SEQ ID Nos. 16, 46, 56, 66, 76, 86, 106, 126, 136, 146, 156 and 176 or a conserved sequence homologs thereof containing less than or equal to 5, 4, 3, 2, or 1 amino acid substitutions, and L-CDR3 selected from SEQ ID Nos: 17, 47, 57, 67, 77, 87, 107, 127, 137, 147, 157, and 177 or a conserved sequence homologs thereof containing less than or equal to 5, 4, 3, 2, or 1 amino acid substitutions.

In one embodiment, the isolated monoclonal antibody or an antigen-binding fragment thereof comprising: (i) a heavy chain variable region selected from SEQ ID Nos. 13, 23, 33, 43, 53, 63, 73, 83, 103, 123, 133, 143, 153, and 173 or a conserved sequence homologs thereof containing less than 10 amino acid substitutions further comprising H-CDR1 selected from SEQ ID Nos. 10, 40, 50, 60, 70, 80, 100, 120, 130, 140, 150 and 170; H-CDR2 selected from SEQ ID Nos. 11, 41, 51, 61, 71, 81, 101, 121, 131, 141, 151, and 171, H-CDR3 selected from SEQ ID Nos: 12, 42, 52, 62, 72, 82, 102, 122, 132, 142, 152 and 172; respectively, and (ii) a light chain variable region selected from SEQ ID Nos. 18, 28, 38, 48, 58, 68, 78, 88, 108, 128, 138, 148, 158, and 178 or a conserved sequence homologs thereof containing less than 10 amino acid substitutions further comprising L-CDR1 selected from SEQ ID Nos. 15, 45, 55, 65, 75, 85, 105, 125, 135, 145, 155 and 175; and L-CDR2 selected from SEQ ID Nos. 16, 46, 56, 66, 76, 86, 106, 126, 136, 146, 156 and 176, and L-CDR3 selected from SEQ ID Nos: 17, 47, 57, 67, 77, 87, 107, 127, 137, 147, 157, and 177.

In one aspect, the present disclosure provides an isolated monoclonal antibody or an antigen-binding fragment thereof comprising: (i) a heavy chain variable region selected from SEQ ID Nos. 13, 23, 33, 43, 53, 63, 73, 83, 103, 123, 133, 143, 153, and 173, and (ii) a light chain variable region selected from SEQ ID Nos. 18, 28, 38, 48, 58, 68, 78, 88, 108, 128, 138, 148, 158, and 178 or a conserved sequence homologs thereof containing less than 10 amino acid substitutions further comprising L-CDR1 selected from SEQ ID Nos. 15, 45, 55, 65, 75, 85, 105, 125, 135, 145, 155 and 175; and L-CDR2 selected from SEQ ID Nos. 16, 46, 56, 66, 76, 86, 106, 126, 136, 146, 156 and 176, and L-CDR3 selected from SEQ ID Nos: 17, 47, 57, 67, 77, 87, 107, 127, 137, 147, 157, and 177.

In one aspect, the present disclosure provides an isolated monoclonal antibody or an antigen-binding fragment thereof comprising: (i) a heavy chain variable region selected from SEQ ID Nos. 13, 23, 33, 43, 53, 63, 73, 83, 103, 123, 133, 143, 153, and 173 or a conserved sequence homologs thereof containing less than 10 amino acid substitutions further comprising H-CDR1 selected from SEQ ID Nos. 10, 40, 50, 60, 70, 80, 100, 120, 130, 140, 150 and 170; H-CDR2 selected from SEQ ID Nos. 11, 41, 51, 61, 71, 81, 101, 121, 131, 141, 151, and 171, H-CDR3 selected from SEQ ID Nos: 12, 42, 52, 62, 72, 82, 102, 122, 132, 142, 152 and 172; respectively, and (ii) a light chain variable region selected from SEQ ID Nos. 18, 28, 38, 48, 58, 68, 78, 88, 108, 128, 138, 148, 158, and 178.

In one aspect, the present disclosure provides an isolated monoclonal antibody or an antigen-binding fragment thereof comprising the respective corresponding VH, VL and respective H-CDRs and L-CDRS as set forth in each variant in Tables 2A-2D.

As used herein, homolog or the conserved sequence homolog can include isolated monoclonal antibody or an antigen-binding fragment thereof targeting SSEA4 comprising the respective corresponding VH, VL and respective H-CDRs and L-CDRS having at least 80%, 81%, 82%, 83%, 84%, 85%, 86%, 87%, 88%, 89%, 90%, 91%, 91%, 92%, 93%, 94%, 95%, 96%, 97%, 98% or 99% sequence identity as compared to the reference sequence as disclosed herein AND/OR having less than or equal to 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions as compared to the reference sequence.

In certain embodiments, the anti-SSEA4 antibody is monoclonal antibody.

In certain embodiments, the anti-SSEA4 antibody is chimeric or humanized antibody.

In one aspect, the framework sequences are derived from human consensus framework sequences or human germline framework sequences.

In a further aspect, the heavy chain variable domain, antibody or antigen-binding fragment further comprises at least a $C_H1$ domain.

In a further aspect, the heavy chain variable domain, antibody or antigen-binding fragment further comprises a $C_H1$, a $C_H2$ and a $C_H3$ domain.

In a further aspect, the variable region light chain, antibody or antibody fragment further comprises a $C_L$ domain.

In a further aspect, the antibody further comprises a $C_H1$, a $C_H2$, a $C_H3$ and a $C_L$ domain.

In a further specific aspect, the antibody further comprises a human or murine constant domain.

In a still further aspect, the human constant region is selected from the group consisting of IgG1, IgG2, IgG3, IgG4.

In a further aspect, the nucleic acid further comprises a vector suitable for expression of the nucleic acid encoding any of the previously described anti-SSEA4 antibodies. In a still further specific aspect, the vector further comprises a host cell suitable for expression of the nucleic acid. In a still further specific aspect, the host cell is a eukaryotic cell or a prokaryotic cell. In a specific aspect, the eukaryotic cell is a mammalian cell, such as Chinese Hamster Ovary (CHO). In another aspect the cell is yeast cell.

In an embodiment, the invention provides for a process of making an anti-SSEA4 antibody or antigen binding fragment thereof, comprising culturing a host cell containing nucleic acid encoding any of the previously described anti-SSEA4 antibodies or antigen-binding fragment in a form suitable for expression, under conditions suitable to produce such antibody or fragment, and recovering the antibody or fragment.

In an embodiment, the invention provides for a composition comprising an anti-SSEA4 antibody or antigen-binding fragment thereof as provided herein and at least one pharmaceutically acceptable carrier.

In one aspect, the present disclosure provides an isolated monoclonal antibody or an antigen binding portion thereof that binds to SSEA4 wherein upon target binding the antibody has ADCC and CDC inducing activity.

Any of the antibodies described herein can be a full length antibody or an antigen-binding fragment thereof. In some examples, the antigen binding fragment is a Fab fragment, a F(ab')$_2$ fragment, or a single-chain Fv fragment. In some examples, the antigen binding fragment is a Fab fragment, a F(ab')$_2$ fragment, or a single-chain Fv fragment (scFv). In some examples, the isolated antibody is a human antibody, a humanized antibody, a chimeric antibody, or a single-chain antibody.

Any of the antibodies described herein has one or more characteristics of:

a) is a recombinant antibody, a monoclonal antibody, a chimeric antibody, a humanized antibody, a human antibody, an antibody fragment, a bispecific antibody, a monospecific antibody, a monovalent antibody, an IgG antibody, or derivative of an antibody;

b) is a human, murine, humanized, or chimeric antibody, antigen-binding fragment, or derivative of an antibody;

c) is a single-chain antibody fragment, a multibody, a Fab fragment, and/or an immunoglobulin of the IgG, IgM, IgA, IgE, IgD isotypes and/or subclasses thereof;

d) has one or more of the following characteristics: (i) mediates ADCC and/or CDC of cancer cells; (ii) induces and/or promotes apoptosis of cancer cells; (iii) inhibits proliferation of target cells of cancer cells; (iv) induces and/or promotes phagocytosis of cancer cells; and/or (v) induces and/or promotes the release of cytotoxic agents;

e) specifically binds the tumor-associated carbohydrate antigen, which is a tumor-specific carbohydrate antigen;

f) does not bind an antigen expressed on non-cancer cells, non-tumor cells, benign cancer cells and/or benign tumor cells; and/or g) specifically binds a tumor-associated carbohydrate antigen expressed on cancer stem cells and on normal cancer cells.

The antibodies are suitable bind to its target epitopes with a high affinity (low $K_D$ value), and preferably $K_D$ is in the nano-molar range or lower. Affinity can be measured by methods known in the art, such as, for example; surface plasmon resonance.

In certain embodiments, the exemplary anti-SSEA4 antibody or antigen-binding fragment inhibits or reduces the tumor growth by combined with one or more cytotoxic agent, chemotherapeutic agent or therapeutic antibody.

In an embodiment, the present invention provides a composition of bispecific antibody comprising an exemplary anti-SSEA4 antibody or antigen-binding fragment thereof fused to or linked by a spacer to a T cell-binding molecule including but not limited to anti-CD3 antibody or antigen-binding fragment thereof.

In another embodiment, the present invention provides a composition of chimeric antigen receptor (CAR) comprising an extracellular domain containing an exemplary anti-SSEA4 antibody or antigen-binding fragment thereof, a transmembrane domain that anchors the CAR to the cell membrane, and an intracellular domain which transmits an activation signal to the immune cells once the CAR engage with SSEA4. The CAR can be genetically/artificially expressed on immune cells including but not limited to T cell, NK cell, and NKT cell to target and kill cancer cells expressing SSEA4.

The present invention is further illustrated by the following examples which should not be construed as further limiting. The contents of all figures and all references, patents and published patent applications cited throughout this application are expressly incorporated herein by reference.

EXAMPLES

Example 1

Detection of Globo-Series Glycosphingolipids Expression on Various Cancer Cell Lines Cells ($1 \times 10^5$) of various cancer cell line, including brain tumor cell, lung tumor cells, breast tumor cells, oral tumor cells, esophageal tumor cells, stomach tumor cells, liver tumor cells, bile duct tumor cells, pancreatic tumor cells, colon tumor cells, renal tumor cells, cervical tumor cells, ovarian tumor cells, prostate tumor cells (Table 4) were stained with 0.5 µg Alexa Flour 488-conjugated anti-SSEA3 mAb (MC-631), anti-SSEA4 mAb (MC813-70), or allophycocyanin (APC)-conjugated anti-GloboH mAb (VK9, a gift from Philip O. Livingston, Memorial Sloan-Kettering Cancer Center, New York) in 50 µL FACS buffer (PBS solution with 1% FBS) on ice for 30 min. For lectin staining, cells were incubated for 30 min on ice in lectin-binding buffer [1% BSA, 0.5× Carbo-Free Blocking buffer (Vector Laboratories), 2 mM $MgCl_2$, 2 mM $CaCl_2$] containing biotinylated lectin. After being washed twice with lectin-binding buffer, cells were incubated with streptavidin-APC (1:500 diluted in FACS buffer; Biolegend). After being washed twice with 200 µL FACS buffer, cells were re-suspended in 200 µL FACS buffer containing 1 µg/mL propidium iodide (PI) and subjected to analysis. Data acquisition was performed on a FACSCanto (BD Biosciences) with FACSDiva software (BD Biosciences), and data analyses were performed using FlowJo software (TreeStar). Live $PI^-$ cells were gated for analysis. For methanol washing, cells were washed and fixed with 4% (wt/vol) paraformaldehyde in PBS for 15 min at room temperature, followed by incubation in methanol for 10 min before staining with specific antibodies.

Example 2

Representative Methodology for Generating and Producing Exemplary Monoclonal Anti-SSEA4 Antibodies Hybridoma technology was employed for generating the monoclonal antibodies specific to and/or targeting SSEA4. For example, female Balb/c mice, aged 6 weeks old (Biolasco, Taiwan) were intraperitoneally injected with $10^7$ NCCIT cells three times at 2-week intervals. Sera were collected one week after the $3^{rd}$ immunization, and the titer of anti-SSEA4 IgG and/or IgM antibodies were measured by ELISA. ELISA was conducted by using 96-well assay plates coated with 0.1 µg of BSA-conjugated SSEA4. One week later, mice which met the fusion criteria were then given a final boost with $10^7$ NCCIT cells. Three days after the final boost, mice were sacrificed and the spleen cells from these mice were used for generating the hybridomas. The hybridoma clones positive to BSA-conjugated SSEA4 and negative to BSA were selected for further sub-cloning to ensure every hybridoma clone was derived from a single cell. In one exemplary run, a total of 10 SSEA4-positive hybridoma clones were selected from over 5,000 clones. Among these clones, only Ab6 is IgG, and the others are IgM antibodies. The subclass of Ab6 was further determined by antibody isotyping kit, and the result showed that the isotype of Ab6 is IgG3, kappa. Following the sequencing, the murine variable regions ($V_H$ and $V_L$) of Ab6 was PCR amplified and sub-cloned into an expression vector containing the constant region ($C_H$ and $C_L$) of human IgG1 to generate chAb6, a human-mouse chimeric antibody.

Example 3

Binding of Exemplary Anti-SSEA4 Antibodies to SSEA4 by ELISA

The binding affinity of exemplary chimeric and humanized anti-SSEA4 antibodies to SSEA4 were determined by ELISA. Briefly, antibodies were diluted in PBS at the indicated concentration and then allowed to incubate with BSA-conjugated SSEA4 in 96-well assay plates for 1 hour at room temperature. Following the wash cycles, HRP-conjugated goat anti-human IgG antibody (1:10,000 diluted in PBS, Jackson Immuno Research) was added to wells and incubated at room temperature for another one hour. After the wash cycles, TMB ELISA substrate (Abcam) was added for color development, and the reaction was stopped by adding equal volume of 2N $H_2SO_4$. The absorbance at O.D. 450 nm was read and recorded by M5 ELISA reader (Molecular Device). (FIG. 6A-6D)

Example 4

The binding affinity of chAb6 to a Pancreatic Cancer Cell Line HPAC

Figure 10A:
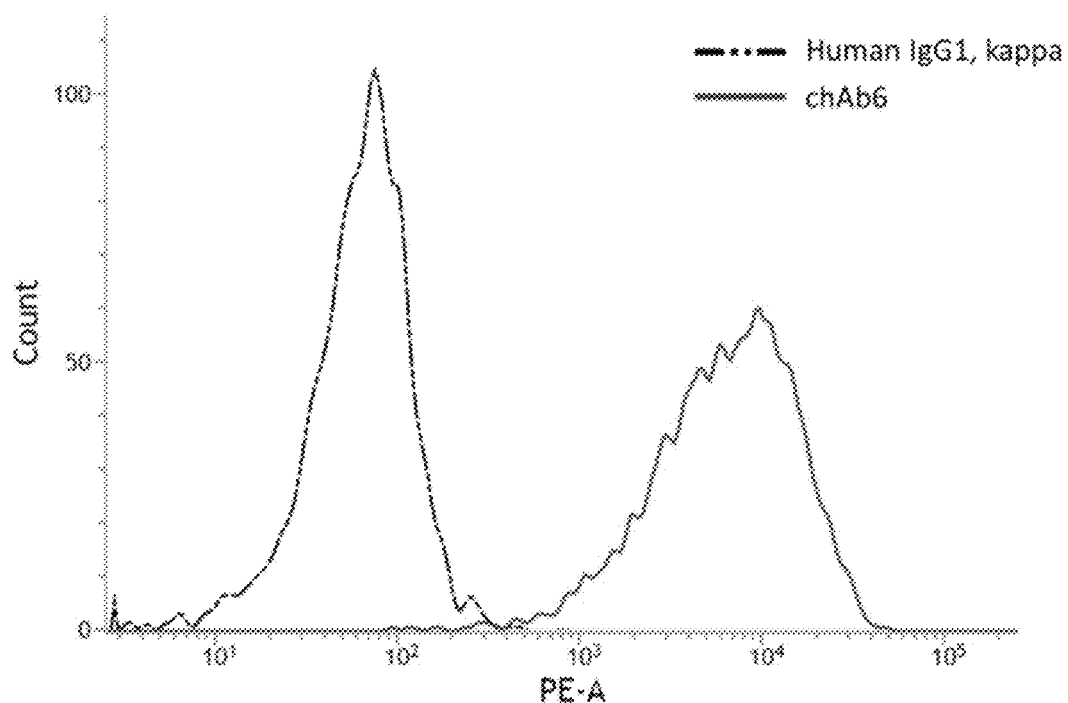
FIG. 10A-10B. Determination of the binding affinity of an exemplary chAb6 to a pancreatic cancer cell line HPAC by flow cytometry analysis.
Figure 10B:
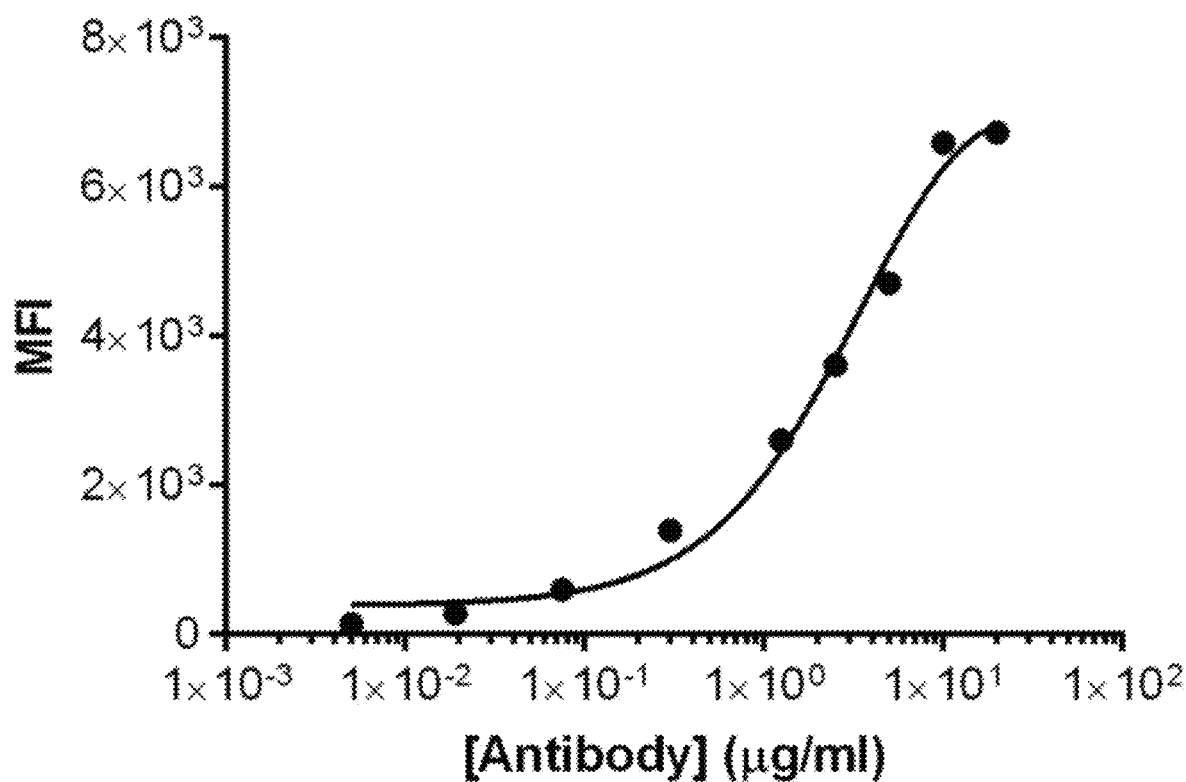
Figure 11A:
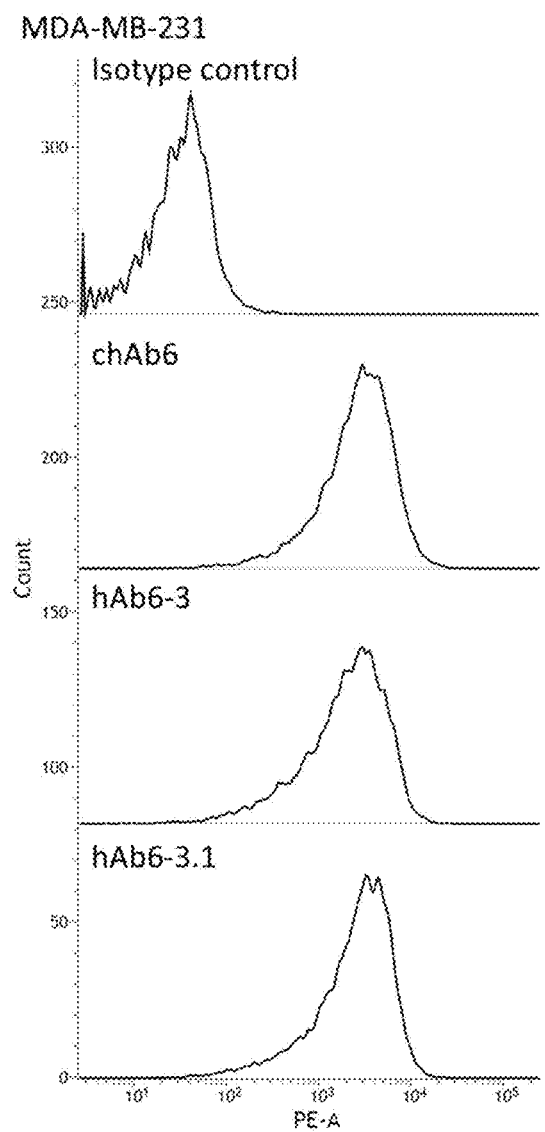
FIG. 11A-11B: The binding of exemplary chimeric and humanized Ab6s to breast and pancreatic cancer cell lines. The binding of chAb6, hAb6-3 and hAb6-3.1 to (11A) MDA-MB-231 and (11B) HPAC cells were examined by flow cytometry analysis. The antibody concentration used for staining was 5 microgram per milliliter.
Figure 11B:
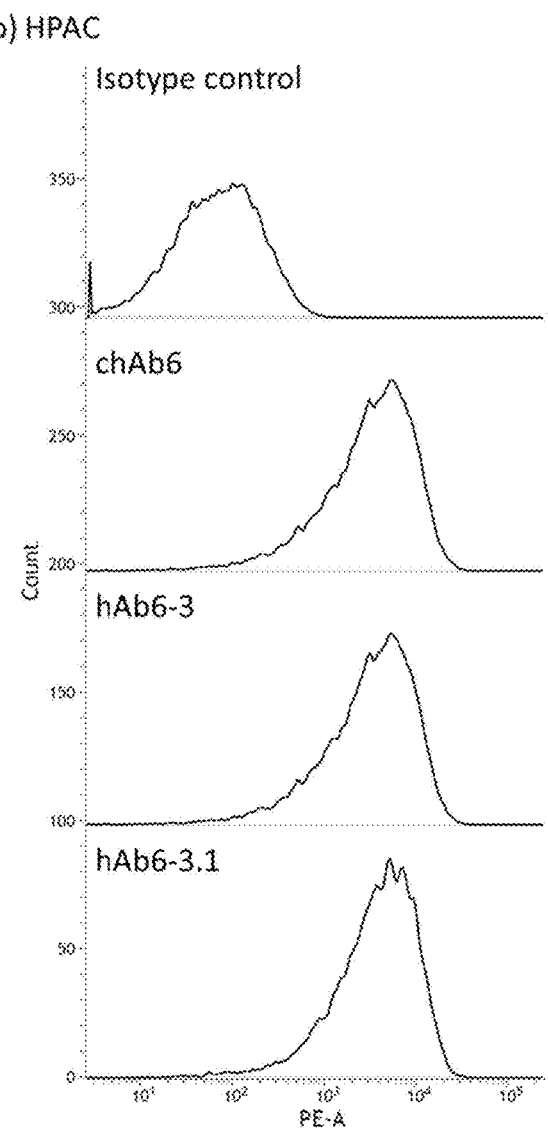
Figure 11C:
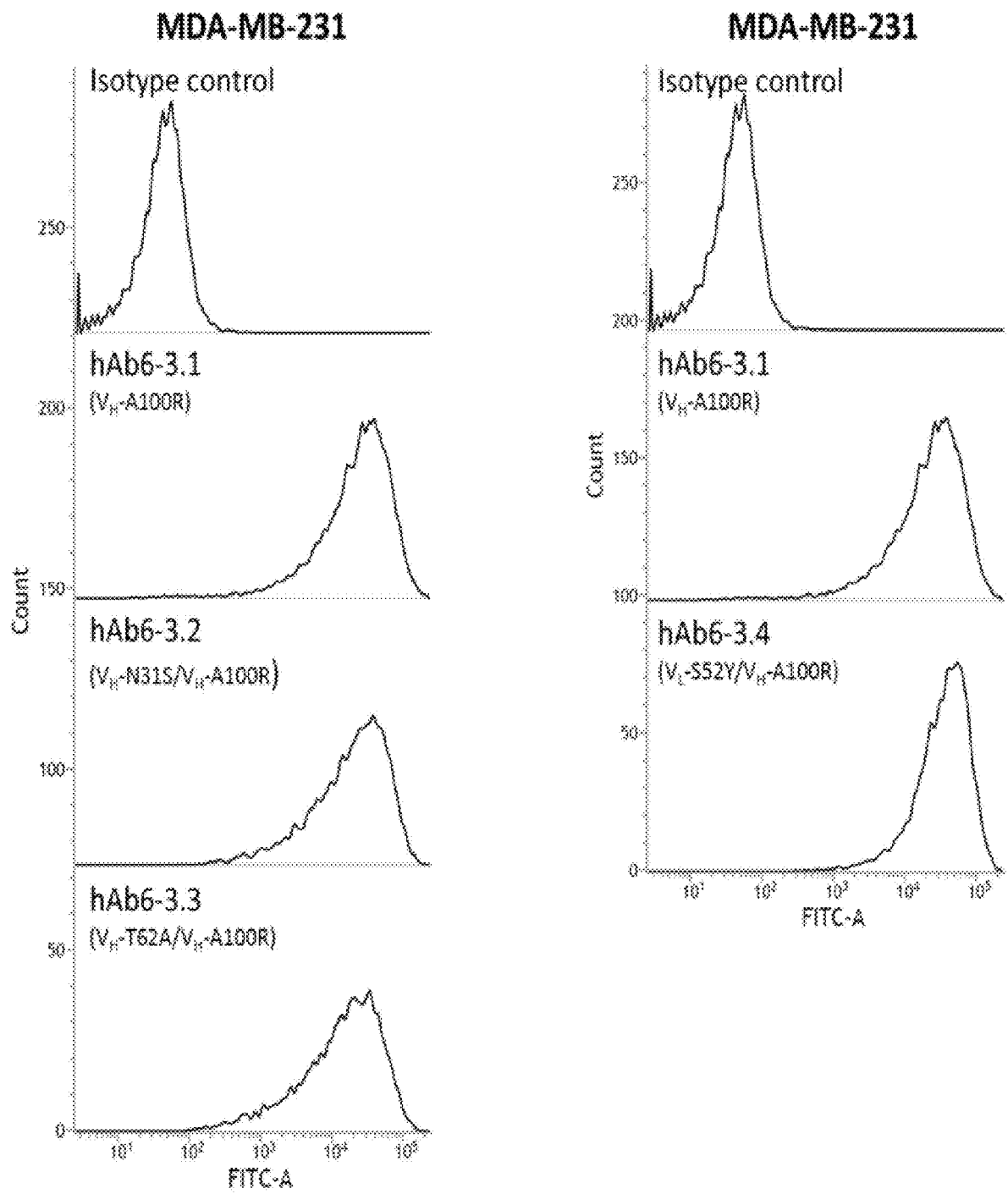
FIG. 11C-FIG. 11D.
Figure 11D:
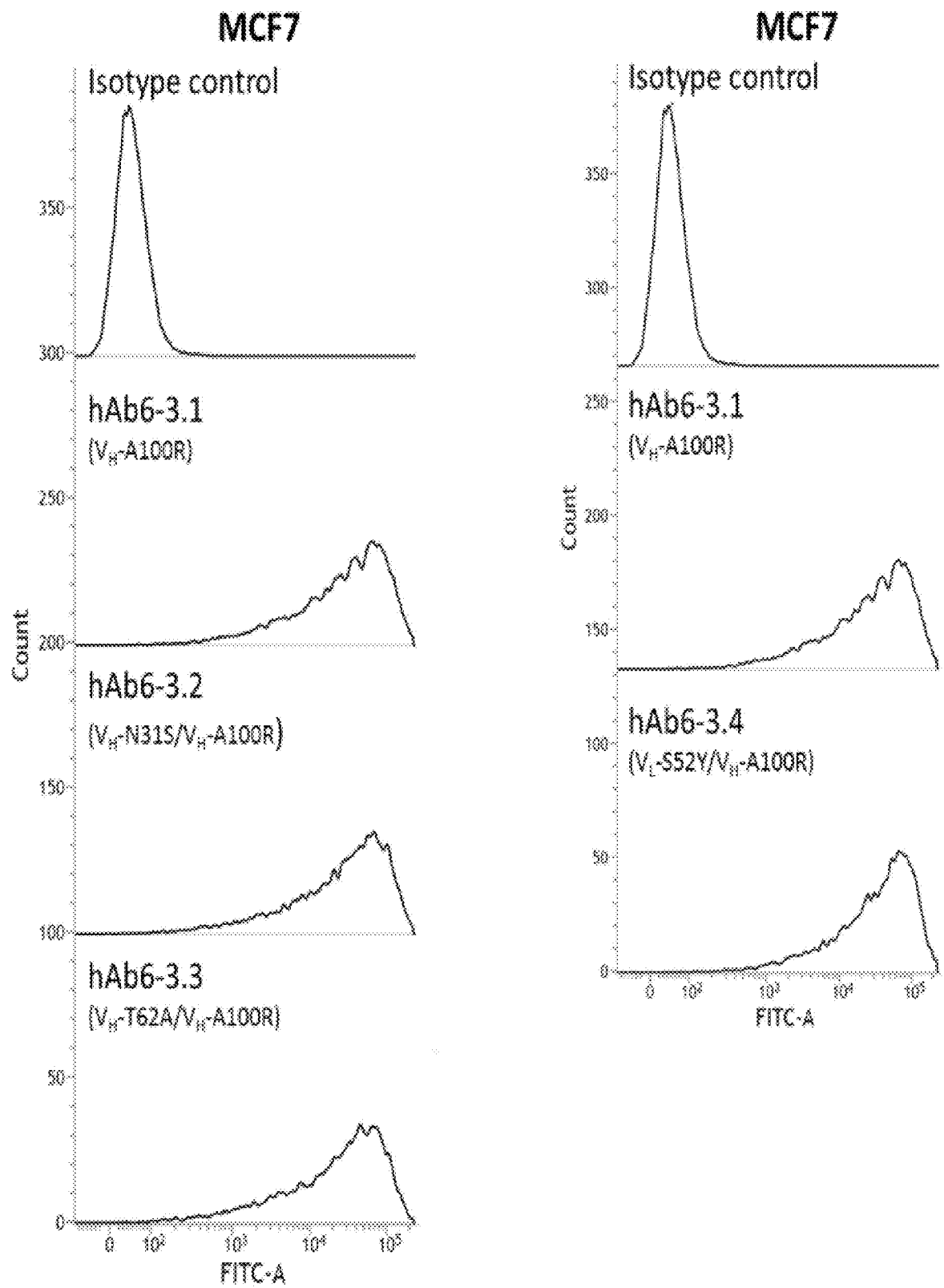
Figure 11E:
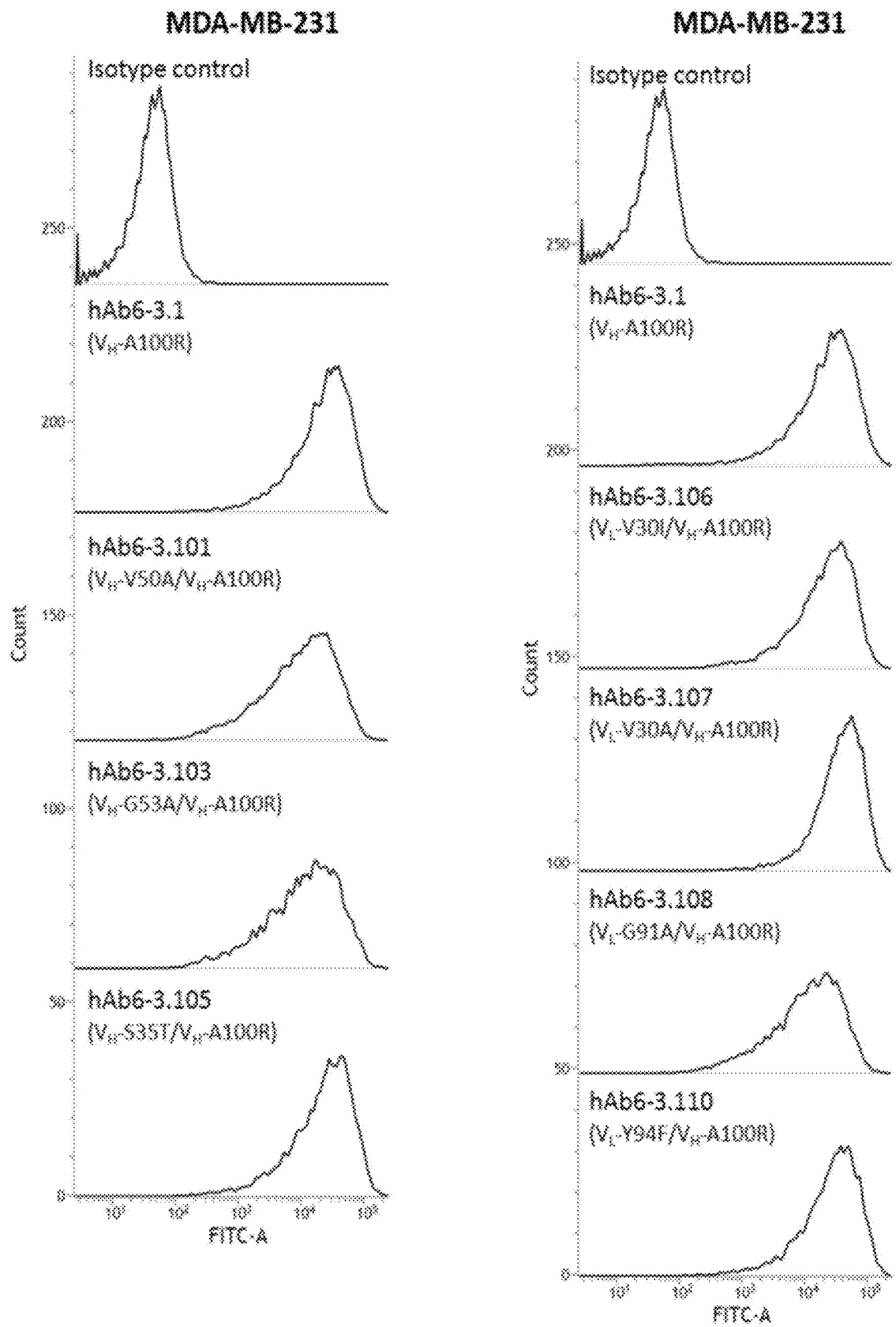
FIG. 11E-FIG. 11F.
Figure 11F:
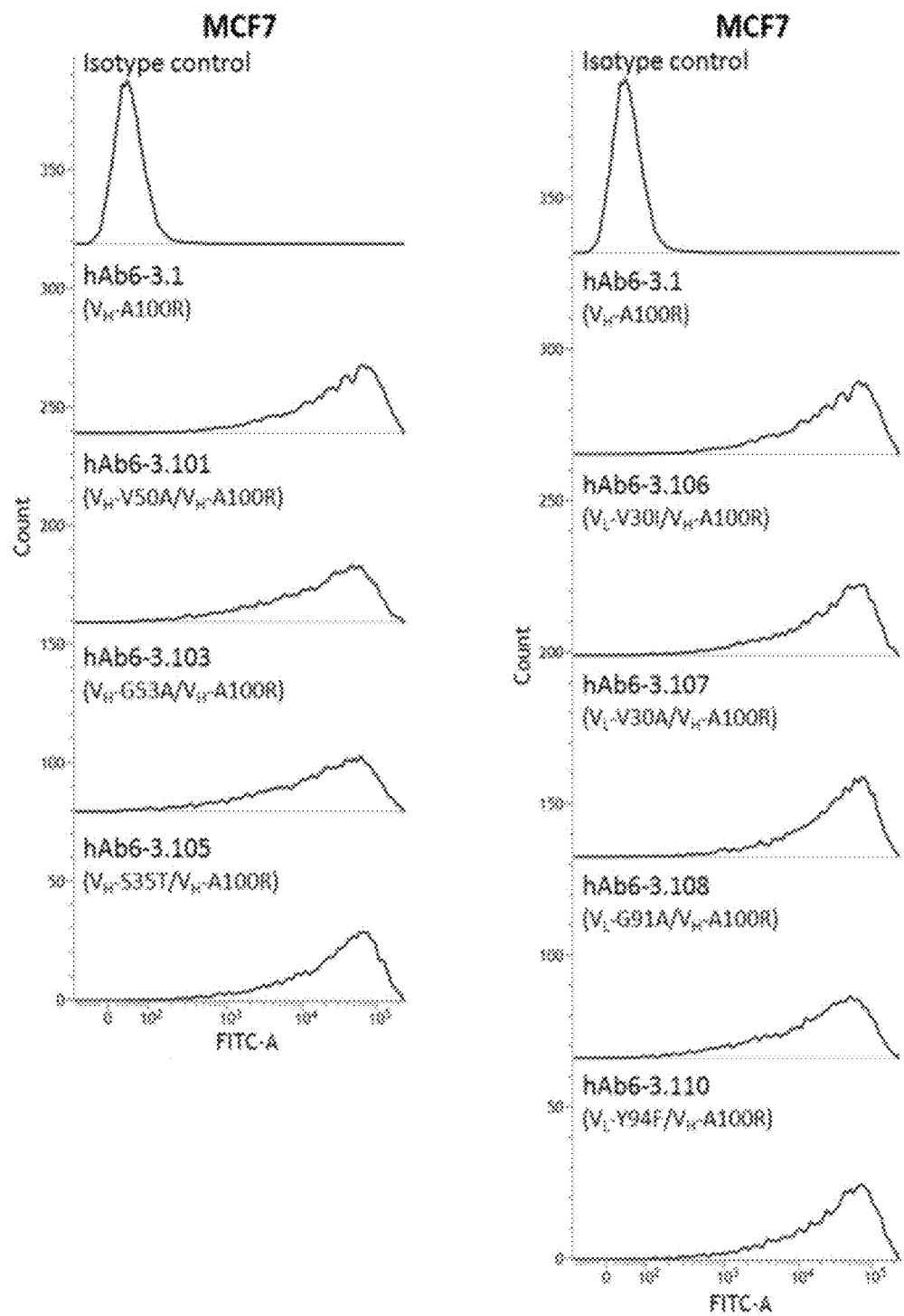

For flow cytometry analysis, $5 \times 10^5$ HPAC cells were incubated with chAb6 at the indicated concentration in FACS buffer (1% of FBS in PBS) for 30 minutes at 4° C. After wash by FACS buffer, cells were then incubated with PE-conjugated goat anti-human IgG antibody (1:250 diluted in FACS buffer, Jackson Immuno Research) for 30 minutes at 4° C. The binding of anti-SSEA4 antibody to cells was then analyzed by BD FACSVerse flow cytometer. (FIG. 10A-10B)

Example 5

Binding Specificity of Exemplary Anti-SSEA4 Antibody

Figure 7:
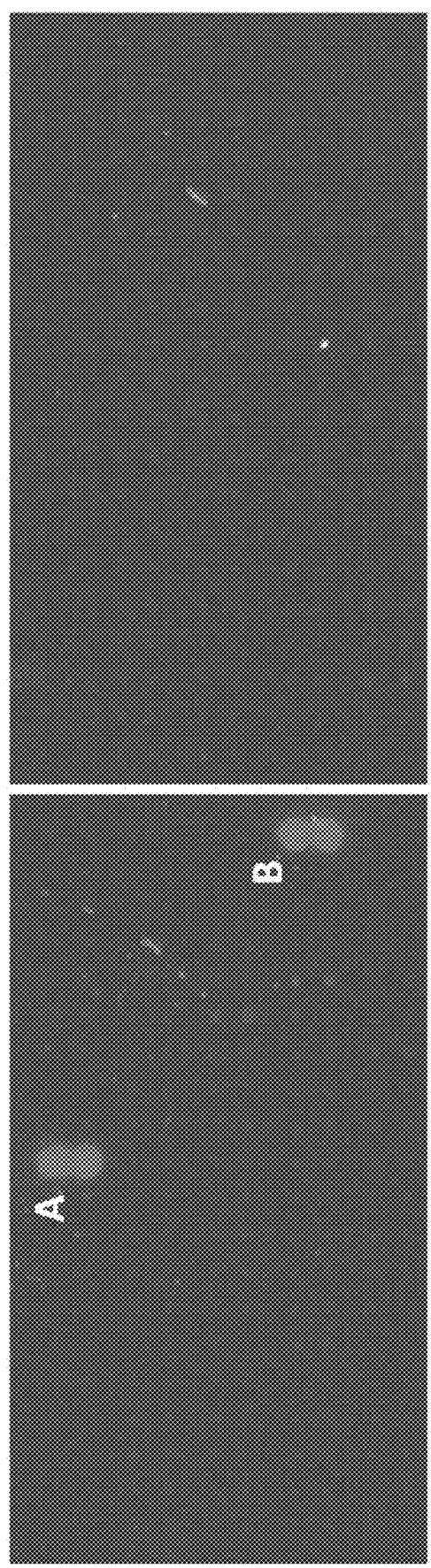
FIG. 7. The binding specificity of an exemplary chAb6 to SSEA4 by glycan array analysis. The binding septicity of chAb6 against various oligosaccharide was examined and the result indicated chAb6 binds to SSEA4 (spot A) and SSEA4 analog SSEA4 Gc (the Gc substituted sialic acid on amine group of SSEA4, spot B).
Figure 8A:
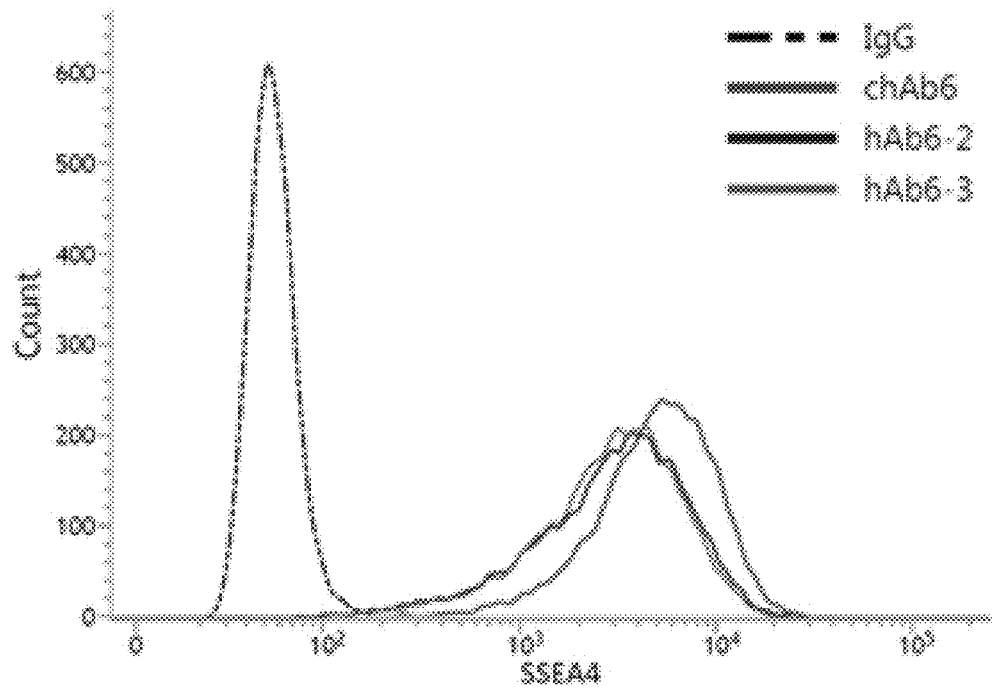
FIG. 8A-8B. The binding of chAb6 and humanized Ab6s to breast cancer cell lines. Characterization of chAb6, hAb6s (hAb6-2, hAb6-3) binding to (FIG. 8A) MDA-MB-231 and (FIG. 8B) MCF-7 by flow cytometry analysis.
Figure 8B:
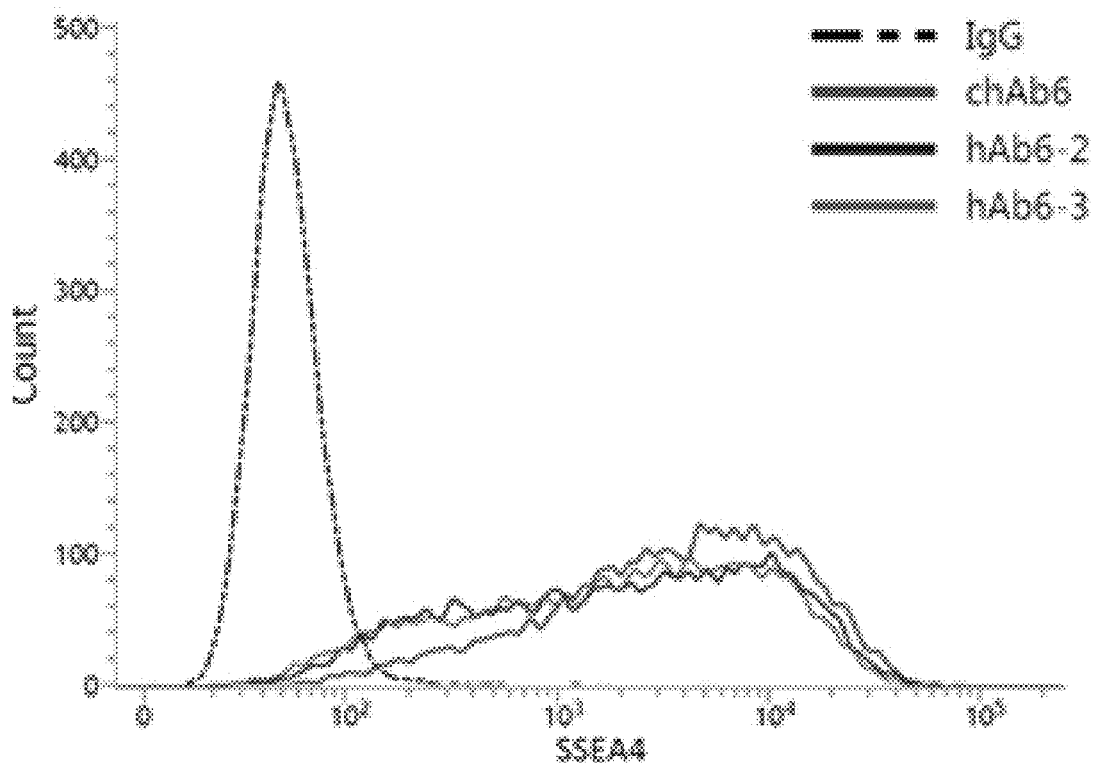
Figure 9A:
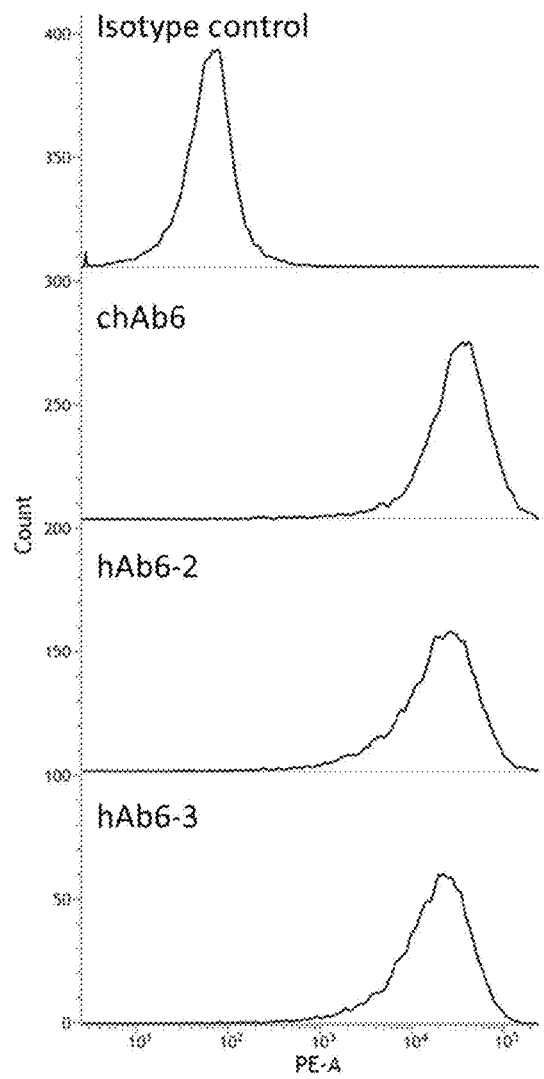
FIG. 9A-9B: The binding of exemplary chAb6 and humanized Ab6s to breast cancer cell lines. The binding of chAb6, hAb6-2 and hAb6-3 to (FIG. 9A) MDA-MB-231 and (FIG. 9B) MCF7 cells were examined by flow cytometry analysis. The antibody concentration used for staining was 1 microgram per milliliter.
Figure 9B:
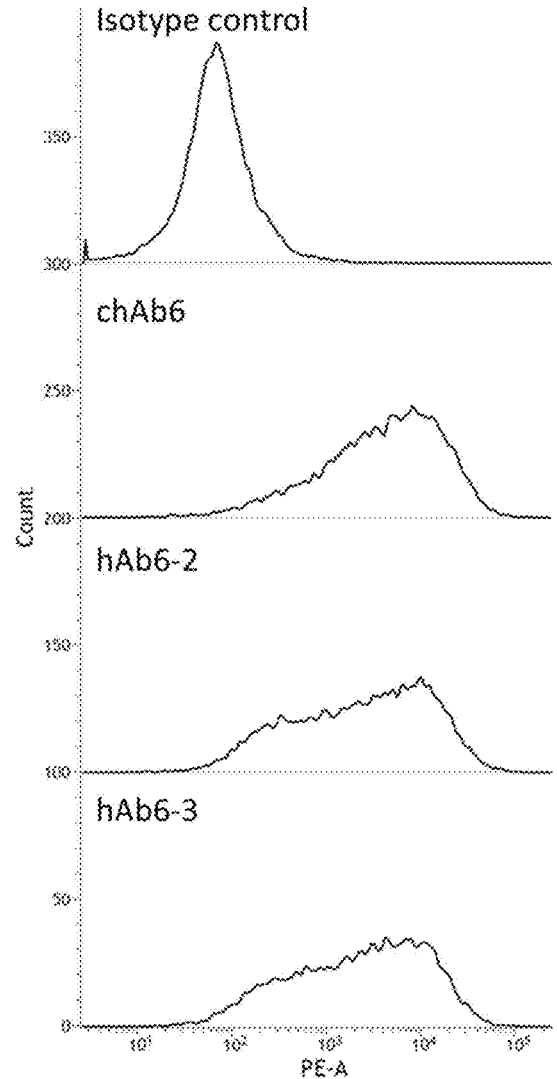

The binding specificity of exemplary anti-SSEA4 antibody was analyzed by using glycan microarray with 152 chemically synthesized glycans (FIG. 7). Briefly, the glycan microarray was incubated with the antibody at the indicated concentration at 37° C. for 1 hour. After washed by PBST (0.05% Tween 20 in PBS), the glycan microarray was then incubated with FITC-labeled goat anti-human IgG antibody for 1 hour at room temperature. Followed by another wash cycles, the glycan microarray was air-dried and scanned at 635 nm by a microarray fluorescence chip reader (4000B, Genepix). The data was then analyzed by GenePix Pro-6.0 (Axon Instruments).

Example 6

Figure 12:
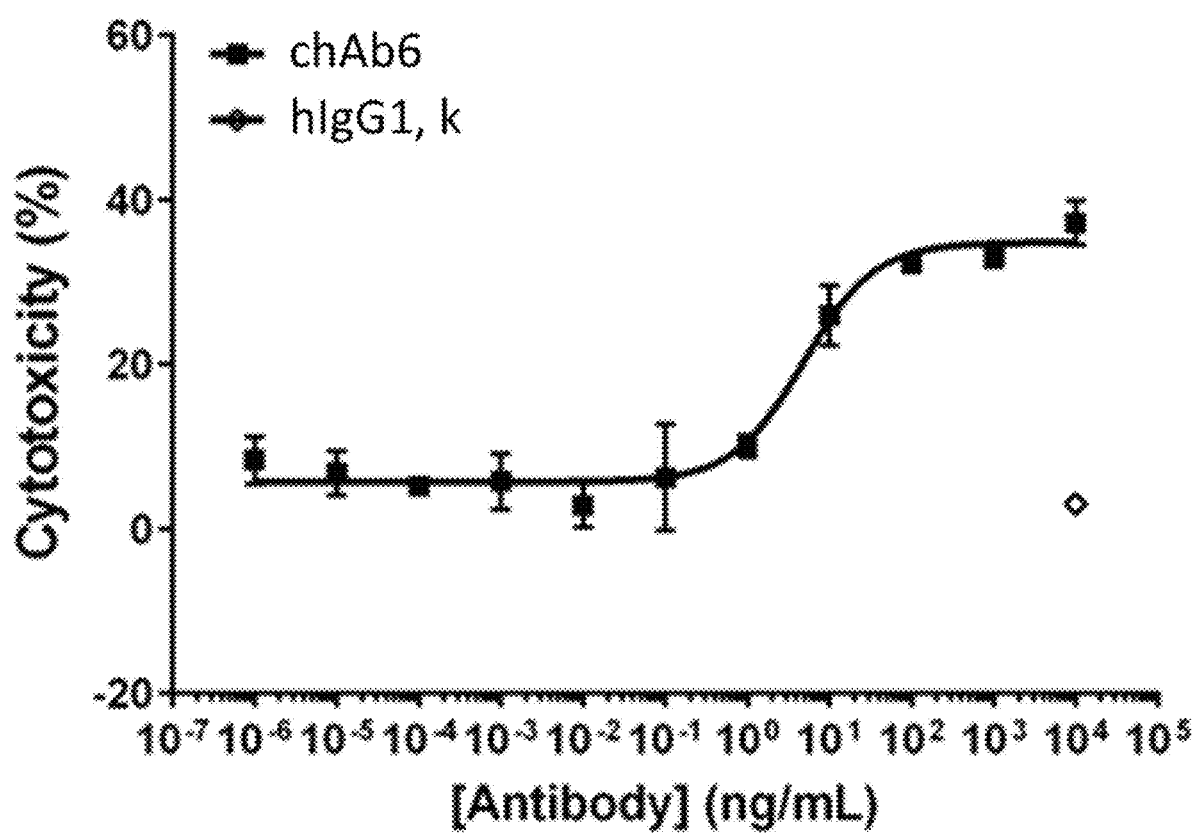

Antibody-Dependent Cellular Cytotoxicity (ADCC) Activity of chAb6 on a Pancreatic Tumor Cells Line HPAC The Calcein AM-labeled HPAC cells, a human pancreatic tumor cells line with high SSEA4 expression, were mixed with PBMC first, and the anti-SSEA4 antibody was then added at the indicated concentration and allowed to incubate for 4 hrs at 37° C. After incubation, the culture supernatant was collected and detected at ex.485 nm/em.535 nm, and the percentage of cell cytotoxicity was calculated as: (experimental value−spontaneous lysis)/(maximum lysis−spontaneous lysis)×100. (FIG. 12)

Example 7

Figure 15A:
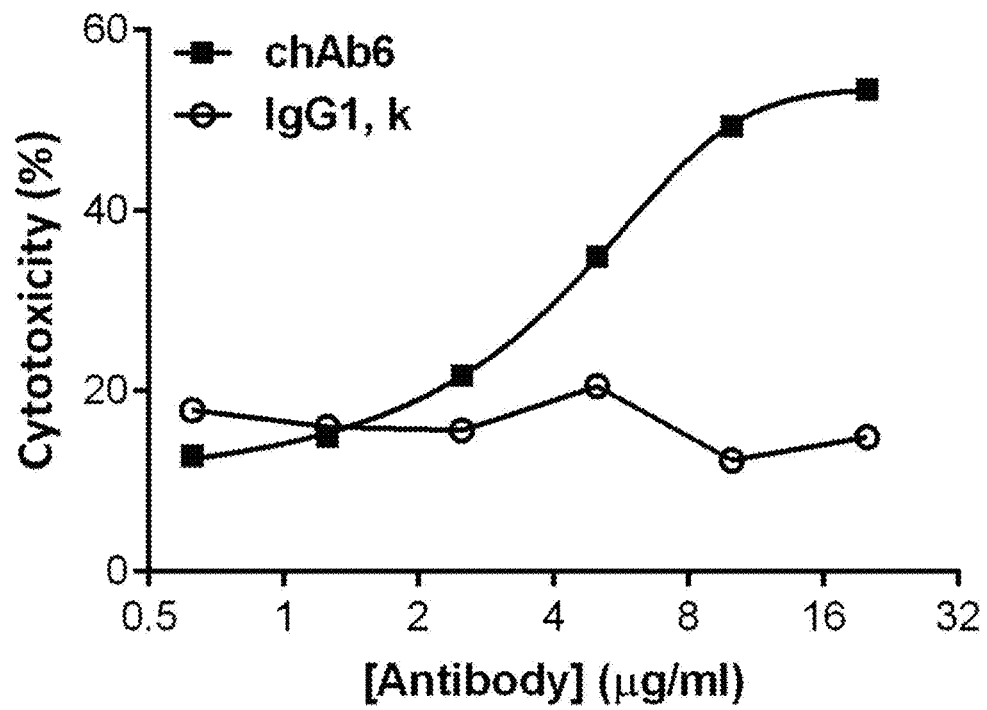
FIG. 15A-15B. 15A: Demonstration of the CDC activity of an exemplary chAb6 on HPAC cells. Representative chAb6 induces CDC to kill HPAC cells in a dose-dependent manner. The $EC_{50}$ is 3 μg/mL. Human IgG1, kappa (hIgG1, k) is used as a negative control in this study. 15B: Demonstration of the CDC activity of exemplary humanized Ab6s on breast cancer cell line. The exemplary humanized anti-SSEA4 antibodies hAb6-3 and hAb6-3.1 induced CDC to kill MCF7 cells in a dose-dependent manner. The $EC_{50}$ are about 4.4 and about 2.6 μg/mL for hAb6-3 and hAb6-3.1, respectively.

Complement-Dependent Cytotoxicity (CDC) Activity of chAb6 on a Pancreatic Tumor Cells Line HPAC For CDC assay, $2 \times 10^5$ HPAC cells were incubated with 15% of human serum and anti-SSEA4 antibody at the indicated concentration at 37° C. for 1 hour. After incubation, the dead cells were stained by propidium iodide (PI) for 5 minutes at room temperature, and then counted and analyzed by BD FACSVerse flow cytometer (FIG. 15A).

Example 8

Figure 16A:
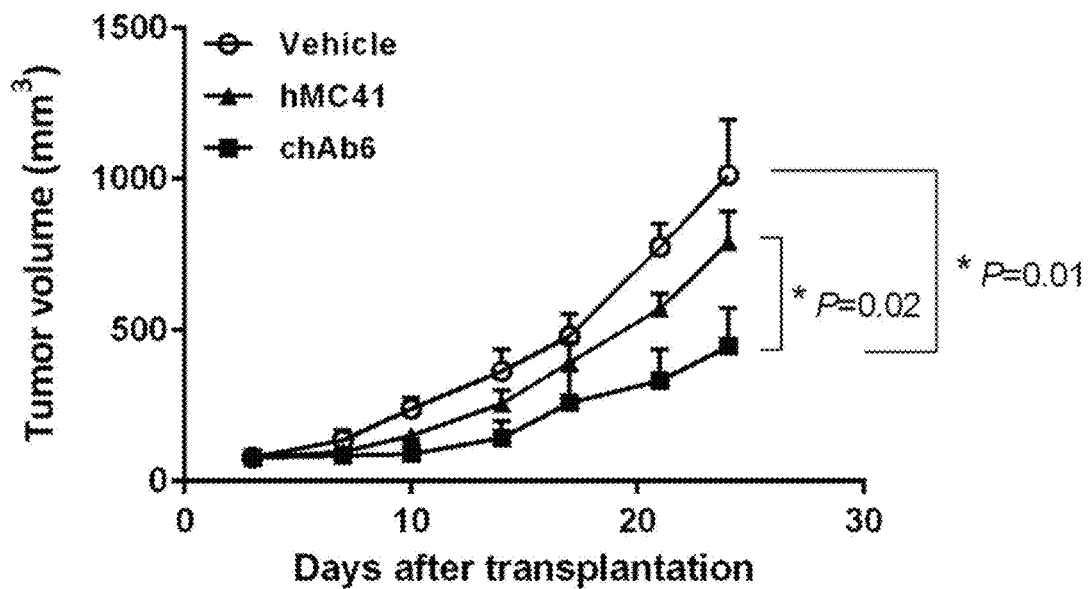
FIG. 16A-16B. Demonstration of in vivo anti-tumor efficacy of representative anti-SSEA4 antibodies in HPAC xenograft model. Comparing to vehicle control group, the growth of tumor is significantly suppressed in mice with anti-SSEA4 antibody treatment. Moreover, as shown in figure, the average tumor volume (FIG. 16A) and weight (FIG. 16B) in mice treated with chAb6 are significantly smaller than those treated with hMC41, demonstrating that this exemplary chAb6 has an unexpectedly surprising in vivo anti-tumor activity.
Figure 16B:
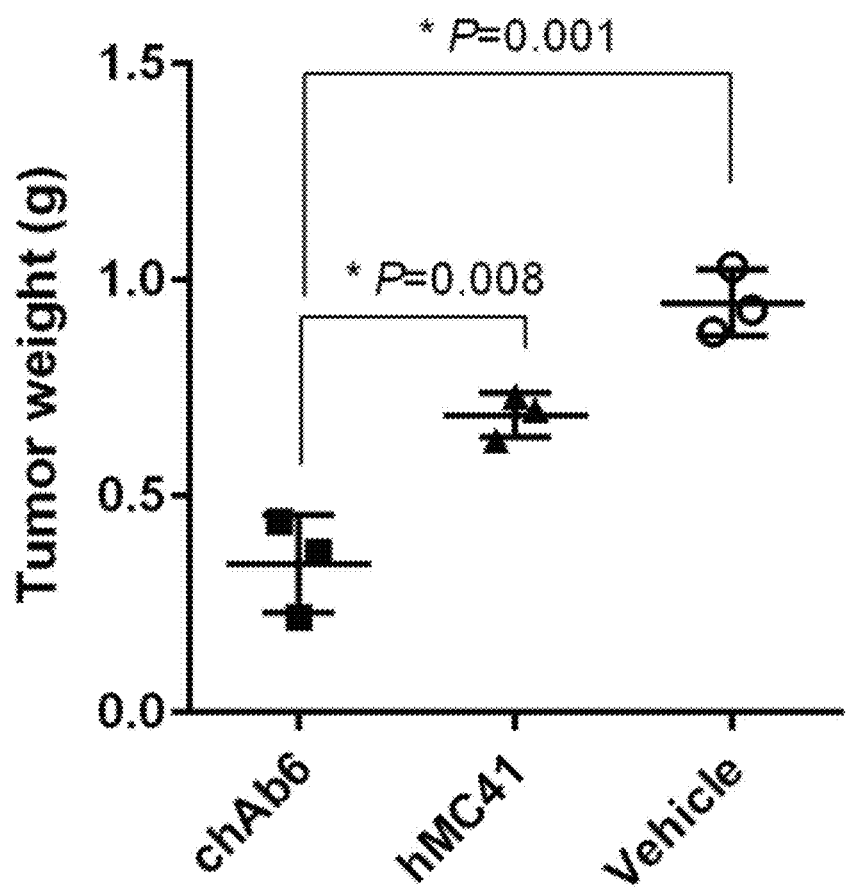

In Vivo Anti-Tumor Efficacy of Exemplary Anti-SSEA4 Antibodies in HPAC Xenograft Model To evaluate the anti-tumor efficacy of exemplary anti-SSEA4 antibodies in vivo, male CB17.SCID mice, aged 8 weeks old (Biolasco, Taiwan), were subcutaneously injected with $5\times10^6$ HPAC cells. While the tumor formed and the volume reached 50 to 100 $mm^3$, vehicle or exemplary anti-SSEA4 antibodies (20 mpk) was intravenously injected into the tail vein twice per week. Tumor growth was monitored twice weekly by measuring the perpendicular tumor diameters, length (L) and width (W), with a vernier caliper. The volume of tumor (V) was calculated by the formula $V=LW^2/2$. On day 24 (24 days after transplantation), the mice were sacrificed to measure the tumor weight. All the results were showed as mean±S.D. (n=3 for each group), and Student's t test was used for statistical analysis. (FIG. 16A-16B)

Example 9

Detecting SSEA4 Expressed in Tumor Tissue by Using Exemplary chAb6

Figure 19:
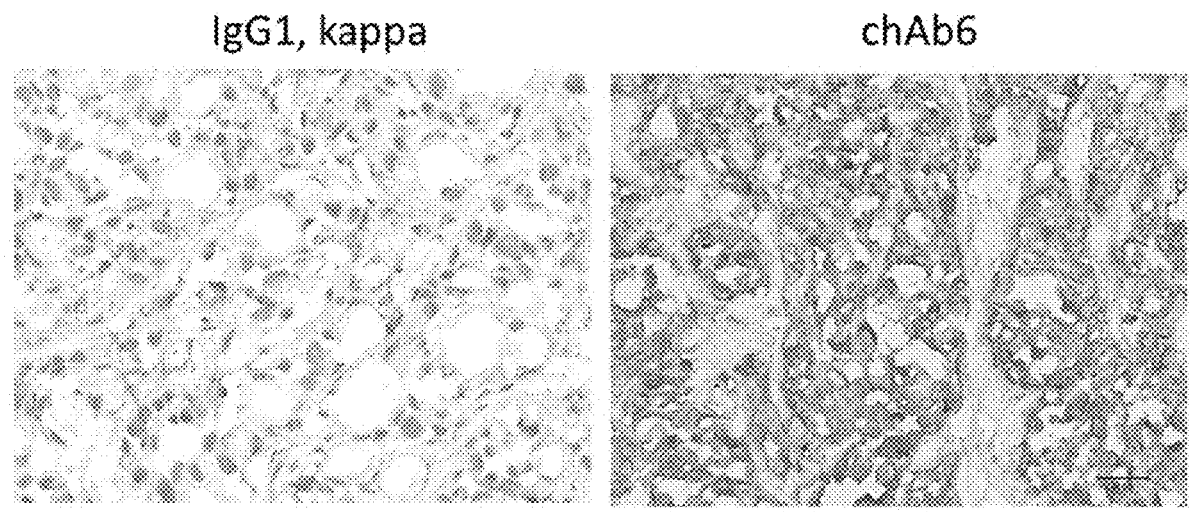
FIG. 19 Demonstration of diagnostic utility: Detection of SSEA4 expression in tumor tissue using exemplary chAb6.

Immunohistochemistry (IHC) was employed to detect the presence of SSEA4 in tumor tissue (FIG. 19). Briefly, the frozen sections of HPAC xenograft tumor were fixed with 10% neutral buffered formalin (Sigma-Aldrich) at room temperature for 10 minutes first, and the endogenous peroxidase activity was quenched by immersing sections in 0.3% hydrogen peroxide/0.1% sodium azide in $ddH_2O$ for 15 min at RT. After wash cycles (PBS, 3 times, 5 minutes for each), the sections were incubated with 2 µg/mL of FITC-labeled chAb6 or human IgG1, kappa at 4° C. overnight. After an overnight incubation, the sections were then washed and incubated with HRP-labeled goat anti-FITC antibody (1:200, KPL) for 1 hour at room temperature. After another wash cycles, DAB substrate (Vector laboratories) was used for color development, and hematoxylin (Sigma-Aldrich) was used for counter staining.

Example 10

Treatment of Disorders

Subjects at risk for or afflicted with cancer may be in need of immune response augmentation would benefit from treatment with a SSEA4 antibody of the present invention in a soluble form. Most commonly, antibodies are administered in an outpatient setting by weekly administration at about 0.1-10 mg/kg dose by slow intravenous (IV) infusion. The appropriate therapeutically effective dose of an antagonist is selected by a treating clinician and would range approximately from 1 µg/kg to 20 mg/kg, from 1 µg/kg to 10 mg/kg, from 1 µg/kg to 1 mg/kg, from 10 µg/kg to 1 mg/kg, from 10 µg/kg to 100 µg/kg, from 100 µg to 1 mg/kg, and from 500 µg/kg to 5 mg/kg. It is anticipated that SSEA4 antibodies of the invention would be administered with a frequency of one per month or less. Treatment duration could range between one month and several years.

To test the clinical efficacy of antibodies in humans, individuals with cancer are identified and randomized to a treatment group. Treatment groups include a placebo group and one to three groups treated with a SSEA4 antibody (different doses). Individuals are followed prospectively for one to three years. It is anticipated that individuals receiving treatment would exhibit an improvement.

Example 11

Figure 5:
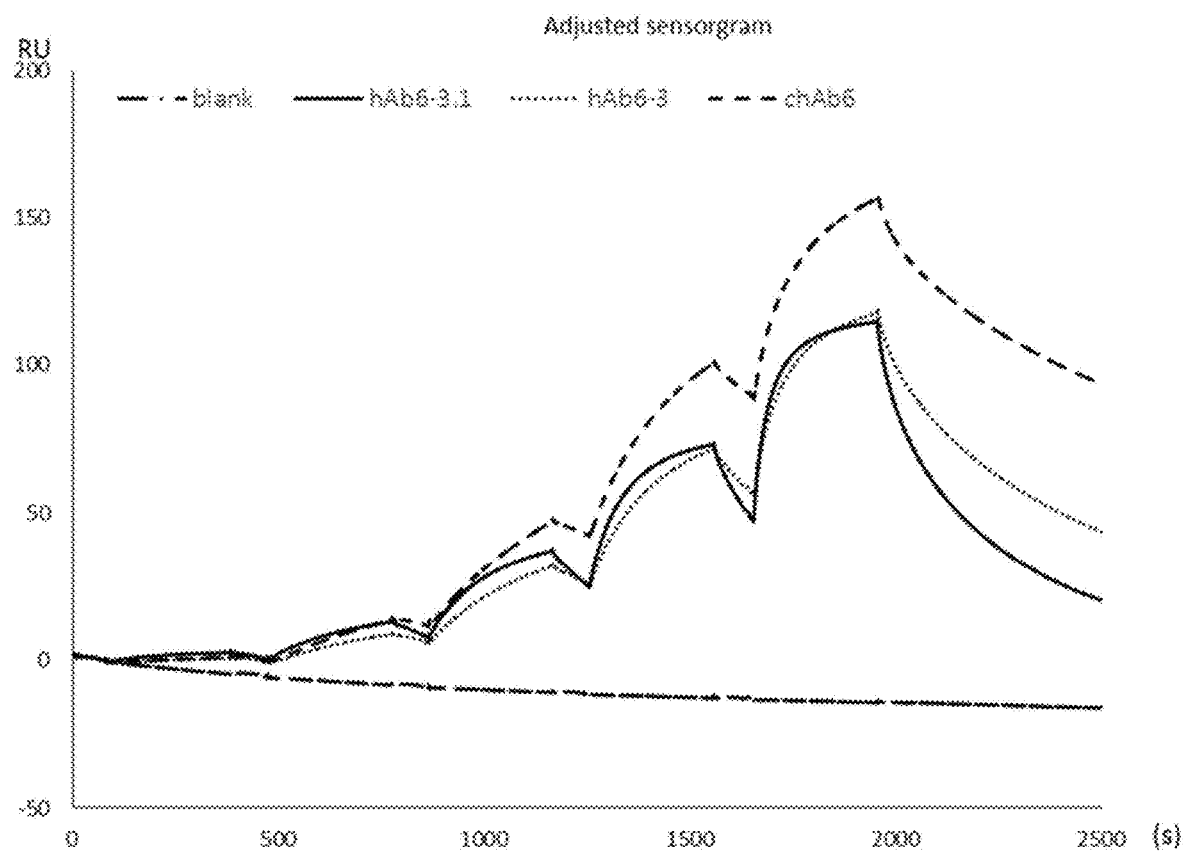
FIG. 5. Kinetic binding assay of exemplary chimeric and humanized Ab6 by surface plasmon resonance. The antigen binding affinity of hAb6-3.1, hAb6-3 and chAb6 were determined using Biacore system. The calculated Kd values for hAb6-3.1, hAb6-3 and chAb6 are 23.1, 17.8 and 10.11 nM, respectively.
Figure 6A:
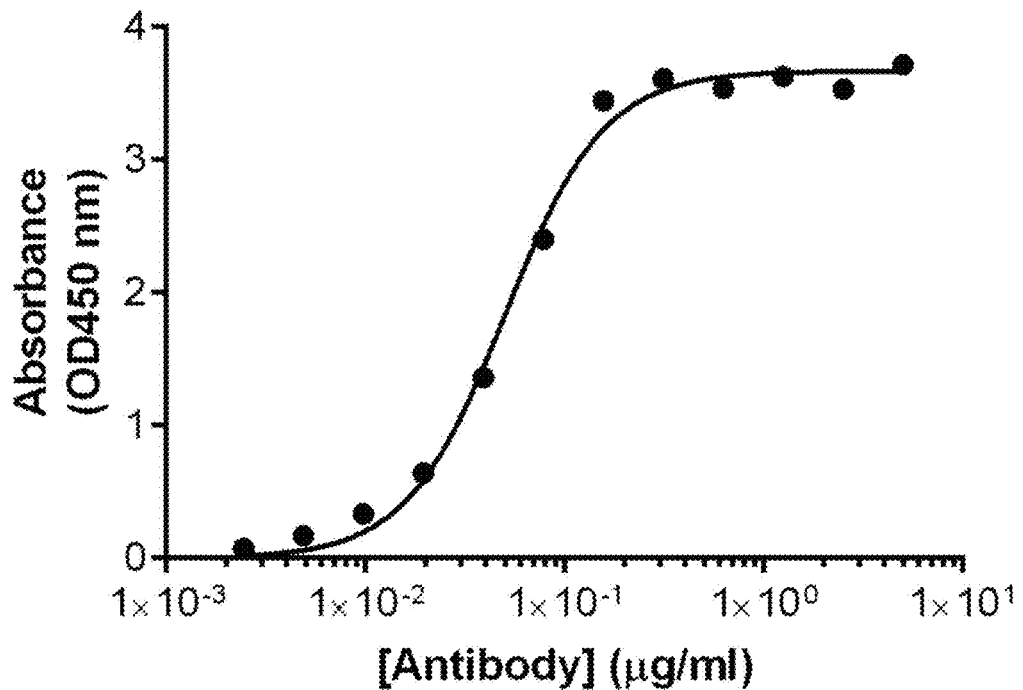
FIG. 6A. Determination of the binding affinity of one exemplary chAb6 to SSEA4 by ELISA. The exemplary chimeric Ab6 (chAb6) binds to SSEA4 in a dose-dependent manner. The binding $EC_{50}$ of chAb6 to SSEA4 is about 50 ng/mL.
Figure 6B:
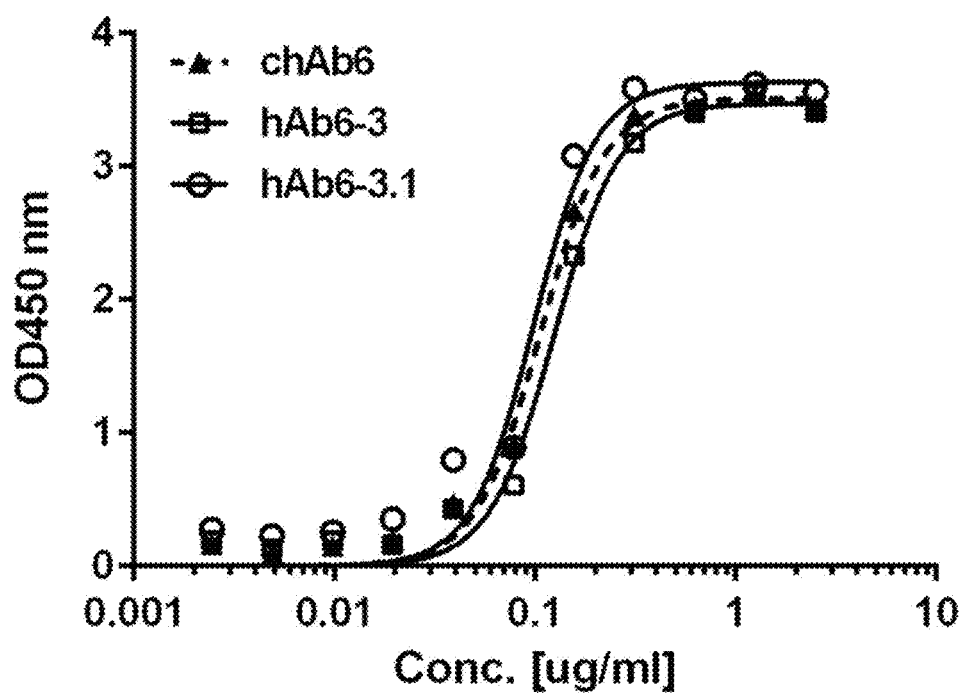
FIG. 6B. Determination of the binding affinity of other exemplary chimeric and humanized Ab6s to SSEA4 by ELISA. The exemplary chimeric and humanized Ab6s bound to SSEA4 in a dose-dependent manner. The binding $EC_{50}$ of chAb6, hAb6-3 and hAb6-3.1 to SSEA4 are about 106, 125 and 98 ng/mL, respectively.
Figure 6C:
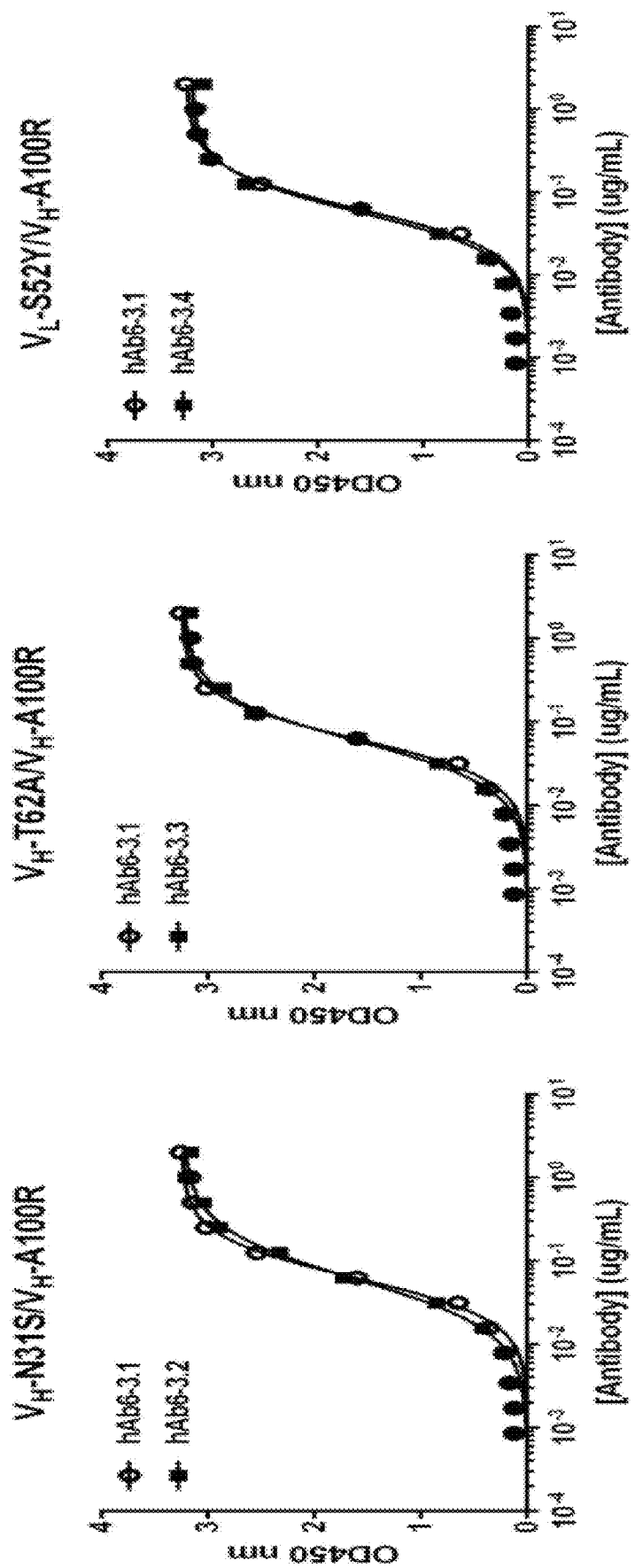
FIG. 6C-6D.
Figure 6D:
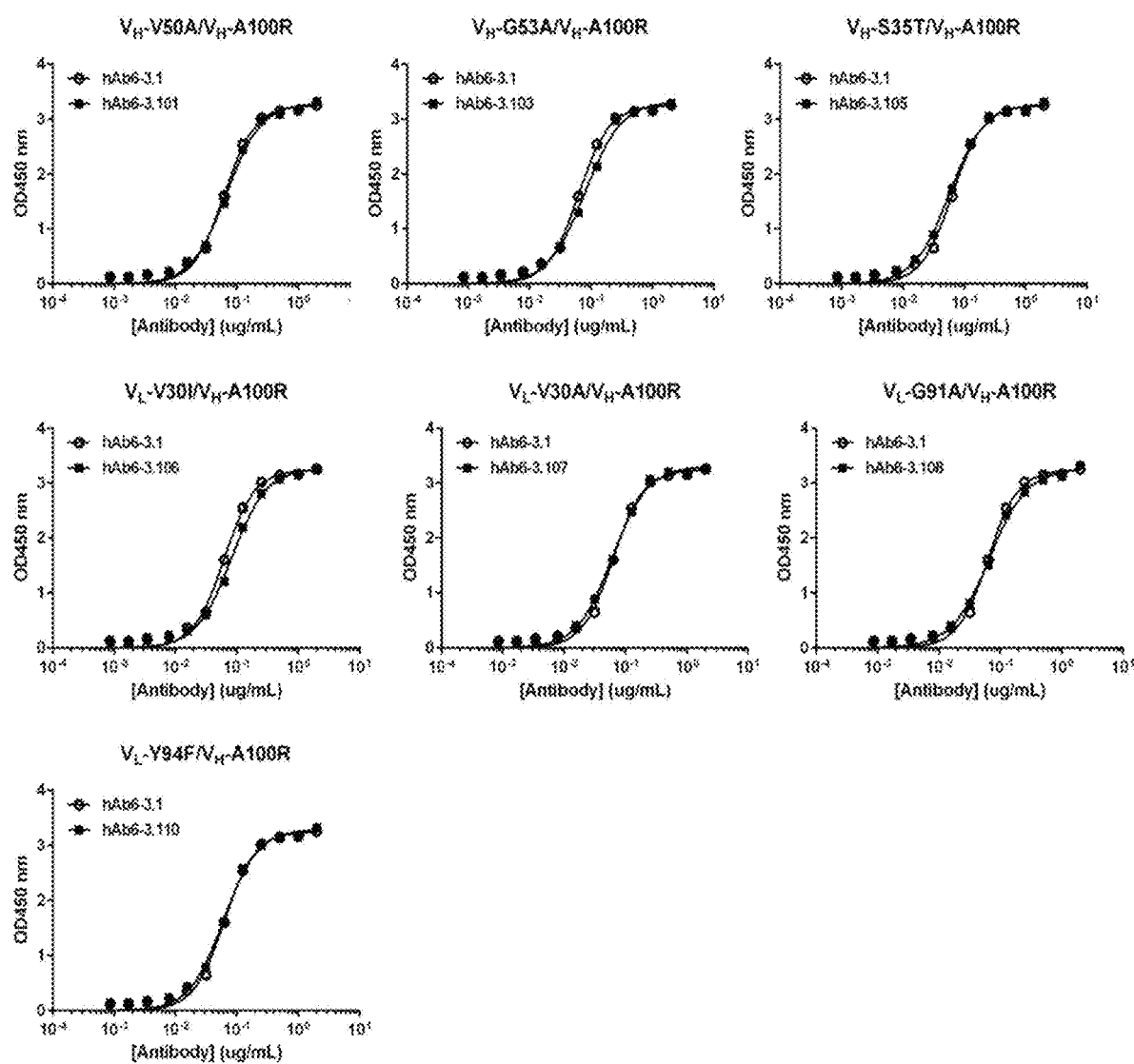

Kinetic Binding Assays of Exemplary Anti-SSEA4 Antibodies by Surface Plasmon Resonance The kinetic binding of exemplary anti-SSEA4 antibodies were analyzed by surface plasmon resonance (SPR) using Biacore T200 system. Firstly, the biotinylated SSEA4 was immobilized on Sensor Chip SA. The representative anti-SSEA4 antibodies hAb6-3.1, hAb6-3 and chAb6 were serially diluted in running buffer (lx PBS buffer containing 0.05% Tween-20, pH7.4) to concentrations of 100, 33.3, 11.1, 3.7, 1.2 nM, and then injected for 5 min at 30 uL/min using single-cycle mode. The analysis of parameters was performed by BIAevaluation software. (FIG. 5)

Example 12

Binding of Exemplary Anti-SSEA4 Antibodies to Cell by Flow Cytometry Analysis

For flow cytometry analysis, $3\times10^5$ cancer cells, such as breast cancer cell line MDA-MB-231, MCF7, were incubated with exemplary anti-SSEA4 antibodies at the indicated concentration in FACS buffer (1% of FBS in PBS) for 30 minutes at 4° C. After wash by FACS buffer, cells were then incubated with PE- or Alexa Fluor488-conjugated goat anti-human IgG antibody (1:250 to 1:400 diluted in FACS buffer, Jackson Immuno Research) for 30 minutes at 4° C. The binding of anti-SSEA4 antibody to cells was then analyzed by BD FACSVerse flow cytometer. (see FIGS. 9A-9B and FIGS. 11A-11F)

Example 13

Figure 13:
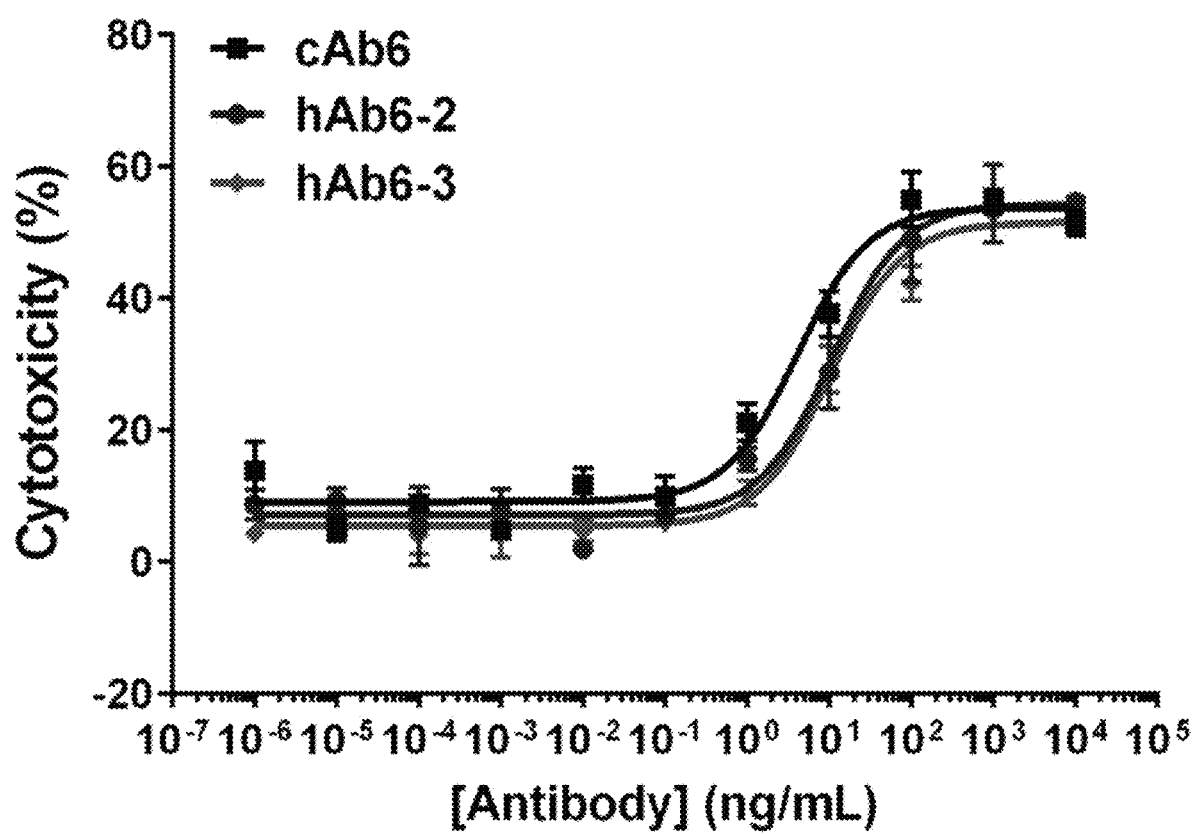
FIG. 13. The ADCC activity of exemplary chAb6 and humanized Ab6s on MDA-MB-231 cells. The exemplary chAb6, hAb6s mediate ADCC to kill MDA-MB-231 cells in a dose-dependent manner. The $EC_{50}$ are about 5 ng/mL and 10 ng/mL for chAb6 and hAb6s, respectively.
Figure 14A:
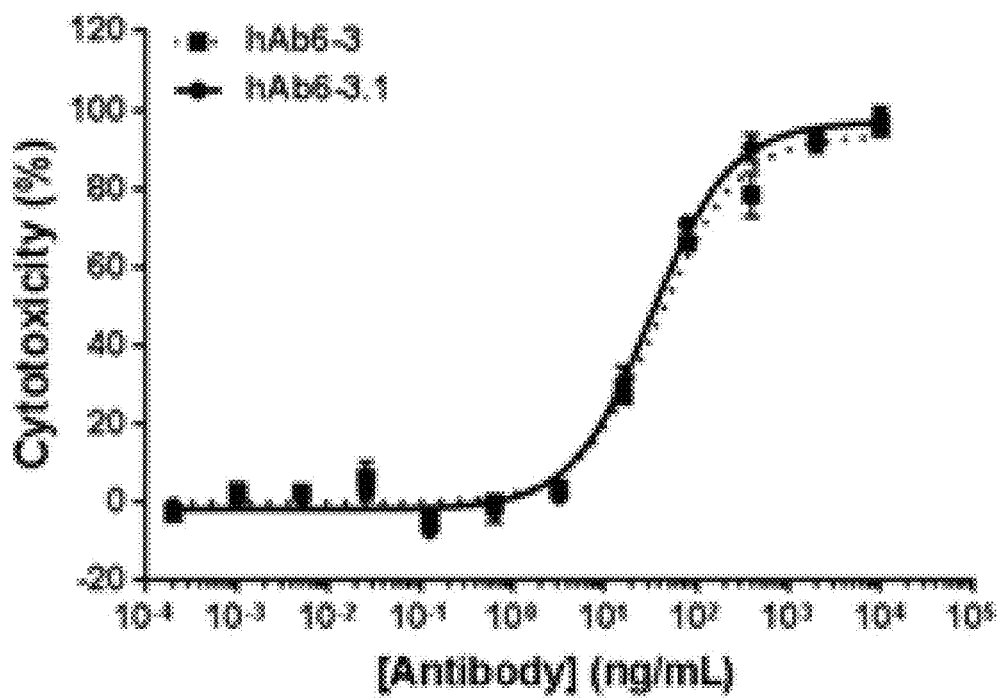
FIG. 14A-14B: The ADCC activity of exemplary humanized Ab6s on breast cancer cell lines. Both exemplary hAb6-3 and exemplary hAb6-3.1 mediated ADCC to kill (FIG. 14A) MDA-MB-231 and (FIG. 14B) MCF7 cells in a dose-dependent manner. In this study, the $EC_{50}$ for hAb6-3-mediated ADCC to kill MDA-MB-231 and MCF7 are 39.2 and 39.5 ng/mL, respectively. For hAb6-3.1-mediated ADCC to kill MDA-MB-231 and MCF7 are 32.6 and 38.9 ng/mL, respectively.
Figure 14B:
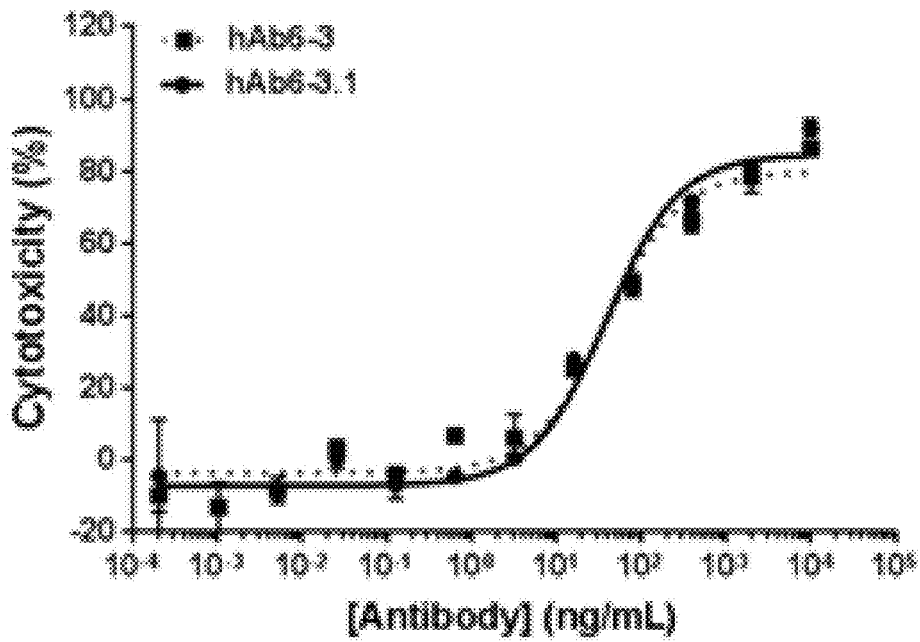

Antibody-Dependent Cellular Cytotoxicity (ADCC) Activity of Exemplary Chimeric and Humanized Ab6s on Breast and Pancreatic Cancer Cell Lines The MDA-MB-231, MCF7 and HPAC cells were labeled with 20 uM of Calcein AM for 30 min. After washing, the Calcein-AM labeled target cells ($1\times10^4$ cells/well) were co-incubated with fresh isolated human PBMC ($2.5\times10^5$ cells/well, E/T ratio=25/1), and treated with or without serially diluted anti-SSEA4 antibodies for 4 hr. The release of Calcein-AM was detected by M5 ELISA reader (ex. 485, em. 520) and used for evaluation of relative cytotoxicity. (FIG. 13, FIG. 14A-14B)

Example 14

Complement-Dependent Cytotoxicity (CDC) Activity of Exemplary Chimeric and Humanized Ab6s on Breast and Pancreatic Cancer Cell Lines For HPAC, $2\times10^5$ cells were incubated with 15% of human serum and anti-SSEA4 antibody at the indicated concentration at 37° C. for 1 hour. After incubation, the dead cells were stained by propidium iodide (PI) for 5 minutes at room temperature, and then counted and analyzed by BD FACSVerse flow cytometer. (FIG. 15A)

Figure 15B:
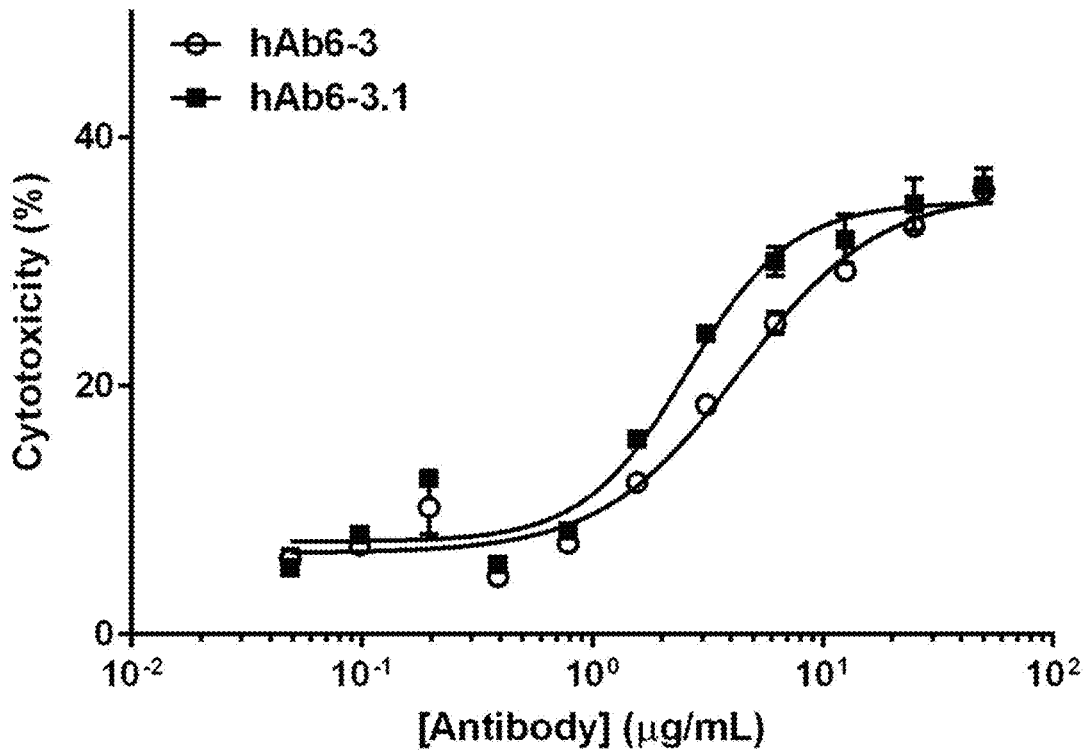

For MCF7, cells were labeled with 20 uM of Calcein AM for 30 min firstly. After washing, the Calcein-AM labeled target cells ($1 \times 10^4$ cells per assay) were co-incubated with 10% of human serum, and treated with or without anti-SSEA4 antibody at the indicated concentration at 37° C. for 2 hour. The release of Calcein-AM was detected by M5 ELISA reader (ex. 485, em. 520) and used for evaluation of relative cytotoxicity. (FIG. 15B)

Example 15

Figure 17:
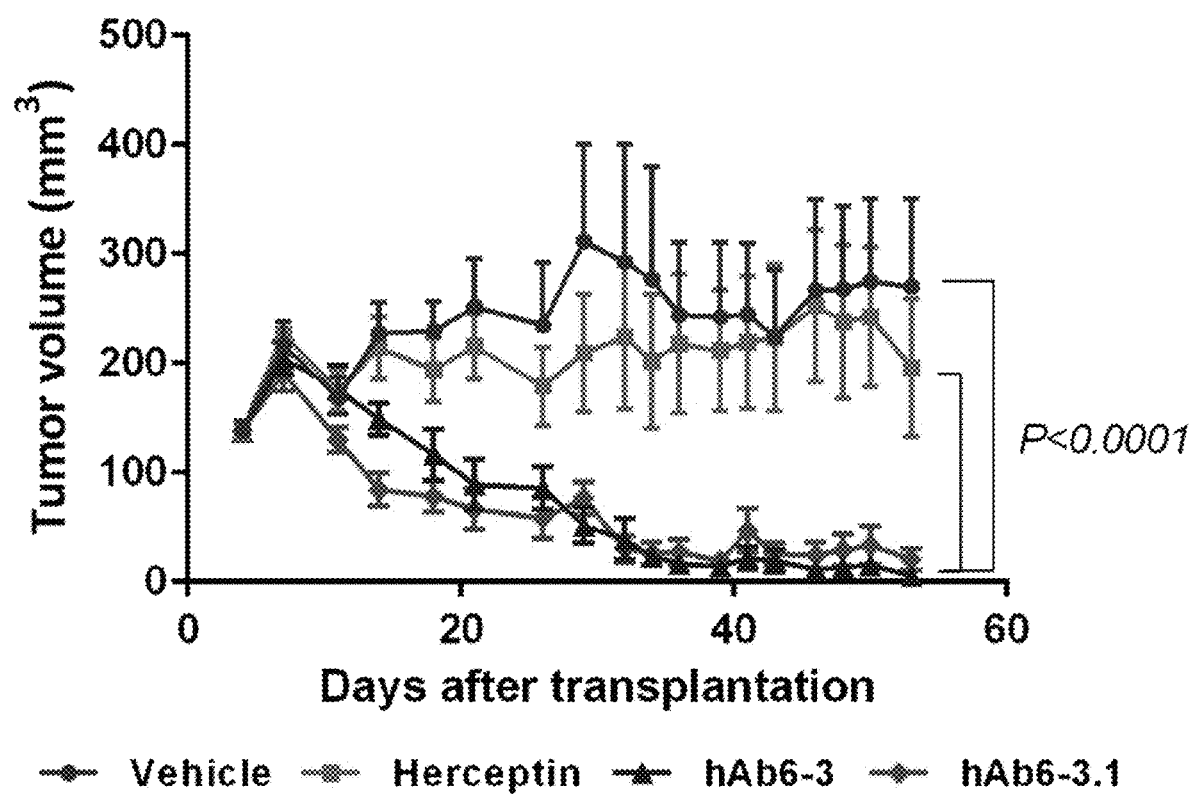
FIG. 17. Demonstration of in vivo anti-tumor efficacy of exemplary humanized Ab6s in MDA-MB-231 orthotopic model. The in vivo tumor growth was significantly suppressed by treating tumor-bearing mice with exemplary anti-SSEA4 antibodies hAb6-3 and hAb6-3.1, as comparing with the control groups (vehicle and Herceptin). Herceptin was used as a control antibody in this study.

In vivo Anti-Tumor Efficacy Of Anti-SSEA4 Antibodies in MDA-MB-231 Xenograft Model To evaluate the anti-tumor efficacy of anti-SSEA4 antibodies in vivo, female Balb/c nude mice, aged 8 weeks old (NLAC, Taiwan), were orthotopically injected with $5 \times 10^6$ MDA-MB-231 cells. While the tumor formed and the volume reached 100 to 150 mm$^3$, vehicle, Herceptin or anti-SSEA4 antibodies (20 mpk) was intravenously injected into the tail vein twice per week. Tumor growth was monitored twice weekly by measuring the perpendicular tumor diameters, length (L) and width (W), with a vernier caliper. The volume of tumor (V) was calculated by the formula $V=LW^2/2$. All the results were showed as mean±SEM (n=8 for each group), and Student's t test was used for statistical analysis. (FIG. 17)

Example 16

Figure 18:
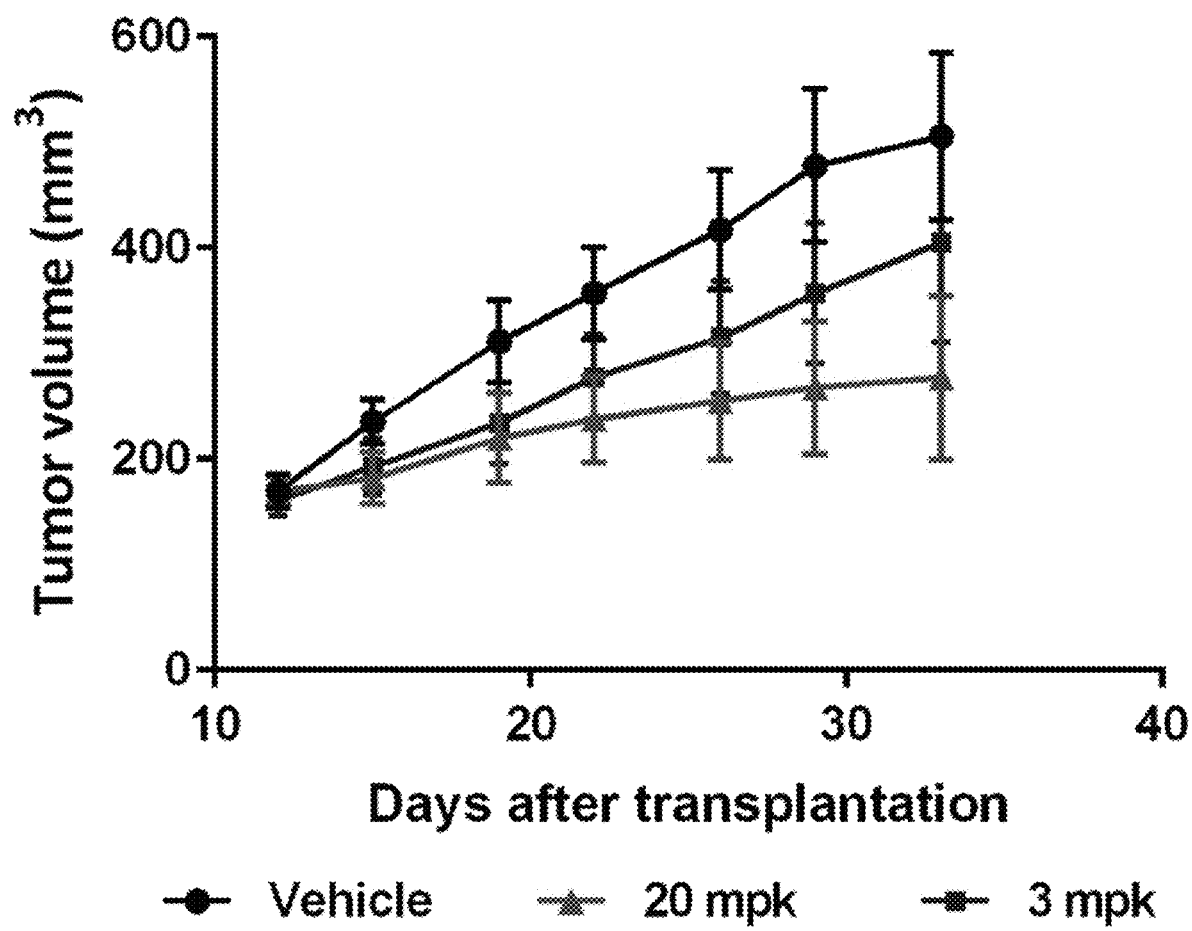
FIG. 18: Demonstration of in vivo anti-tumor efficacy of an exemplary humanized Ab6 MCF7 orthotopic model. As comparing with vehicle control treatment, the growth of tumor was significantly suppressed in a dose-dependent manner under the treatment of hAb6-3.1.

In Vivo Anti-Tumor Efficacy of Anti-SSEA4 Antibodies in MCF7 Xenograft Model To establish MCF7 xenograft model, female Balb/c nude mice (aged 8 weeks old, purchased from Biolasco, Taiwan) were subcutaneously implanted with 17-beta-estradiol pellet at Day 1. Five million MCF7 cells were mixed with Matrigel, and then orthotopically injected into mammary fat pad. While the tumor formed and the volume reached 150 to 200 mm$^3$, vehicle or hAb6-3.1 (at the indicated dose) was intravenously injected into the tail vein twice per week. Tumor growth was monitored twice weekly by measuring the perpendicular tumor diameters, length (L) and width (W), with a vernier caliper. The volume of tumor (V) was calculated by the formula $V=LW^2/2$. All the results were showed as mean±SEM. (n=7 for each group), and Student's t test was used for statistical analysis. (FIG. 18)

Example 17

Exemplary Methodology for the Development of Glyco-Engineered hAb6-3.1

Production of Glyco-Engineered hAb6-3.1
The glycans of exemplary anti-SSEA4 antibody hAb6-3.1 was hydrolyzed to mono-GlcNAc form via co-incubating with endo-beta-N-acetylglucosaminidase and fucosidase. The glyco-engineered antibody was produced by transglycosylating the universal glycan onto the mono-GlcNAc in the presence of endo-beta-N-acetylglucosaminidase mutant, followed by the purification of rProtein A chromatography. Characterization of glyco-engineered Ab6-3.1 was performed by SDS-PAGE and flow cytometry analysis (FIGS. 20 and 21, respectively).

In Vitro Functional Assays of Glyco-Engineered hAb6-3.1
Glycoengineering was shown to improve the binding affinity of antibody to Fc gamma receptors expressed on immune cells, which contributes the protective function of the immune system. We demonstrated the Fc gamma receptor IIIA binding and ADCC function (antibody-dependent cell-mediated cytotoxicity) of glyco-engineered hAb6-3.1 as below.

Fc Gamma Receptor IIIA Binding
Fc gamma receptor IIIA was coated on the ELISA plate, and incubated with native and glyco-engineered antibody at the indicated concentration. The binding activity was then determined by using HRP-conjugated anti-Human IgG H+L and TMB substrate. (FIG. 22)

ADCC Assay
The Calcein AM-labeled MDA-MB-231 cells, a human triple-negative breast cancer cell line with high SSEA-4 expression, were mixed with PBMC first, and the native or glyco-engineered anti-SSEA-4 antibodies were then added at the indicated concentration and allowed to incubate for 4 hours at 37° C. After incubation, the culture supernatant was collected and detected at ex.485/em.535, and the percentage of cell cytotoxicity was calculated as: (experimental value−spontaneous lysis)/(maximum lysis−spontaneous lysis)×100. (FIG. 23)

Glycoengineering of anti-SSEA-4 antibody significantly enhanced the binding of antibody to Fc gamma receptor IIIA, resulting in the improved antibody-dependent cellular cytotoxicity (ADCC) activity as compared with the native antibody.

Example 18

Representative Methodology for the Development/Formation of Antibody-Drug Conjugation Complex Several chemical approaches were available for the antibody-drug conjugation, such as thiol-melimide formation on the lysine and cysteine residues (Lewis Phillips et al., 2008), selenol-maleimide formation on the selenocysteine residues (Hofer et al., 2009), oxmie ligation to the modified Fc glycans (Zhou et al., 2014), Click chemistry (Axup et al., 2012), Hydrazino-iso-Pictet-Spengler ligation to fomylglycine residue (Drake et al., 2014). We adapted the use of a representative oxime ligation onto the modified Fc glycan as our exemplary ADC formation approach. Oxime ligation between the modified glycan on the antibody and payload compound A1 (cytotoxic drug MMAE with a alkoxyamine-cleavable linker, M.W.: 1348.7265) was carried out in the present of antibody (8 mg/mL) and A01 (3 mM) in 100 mM acetate buffer pH 4.5 at 25° C. The reaction was incubated for 48 hours and the product was purified by rProtein A, Capto S and Capto Q column sequentially. The result of hAb6-3.1-A01 complex formation was analyzed by SDS-PAGE (FIG. 24A-B).

Example 19

The Binding Ability of hAb6-3.1-A01 to SSEA4-Expressing Cells by Flow Cytometry SSEA4-expressing cell line MCF7 and SKOV3 were washed with PBS and $1 \times 10^5$ of cells were incubated with 10 ug/mL of hAb6-3.1 or hAb6-3.1-A01 in FACS buffer (PBS containing 2% FBS and 0.1% NaN$_3$) on ice for 1 hr. After washing with PBS, the cells were stained with Alexa-Fluor 488 labeled anti-human IgG antibody and incubated on ice for 0.5 hr. The signals for cell binding of antibodies were detected by flow cytometry (Figure XX11AB). The result indicated the binding property of hAb6-3.1-A01 to SSEA4-expressing cell is similar with parental antibody hAb6-3.1 (FIG. 25A-B).

Example 20

In Vitro Cell Cytotoxicity Assay in Breast Cancer Cell Line

MCF7, a SSEA4-expressing breast cancer cell line, were seeded in 96-well white plate (1×10$^3$ cells/well) and incubated at 37° C. overnight. The cells were treated with serially diluted hAb6-3.1 or hAb6-3.1-A01 and incubated for further 5 days. After treatment, the culture medium was removed and the cells were treated with CellTiter Glo reagent (Promega). The luminescence signals were detected by ELISA reader (M5) after incubation for 10 mins, and the cell viability was calculated (the signals of untreated cells were set as 100% of viability).

As shown in FIG. 26, hAb6-3.1-A01 performed cytotoxicity in a dose dependent manner. The ADC exhibits a sigmoid curve, indicating specific binding to the target SSEA-4. In contrast, the hAb6-3.1 alone does not have much cytotoxicity. This result indicates that the ADC achieves the advantages of both specificity and cytotoxicity. The preserved cytotoxicity would achieve the expected therapeutic effects, while the specificity would target the cancer cells and spare the normal cells, thereby minimizing adverse effects.

Example 21

In Vitro Cell Cytotoxicity Assay in Ovarian Cancer Cell Line

SKOV3, a SSEA4-expressing ovarian cancer cell line, was applied to demonstrate the efficacy of hAb6-3.1-A01. The method of cell cytotoxicity assay was described in Example 20. hAb6-3.1-A01 exhibited a more potent efficacy of cytotoxicity on SKOV3 in a nano-molar level.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

What the claim is:

1. An isolated monoclonal antibody or an antigen-binding fragment thereof wherein the monoclonal antibody or antigen-binding fragment specifically binds to the carbohydrate antigen SSEA4 having the structure
Neu5Acα2→3Galβ1→3GalNAcβ1→3Galα1→4Galβ1→4Glcβ1, wherein the antibody or antigen-binding fragment thereof comprises an H-CDR1, an H-CDR2, an H-CDR3, an L-CDR1, an L-CDR2, and an L-CDR3, i) the H-CDR1 having the sequence of SEQ ID No. 10, in which positions 1 and 5 of SEQ ID No. 10 are optionally substituted with Ser and Thr, respectively;

ii) the H-CDR2 having the sequence of SEQ ID No. 11, in which positions 1, 4, and 13 of SEQ ID No. 11 are optionally substituted with Ala;

iii) the H-CDR3 having the sequence of SEQ ID No. 12; in which position 3 of SEQ ID No. 12 is optionally substituted with Arg;

iv) the L-CDR1 having the sequence of SEQ ID No. 15; in which position 6 of SEQ ID No. 15 is optionally substituted with Ile or Ala;

v) the L-CDR2 having the sequence of SEQ ID No. 16, in which position 3 of SEQ ID No. 16 is optionally substituted with Tyr; and vi) the L-CDR3 having the sequence of SEQ ID No. 17, in which positions 3 and 6 of SEQ ID No. 17 are optionally substituted with Ala and Phe, respectively.

2. The isolated antibody of claim 1, wherein the antibody comprises:

a) a heavy chain variable domain having the sequence of: SEQ ID No. 13, in which positions 5, 17, 48, 67, and 112 of SEQ ID No. 13 are optionally substituted with Gln, Thr, Ile, Val, and Leu, respectively; and b) a light chain variable domain having the sequence of SEQ ID No. 18, in which positions 1, 11, 71, 82, and 103 of SEQ ID No. 18 are optionally substituted with Glu, Gln, Thr, Ala, and Val, respectively.

3. An isolated monoclonal antibody or an antigen-binding fragment thereof wherein the monoclonal antibody or antigen-binding fragment specifically binds to the carbohydrate antigen SSEA4 having the structure Neu5Acα2→3Galβ1→3GalNAcβ1→3Galα1→4Galβ1→4Glcβ1, wherein the antibody or antigen-binding fragment thereof comprises an H-CDR1, an H-CDR2, an H-CDR3, an L-CDR1, an L-CDR2, and an L-CDR3, i) the H-CDR1 having the sequence of SEQ ID No. 10, in which positions 1 or 5 of SEQ ID No. 10 are optionally substituted with Ser and Thr, respectively;

ii) the H-CDR2 having the sequence of SEQ ID No. 11, in which positions 1, 4, or 13 of SEQ ID No. 11 are optionally substituted with Ala;

iii) the H-CDR3 having the sequence of SEQ ID No. 12; in which position 3 of SEQ ID No. 12 is optionally substituted with Arg;

iv) the L-CDR1 having the sequence of SEQ ID No. 15; in which position 6 of SEQ ID No. 15 is optionally substituted with Ile or Ala;

v) the L-CDR2 having the sequence of SEQ ID No. 16, in which position 3 of SEQ ID No. 16 is optionally substituted with Tyr; and vi) the L-CDR3 having the sequence of SEQ ID No. 17, in which positions 3 or 6 of SEQ ID No. 17 are optionally substituted with Ala and Phe, respectively.

4. The isolated antibody of claim 3, wherein the antibody comprises:

a) a heavy chain variable domain having the sequence of: SEQ ID No. 13, in which positions 5, 17, 48, 67, or 112 of SEQ ID No. 13 are optionally substituted with Gln, Thr, Ile, Val, and Leu, respectively; and b) a light chain variable domain having the sequence of SEQ ID No. 18, in which positions 1, 11, 71, 82, or 103 of SEQ ID No. 18 are optionally substituted with Glu, Gln, Thr, Ala, and Val, respectively.

5. The isolated antibody of claim 3, wherein the antibody comprises:

a) a heavy chain variable domain having the sequence of: SEQ ID No. 13, in which a conservative amino acid substitution has been made at positions 5, 17, 48, and 67 of SEQ ID No. 13 and in which a non-conservative amino acid substitution has been made at position 112 of SEQ ID No. 13; and b) a light chain variable domain having the sequence of SEQ ID No. 18, in which a non-conservative amino acid substitution has been made at positions 1 and 11 of SEQ ID No. 18 and in which a conservative amino acid substitution has been made at positions 71, 82, and 103 of SEQ ID No. 18.

6. An isolated monoclonal antibody or an antigen-binding fragment thereof wherein the monoclonal antibody or antigen-binding fragment specifically binds to the carbohydrate antigen SSEA4 having the structure Neu5Acα2→3Galβ1→3GalNAcβ1→3Galα1→4Galβ1→4Glcβ1, wherein the antibody or antigen-binding fragment thereof comprises an H-CDR1, an H-CDR2, an H-CDR3, an L-CDR1, an L-CDR2, and an L-CDR3, i) the H-CDR1 having the sequence of SEQ ID No. 10, in which a conservative amino acid substitution has been made at positions 1 and 5 of SEQ ID No. 10;

ii) the H-CDR2 having the sequence of SEQ ID No. 11, in which a conservative amino acid substitution has been made at positions 1 and 4 of SEQ ID No. 11, and a non-conservative amino acid substitution has been made at position 13 of SEQ ID No. 11;

iii) the H-CDR3 having the sequence of SEQ ID No. 12; in which a non-conservative amino acid substitution has been made at position 3 of SEQ ID No. 12;

iv) the L-CDR1 having the sequence of SEQ ID No. 15; in which a conservative amino acid substitution has been made at position 6 of SEQ ID No. 15;

v) the L-CDR2 having the sequence of SEQ ID No. 16, in which a conservative amino acid substitution has been made at position 3 of SEQ ID No. 16; and vi) the L-CDR3 having the sequence of SEQ ID No. 17, in which a conservative amino acid substitution has been made at positions 3 and 6 of SEQ ID No. 17.

7. An isolated monoclonal antibody or an antigen-binding fragment thereof wherein the monoclonal antibody or antigen-binding fragment specifically binds to the carbohydrate antigen SSEA4 having the structure Neu5Acα2→3Galβ1→3GalNAcβ1→3Galα1→4Galβ1→4Glcβ1, wherein the antibody or antigen-binding fragment thereof comprises an H-CDR1, an H-CDR2, an H-CDR3, an L-CDR1, an L-CDR2, and an L-CDR3, i) the H-CDR1 having the sequence of SEQ ID No. 10, in which a conservative amino acid substitution has been made at positions 1 or 5 of SEQ ID No. 10;

ii) the H-CDR2 having the sequence of SEQ ID No. 11, in which a conservative amino acid substitution has been made at positions 1 or 4 of SEQ ID No. 11, and a non-conservative amino acid substitution has been made at position 13 of SEQ ID No. 11;

iii) the H-CDR3 having the sequence of SEQ ID No. 12 in which a non-conservative amino acid substitution has been made at position 3 of SEQ ID No. 12;

iv) the L-CDR1 having the sequence of SEQ ID No. 15; in which a conservative amino acid substitution has been made at position 6 of SEQ ID No. 15;

v) the L-CDR2 having the sequence of SEQ ID No. 16, in which a conservative amino acid substitution has been made at position 3 of SEQ ID No. 16; and vi) the L-CDR3 having the sequence of SEQ ID No. 17, in which a conservative amino acid substitution has been made at positions 3 or 6 of SEQ ID No. 17.

8. The isolated antibody of claim 7, wherein the antibody comprises:

a) a heavy chain variable domain having the sequence of: SEQ ID No. 13, in which a conservative amino acid substitution has been made at positions 5, 17, 48, or 67 of SEQ ID No. 13 and in which a non-conservative amino acid substitution has been made at position 112 of SEQ ID No. 13; and b) a light chain variable domain having the sequence of SEQ ID No. 18, in which a non-conservative amino acid substitution has been made at positions 1 and 11 of SEQ ID No. 18 and in which a conservative amino acid substitution has been made at positions 71, 82, or 103 of SEQ ID No. 18.

9. The isolated antibody or antigen-binding fragment of any one of claims 1-8, wherein the antibody or antigen-binding fragment is:
   a) a chimeric antibody or a fragment thereof; or
   b) a humanized antibody or fragment thereof; or
   c) a human antibody or fragment thereof; or
   d) an antigen-binding fragment selected from the group consisting of Fab, Fab', Fv, scFv, dsFv, F(ab)$_2$, Fd and a diabody.

10. The isolated antibody or antigen-binding fragment of claim 9, wherein the antibody is IgG.

11. The isolated antibody or antigen-binding fragment of claim 9, wherein the antibody has CDC and/or ADCC inducing activity upon binding to the target cells.

12. A pharmaceutical composition, comprising the isolated antibody or antigen-binding fragment thereof of claim 9 and a pharmaceutical acceptable carrier.

13. The pharmaceutical composition of claim 12, further comprising one or more therapeutic agents.

14. The pharmaceutical composition of claim 13, wherein the therapeutic agent is selected from therapeutic antibodies, chemotherapeutic agents, or cytokines.

15. An immunoconjugate comprising the antibody of claim 9 and a cytotoxic agent.

16. The immunoconjugate of claim 15, having the formula AB-(L-D)p, wherein:
   (a) AB is the antibody of claim 9;
   (b) L is a linker;
   (c) D is a suitable cytotoxic drug, and
   (d) p ranges from 1 to 8.

17. The immunoconjugate (ADC) of claim 16, wherein the drug is MMAE or MMAF.

18. The immunoconjugate of claim 16, wherein the linker is cleavable linker.

19. The ADC of claim 18, wherein the cleavable linker is an alkoxyamine-cleavable linker.

20. A pharmaceutical formulation comprising the immunoconjugate of claim 15 and a pharmaceutically acceptable carrier.

21. The pharmaceutical formulation of claim 20, further comprising an additional therapeutic agent.

22. The isolated antibody of claim 9, wherein the antibody specifically binds to SSEA4 with an affinity constant less than $10^{-7}$ M.

23. The isolated antibody of claim 9, wherein the antibody is IgG$_1$, IgG$_2$, IgG$_3$, or IgG$_4$.

24. The isolated antibody of claim 9, wherein the antibody is IgG$_{1\lambda}$ or IgG$_{1\kappa}$.

25. The monoclonal antibody or antigen-binding portion thereof of claim 9, wherein the monoclonal antibody or antigen-binding portion thereof binds to SSEA4 with a K$_D$ of $1\times^{31\ 7}$ or less, and wherein the K$_D$ is measured by surface plasmon resonance (Biacore) analysis.

26. The isolated anti-SSEA4 antibody or binding fragment thereof of claim 25 wherein the binding affinity is <50 nM.

* * * * *